(12) United States Patent
Houchen

(10) Patent No.: US 12,415,867 B2
(45) Date of Patent: Sep. 16, 2025

(54) ANTI-DCLK1 ANTIBODIES AND CHIMERIC ANTIGEN RECEPTORS, AND COMPOSITIONS AND METHODS OF USE THEREOF

(71) Applicant: The Board of Regents of the University of Oklahoma, Norman, OK (US)

(72) Inventor: Courtney W. Houchen, Edmond, OK (US)

(73) Assignee: The Board of Regents of the University of Oklahoma, Norman, OK (US)

(*) Notice: Subject to any disclaimer, the term of this patent is extended or adjusted under 35 U.S.C. 154(b) by 0 days.

(21) Appl. No.: 18/427,038

(22) Filed: Jan. 30, 2024

(65) Prior Publication Data

US 2024/0317893 A1    Sep. 26, 2024

Related U.S. Application Data

(63) Continuation of application No. 16/769,567, filed as application No. PCT/US2018/063702 on Dec. 3, 2018, now Pat. No. 12,084,514.

(60) Provisional application No. 62/594,464, filed on Dec. 4, 2017.

(51) Int. Cl.
| | | |
|---|---|---|
| *A61P 35/00* | (2006.01) | |
| *A61K 35/17* | (2025.01) | |
| *A61K 40/11* | (2025.01) | |
| *A61K 40/31* | (2025.01) | |
| *A61K 40/42* | (2025.01) | |
| *C07K 14/705* | (2006.01) | |
| *C07K 14/725* | (2006.01) | |
| *C07K 16/40* | (2006.01) | |
| *A61K 38/00* | (2006.01) | |
| *A61K 39/00* | (2006.01) | |
| *G01N 33/50* | (2006.01) | |

(52) U.S. Cl.
CPC .............. *C07K 16/40* (2013.01); *A61K 35/17* (2013.01); *A61K 40/11* (2025.01); *A61K 40/31* (2025.01); *A61K 40/4251* (2025.01); *A61P 35/00* (2018.01); *C07K 14/7051* (2013.01); *C07K 14/70517* (2013.01); *C07K 14/70521* (2013.01); *A61K 38/00* (2013.01); *A61K 2039/505* (2013.01); *A61K 2239/31* (2023.05); *A61K 2239/38* (2023.05); *C12Y 207/11001* (2013.01); *G01N 33/5008* (2013.01); *G01N 2800/52* (2013.01)

(58) Field of Classification Search
CPC ..... A61P 35/00; A61K 40/4251; A61K 40/31; A61K 40/11; A61K 35/17; C07K 14/7051; C07K 14/70517; C07K 14/70521
See application file for complete search history.

*Primary Examiner* — Nelson B Moseley, II
*Assistant Examiner* — Dennis J Sullivan
(74) *Attorney, Agent, or Firm* — Dunlap Codding, P.C.

(57) ABSTRACT

CAR cells and humanized antibodies targeting DCLK1 expressed on/in tumor cells or circulating cancer cells are described as a new method of cancer treatment. The antibodies and cells are safe and effective in patients and can be used to treat cancer expressing the DCLK1 proteins.

18 Claims, 15 Drawing Sheets

Specification includes a Sequence Listing.

Biotinylated DCLK1 protein

SEQUENCE LISTING

```
Sequence total quantity: 105
SEQ ID NO: 1              moltype = AA  length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 1
EVQLVESGGG LVQPGGSLRL SCAASGFTFS SYYMSWVRQA PGKGLELVSA INSNGGSTYY   60
PDSVKGRFTI SRDNSKNTLY LQMNSLRAED TAVYYCARHG GNYWYFDVWG QGTMVTVSS   119

SEQ ID NO: 2              moltype = AA  length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 2
EVQLVESGGG LVQPGGSLRL SCAASGFTFS SYYMSWVRQA PGKRLELVSA INSNGGSTYY   60
PDSVKGRFTI SRDNSKNTLY LQMNSLRAED TAVYYCARHG GNYWYFDVWG QGTMVTVSS   119

SEQ ID NO: 3              moltype = AA  length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 3
EVKLLESGGG LVQPGGSLRL SCAASGFTFS SYYMSWVRQA PGKRLELVSA INSNGGSTYY   60
PDSVKGRFTI SRDNSKNTLY LQMNSLRAED TAVYYCARHG GNYWYFDVWG QGTTVTVSS   119

SEQ ID NO: 4              moltype = AA  length = 119
FEATURE                   Location/Qualifiers
REGION                    1..119
                          note = Description of Artificial Sequence: Synthetic
                          polypeptide
source                    1..119
```

```
                              mol_type = protein
                              organism = synthetic construct
SEQUENCE: 4
EVQLVESGGG LVQPGGSLRL SCAASGFTFS SYYMSWVRQA PGKGLEWVSA INSNGGSTYY     60
PDTVKGRFTI SRDNSKNTLY LQMNSLRAED TAVYYCAKHG GNYWYFDVWG QGTLVTVSS     119

SEQ ID NO: 5              moltype = AA   length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 5
EVQLVESGGG LVQPGGSLRL SCAASGFTFS SYYMSWVRQA PGKGLEWVSA INSNGGSTYY     60
PDTVKGRFTI SRDNSKNTLY LQMNSLRAED TAVYYCARHG GNYWYFDVWG QGTLVTVSS     119

SEQ ID NO: 6              moltype = AA   length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 6
EVQLVESGGG LVQPGGSLRL SCAASGFTFS SYYMSWVRQA PGKGLEWVAA INSNGGSTYY     60
PDTVKGRFTI SRDNSKNTLY LQMNSLRAED TAVYYCARHG GNYWYFDVWG QGTLVTVSS     119

SEQ ID NO: 7              moltype = AA   length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 7
EVQLVESGGG LVQPGGSLRL SCAASGFTFS SYYMSWVRQA PGKGLELVAA INSNGGSTYY     60
PDTVKGRFTI SRDNSKNTLY LQMNSLRAED TAVYYCARHG GNYWYFDVWG QGTLVTVSS     119

SEQ ID NO: 8              moltype = AA   length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 8
EVQLVESGGG LVQPGGSLRL SCAASGFTFS SYYMSWVRQA PGKGLEWVSA INSSGGSTYY     60
ADSVKGRFTI SRDNSKNTLY LQMNSLRAED TAVYYCARHG GNYWYFDVWG QGTLVTVSS     119

SEQ ID NO: 9              moltype = AA   length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 9
EVQLVESGGG LVQPGGSLRL SCAASGFTFS SYYMSWVRQA PGKGLELVAA INSSGGSTYY     60
PDSVKGRFTI SRDNSKNTLY LQMNSLRAED TAVYYCARHG GNYWYFDVWG QGTLVTVSS     119

SEQ ID NO: 10             moltype = AA   length = 119
FEATURE                   Location/Qualifiers
REGION                    1..119
                          note = Description of Artificial Sequence: Synthetic
                          polypeptide
source                    1..119
                          mol_type = protein
                          organism = synthetic construct
SEQUENCE: 10
DVKLVESGGG LVKLGGSLKL SCAASGFTFS SYYMSWVRQT PEKRLELVAA INSNGGSTYY     60
PDTVKGRFTI SRDNAKNTLY LQMSSLKSED TALYYCARHG GNYWYFDVWG AGTTVTVSS     119

SEQ ID NO: 11             moltype = AA   length = 113
```

```
FEATURE              Location/Qualifiers
REGION               1..113
                     note = Description of Artificial Sequence: Synthetic
                      polypeptide
source               1..113
                     mol_type = protein
                     organism = synthetic construct
SEQUENCE: 11
DIVMTQSPDS LAVSLGERAT INCKSSQSLL YSSNQKNYLA WYQQKPGQSP KLLIYWASTR    60
ESGVPDRFSG SGSGTDFTLT ISSLQAEDVA VYYCQQYYSY PYTFGQGTKL EIK          113

SEQ ID NO: 12        moltype = AA  length = 240
FEATURE              Location/Qualifiers
REGION               1..240
                     note = Description of Artificial Sequence: Synthetic
                      polypeptide
source               1..240
                     mol_type = protein
                     organism = synthetic construct
SEQUENCE: 12
METDTLLLWV LLLWVPGSTG DIVMTQSPDS LAVSLGERAT INCKSSQSLL YSSNQKNYLA    60
WYQQKPGQPP KLLIYWASTR ESGVPDRFSG SGSGTDFTLT ISSVQAEDVA VYYCQQYYSY   120
PYTFGGGTKV EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 13        moltype = AA  length = 113
FEATURE              Location/Qualifiers
REGION               1..113
                     note = Description of Artificial Sequence: Synthetic
                      polypeptide
source               1..113
                     mol_type = protein
                     organism = synthetic construct
SEQUENCE: 13
DIVMTQSPDS LAVSLGERAT INCKSSQSLL YSSNQKNYLA WYQQKPGQPP KLLIYWASTR    60
ESGVPDRFSG SGSGTDFTLT ISSLQAEDVA VYYCQQYYSY PYTFGQGTKL EIK          113

SEQ ID NO: 14        moltype = AA  length = 113
FEATURE              Location/Qualifiers
REGION               1..113
                     note = Description of Artificial Sequence: Synthetic
                      polypeptide
source               1..113
                     mol_type = protein
                     organism = synthetic construct
SEQUENCE: 14
DIVMSQSPDS LAVSLGERAT ISCKSSQSLL YSSNQKNYLA WYQQKPGQPP KLLIYWASTR    60
ESGVPDRFSG SGSGTDFTLT ISSLQAEDVA VYYCQQYYSY PYTFGQGTKL EIK          113

SEQ ID NO: 15        moltype = AA  length = 113
FEATURE              Location/Qualifiers
REGION               1..113
                     note = Description of Artificial Sequence: Synthetic
                      polypeptide
source               1..113
                     mol_type = protein
                     organism = synthetic construct
SEQUENCE: 15
DIVMSQSPSS LAVSVGEKVT MSCKSSQSLL YSSNQKNYLA WYQQKPGQSP KLLIYWASTR    60
ESGVPDRFTG SGSGTDFTLT ISSVKAEDLA VYYCQQYYSY PYTFGGGTKL EIK          113

SEQ ID NO: 16        moltype = AA  length = 472
FEATURE              Location/Qualifiers
REGION               1..472
                     note = Description of Artificial Sequence: Synthetic
                      polypeptide
source               1..472
                     mol_type = protein
                     organism = synthetic construct
SEQUENCE: 16
MDPKGSLSWR ILLFLSLAFE LSYGEVQLVE SGGGLVQPGG SLRLSCAASG FTFSSYYMSW    60
VRQAPGKGLE LVSAINSNGG STYYPDSVKG RFTISRDNSK NTLYLQMNSL RAEDTAVYYC   120
ARHGGNYWYF DVWGQGTMVT VSSASTKGPS VFPLAPSSKS TSGGTAALGC LVKDYFPEPV   180
TVSWNSGALT SGVHTFPAVL QSSGLYSLSS VVTVPSSSLG TQTYICNVNH KPSNTKVDKK   240
VEPKSCDKTH TCPPCPAPEL LGGPSVFLFP PKPKDTLMIS RTPEVTCVVV DVSHEDPEVK   300
FNWYVDGVEV HNAKTKPREE QYNSTYRVVS VLTVLHQDWL NGKEYKCKVS NKALPAPIAK   360
TISKAKGQPR EPQVYTLPPS RDELTKNQVS LTCLVKGFYP SDIAVEWESN GQPENNYKTT   420
PPVLDSDGSF FLYSKLTVDK SRWQQGNVFS CSVMHEALHN HYTQKSLSLS PG           472
```

```
SEQ ID NO: 17              moltype = AA  length = 472
FEATURE                    Location/Qualifiers
REGION                     1..472
                           note = Description of Artificial Sequence: Synthetic
                           polypeptide
source                     1..472
                           mol_type = protein
                           organism = synthetic construct
SEQUENCE: 17
MDPKGSLSWR ILLFLSLAFE LSYGEVQLVE SGGGLVQPGG SLRLSCAASG FTFSSYYMSW   60
VRQAPGKRLE LVSAINSNGG STYYPDSVKG RFTISRDNSK NTLYLQMNSL RAEDTAVYYC  120
ARHGGNYWYF DVWGQGTMVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIAK  360
TISKAKGQPR EPQVYTLPPS RDELTKNQVS LTCLVKGFYP SDIAVEWESN GQPENNYKTT  420
PPVLDSDGSF FLYSKLTVDK SRWQQGNVFS CSVMHEALHN HYTQKSLSLS PG          472

SEQ ID NO: 18              moltype = AA  length = 472
FEATURE                    Location/Qualifiers
REGION                     1..472
                           note = Description of Artificial Sequence: Synthetic
                           polypeptide
source                     1..472
                           mol_type = protein
                           organism = synthetic construct
SEQUENCE: 18
MDPKGSLSWR ILLFLSLAFE LSYGEVKLLE SGGGLVQPGG SLRLSCAASG FTFSSYYMSW   60
VRQAPGKRLE LVSAINSNGG STYYPDSVKG RFTISRDNSK NTLYLQMNSL RAEDTAVYYC  120
ARHGGNYWYF DVWGQGTTVT VSSASTKGPS VFPLAPSSKS TSGGTAALGC LVKDYFPEPV  180
TVSWNSGALT SGVHTFPAVL QSSGLYSLSS VVTVPSSSLG TQTYICNVNH KPSNTKVDKK  240
VEPKSCDKTH TCPPCPAPEL LGGPSVFLFP PKPKDTLMIS RTPEVTCVVV DVSHEDPEVK  300
FNWYVDGVEV HNAKTKPREE QYNSTYRVVS VLTVLHQDWL NGKEYKCKVS NKALPAPIAK  360
TISKAKGQPR EPQVYTLPPS RDELTKNQVS LTCLVKGFYP SDIAVEWESN GQPENNYKTT  420
PPVLDSDGSF FLYSKLTVDK SRWQQGNVFS CSVMHEALHN HYTQKSLSLS PG          472

SEQ ID NO: 19              moltype = AA  length = 138
FEATURE                    Location/Qualifiers
REGION                     1..138
                           note = Description of Artificial Sequence: Synthetic
                           polypeptide
source                     1..138
                           mol_type = protein
                           organism = synthetic construct
SEQUENCE: 19
MEFGLSWLFL VAKIKGVQCE VQLVESGGGL VQPGGSLRLS CAASGFTFSS YYMSWVRQAP   60
GKGLEWVSAI NSNGGSTYYP DTVKGRFTIS RDNSKNTLYL QMNSLRAEDT AVYYCAKHGG  120
NYWYFDVWGQ GTLVTVSS                                                138

SEQ ID NO: 20              moltype = AA  length = 138
FEATURE                    Location/Qualifiers
REGION                     1..138
                           note = Description of Artificial Sequence: Synthetic
                           polypeptide
source                     1..138
                           mol_type = protein
                           organism = synthetic construct
SEQUENCE: 20
MEFGLSWLFL VAKIKGVQCE VQLVESGGGL VQPGGSLRLS CAASGFTFSS YYMSWVRQAP   60
GKGLEWVSAI NSNGGSTYYP DTVKGRFTIS RDNSKNTLYL QMNSLRAEDT AVYYCARHGG  120
NYWYFDVWGQ GTLVTVSS                                                138

SEQ ID NO: 21              moltype = AA  length = 138
FEATURE                    Location/Qualifiers
REGION                     1..138
                           note = Description of Artificial Sequence: Synthetic
                           polypeptide
source                     1..138
                           mol_type = protein
                           organism = synthetic construct
SEQUENCE: 21
MEFGLSWLFL VAKIKGVQCE VQLVESGGGL VQPGGSLRLS CAASGFTFSS YYMSWVRQAP   60
GKGLEWVAAI NSNGGSTYYP DTVKGRFTIS RDNSKNTLYL QMNSLRAEDT AVYYCARHGG  120
NYWYFDVWGQ GTLVTVSS                                                138

SEQ ID NO: 22              moltype = AA  length = 138
FEATURE                    Location/Qualifiers
REGION                     1..138
                           note = Description of Artificial Sequence: Synthetic
```

```
                            polypeptide
source                      1..138
                            mol_type = protein
                            organism = synthetic construct
SEQUENCE: 22
MEFGLSWLFL VAKIKGVQCE VQLVESGGGL VQPGGSLRLS CAASGFTFSS YYMSWVRQAP    60
GKGLELVAAI NSNGGSTYYP DTVKGRFTIS RDNSKNTLYL QMNSLRAEDT AVYYCARHGG   120
NYWYFDVWGQ GTLVTVSS                                                 138

SEQ ID NO: 23               moltype = AA   length = 138
FEATURE                     Location/Qualifiers
REGION                      1..138
                            note = Description of Artificial Sequence: Synthetic
                             polypeptide
source                      1..138
                            mol_type = protein
                            organism = synthetic construct
SEQUENCE: 23
MEFGLSWLFL VAKIKGVQCE VQLVESGGGL VQPGGSLRLS CAASGFTFSS YYMSWVRQAP    60
GKGLEWVSAI NSSGGSTYYA DSVKGRFTIS RDNSKNTLYL QMNSLRAEDT AVYYCARHGG   120
NYWYFDVWGQ GTLVTVSS                                                 138

SEQ ID NO: 24               moltype = AA   length = 138
FEATURE                     Location/Qualifiers
REGION                      1..138
                            note = Description of Artificial Sequence: Synthetic
                             polypeptide
source                      1..138
                            mol_type = protein
                            organism = synthetic construct
SEQUENCE: 24
MEFGLSWLFL VAKIKGVQCE VQLVESGGGL VQPGGSLRLS CAASGFTFSS YYMSWVRQAP    60
GKGLELVAAI NSSGGSTYYP DSVKGRFTIS RDNSKNTLYL QMNSLRAEDT AVYYCARHGG   120
NYWYFDVWGQ GTLVTVSS                                                 138

SEQ ID NO: 25               moltype = AA   length = 138
FEATURE                     Location/Qualifiers
REGION                      1..138
                            note = Description of Artificial Sequence: Synthetic
                             polypeptide
source                      1..138
                            mol_type = protein
                            organism = synthetic construct
SEQUENCE: 25
MNFGLRLIFL VLVLKGVLCD VKLVESGGGL VKLGGSLKLS CAASGFTFSS YYMSWVRQTP    60
EKRLELVAAI NSNGGSTYYP DTVKGRFTIS RDNAKNTLYL QMSSLKSEDT ALYYCARHGG   120
NYWYFDVWGA GTTVTVSS                                                 138

SEQ ID NO: 26               moltype = AA   length = 240
FEATURE                     Location/Qualifiers
REGION                      1..240
                            note = Description of Artificial Sequence: Synthetic
                             polypeptide
source                      1..240
                            mol_type = protein
                            organism = synthetic construct
SEQUENCE: 26
METDTLLLWV LLLWVPGSTG DIVMTQSPDS LAVSLGERAT INCKSSQSLL YSSNQKNYLA    60
WYQQKPGQPP KLLIYWASTR ESGVPDRFSG SGSGTDFTLT ISSLQAEDVA VYYCQQYYSY   120
PYTFGQGTKL EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 27               moltype = AA   length = 240
FEATURE                     Location/Qualifiers
REGION                      1..240
                            note = Description of Artificial Sequence: Synthetic
                             polypeptide
source                      1..240
                            mol_type = protein
                            organism = synthetic construct
SEQUENCE: 27
METDTLLLWV LLLWVPGSTG DIVMTQSPDS LAVSLGERAT INCKSSQSLL YSSNQKNYLA    60
WYQQKPGQSP KLLIYWASTR ESGVPDRFSG SGSGTDFTLT ISSLQAEDVA VYYCQQYYSY   120
PYTFGQGTKL EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 28               moltype = AA   length = 240
FEATURE                     Location/Qualifiers
REGION                      1..240
```

```
                        note = Description of Artificial Sequence: Synthetic
                           polypeptide
source                  1..240
                        mol_type = protein
                        organism = synthetic construct
SEQUENCE: 28
METDTLLLWV LLLWVPGSTG DIVMTQSPDS LAVSLGERAT INCKSSQSLL YSSNQKNYLA    60
WYQQKPGQPP KLLIYWASTR ESGVPDRFSG SGSGTDFTLT ISSVQAEDVA VYYCQQYYSY   120
PYTFGGGTKV EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240

SEQ ID NO: 29           moltype = AA  length = 133
FEATURE                 Location/Qualifiers
REGION                  1..133
                        note = Description of Artificial Sequence: Synthetic
                           polypeptide
source                  1..133
                        mol_type = protein
                        organism = synthetic construct
SEQUENCE: 29
MVLQTQVFIS LLLWISGAYG DIVMTQSPDS LAVSLGERAT INCKSSQSLL YSSNQKNYLA    60
WYQQKPGQPP KLLIYWASTR ESGVPDRFSG SGSGTDFTLT ISSLQAEDVA VYYCQQYYSY   120
PYTFGQGTKL EIK                                                     133

SEQ ID NO: 30           moltype = AA  length = 133
FEATURE                 Location/Qualifiers
REGION                  1..133
                        note = Description of Artificial Sequence: Synthetic
                           polypeptide
source                  1..133
                        mol_type = protein
                        organism = synthetic construct
SEQUENCE: 30
MVLQTQVFIS LLLWISGAYG DIVMSQSPDS LAVSLGERAT ISCKSSQSLL YSSNQKNYLA    60
WYQQKPGQPP KLLIYWASTR ESGVPDRFSG SGSGTDFTLT ISSLQAEDVA VYYCQQYYSY   120
PYTFGQGTKL EIK                                                     133

SEQ ID NO: 31           moltype = AA  length = 133
FEATURE                 Location/Qualifiers
REGION                  1..133
                        note = Description of Artificial Sequence: Synthetic
                           polypeptide
source                  1..133
                        mol_type = protein
                        organism = synthetic construct
SEQUENCE: 31
MDSQAQVLML LLLWVSGTCG DIVMSQSPSS LAVSVGEKVT MSCKSSQSLL YSSNQKNYLA    60
WYQQKPGQSP KLLIYWASTR ESGVPDRFTG SGSGTDFTLT ISSVKAEDLA VYYCQQYYSY   120
PYTFGGGTKL EIK                                                     133

SEQ ID NO: 32           moltype = DNA  length = 1422
FEATURE                 Location/Qualifiers
misc_feature            1..1422
                        note = Description of Artificial Sequence: Synthetic
                           polynucleotide
source                  1..1422
                        mol_type = other DNA
                        organism = synthetic construct
SEQUENCE: 32
atggacccca agggcagcct gagctggaga atcctgctgt tcctgagcct ggccttcgag    60
ctgagctacg gcgaggtgca actggtggag tccggaggcg gactggtgca gcccggaggt   120
agccttaggc tgagctgtgc cgcaagtggc ttcaccttca gcagctacta catgagctgg   180
gtgaggcagg cccctggcaa gggcctggag ctggtgagcg ccatcaacag caacggcggc   240
agcacctact accccgacag cgtgaagggc aggttcacca tcagcaggga caatgccaag   300
aacacccctg tcctgcagat gaacagcctg agggccgagg acacagccgt gtactactgc   360
gccaggcatg gcgcaactac tggtactttc gactgtgggg tcaaggaac aatggtgaca   420
gttagttccg ctagcaccaa gggccccagc gtgttccctc tggcccccag cagcaagagc   480
accagcggcg gaaccgccgc cctgggctgc ctggtgaagg actactttcc cgagcccgtg   540
accgtgtcct ggaacagcgg cgctctgacc agcggagtgc acaccttccc tgccgtgctg   600
cagagcagcg gcctgtactc cctgagcagc gtggtgaccg tgcccagcag cagcctgggc   660
acccagacct acatctgcaa cgtgaaccac aagccctcca caccaaggt ggacaagaag   720
gtggagccta gagctgcga caagacccac acctgccct cctgccccgc cccgagctg   780
ctgggcggac cgagcgtgtt cctgttccct cccaagccca aggacaccct gatgatcagc   840
cgcacccccg aggtgacctg cgtggtggtg gacgtgagcc acgaggaccc tgaggtgaag   900
ttcaactggt acgtggacgg cgtggaggtg cacaacgcca agaccaagcc tcgggaggag   960
cagtacaact ccacctaccg cgtggtgagc gtgctgaccg tgctgcacca ggactggctg  1020
aacggcaagg agtacaagtg caaggtgagc aacaaggccc tgcccgctcc catcgcaaag  1080
accatcagca aggccaaggg ccagccccgg gagcctcagg tgtacaccct gcccccagc   1140
cgcgacgagc tgaccaagaa ccaggtgagc ctgacctgcc tggtgaaggg cttctacccc  1200
```

```
tccgacatcg ccgtggagtg ggagagcaac ggccagcctg agaacaacta caagaccacc    1260
cctcccgtgc tggacagcga cggcagcttc ttcctgtaca gcaagctgac cgtggacaag    1320
tcccggtggc agcagggcaa cgtgttcagc tgcagcgtga tgcacgaggc cctgcacaac    1380
cactacaccc agaagagcct gagcctgagc cccggatagt aa                       1422

SEQ ID NO: 33            moltype = DNA   length = 1422
FEATURE                  Location/Qualifiers
misc_feature             1..1422
                         note = Description of Artificial Sequence: Synthetic
                          polynucleotide
source                   1..1422
                         mol_type = other DNA
                         organism = synthetic construct
SEQUENCE: 33
atggacccca agggcagcct gagctggaga atcctgctgt tcctgagcct ggccttcgag    60
ctgagctacg gcgaggtgca actggtggag tccggaggcg gactggtgca gcccggaggt    120
agccttaggc tgagctgtgc cgcaagtggc ttcaccttca gcagctacta catgagctgg    180
gtgaggcagg cccctggcaa gcgcctggag ctggtgagcg ccatcaacag caacggcggc    240
agcacctact accccgacag cgtgaagggc aggttcacca tcagcaggga caatagcaag    300
aacaccctgt acctgcagat gaacagcctg agggccgagg acacagccgt gtactactgc    360
gccaggcatg gcggcaacta ctggtacttc gacgtgtggg gtcaaggaac aatggtgaca    420
gttagttccg ctagcaccaa gggccccagc gtgttccctc tggccccccag cagcaagagc    480
accagcggcg gaaccgccgc cctgggctgc ctggtgaagg actacttccc cgagcccgtg    540
accgtgtcct ggaacagcgg cgctctgacc agcggagtgc acaccttccc tgccgtgctg    600
cagagcagcg gcctgtactc cctgagcagc gtggtgaccg tgcccagcag cagcctgggc    660
acccagacct acatctgcaa cgtgaaccac aagccctcca acaccaaggt ggacaagaag    720
gtggagccta agagctgcga caagacccac acctgccctc cctgccccgc ccccgagctg    780
ctgggcggac ccagcgtgtt cctgttccct cccaagccca aggacaccct gatgatcagc    840
cgcacccccg aggtgacctg cgtggtggtg gacgtgagcc acgaggaccc cgaggtgaag    900
ttcaactggt acgtggacgg cgtggaggtg cacaacgcca agaccaagcc tcgggaggag    960
cagtacaact ccacctaccg cgtggtgagc gtgctgaccg tgctgcacca ggactggctg    1020
aacggcaagg agtacaagtg caaggtgagc aacaaggccc tgcccgctcc catcgcaaag    1080
accatcagca aggccaaggg ccagcccgg gagcctcagg tgtacaccct gcccccagc     1140
cgcgacgagc tgaccaagaa ccaggtgagc ctgacctgcc tggtgaaggg cttctacccc    1200
tccgacatcg ccgtggagtg ggagagcaac ggccagcctg agaacaacta caagaccacc    1260
cctcccgtgc tggacagcga cggcagcttc ttcctgtaca gcaagctgac cgtggacaag    1320
tcccggtggc agcagggcaa cgtgttcagc tgcagcgtga tgcacgaggc cctgcacaac    1380
cactacaccc agaagagcct gagcctgagc cccggatagt aa                       1422

SEQ ID NO: 34            moltype = DNA   length = 1422
FEATURE                  Location/Qualifiers
misc_feature             1..1422
                         note = Description of Artificial Sequence: Synthetic
                          polynucleotide
source                   1..1422
                         mol_type = other DNA
                         organism = synthetic construct
SEQUENCE: 34
atggacccca agggcagcct gagctggaga atcctgctgt tcctgagcct ggccttcgag    60
ctgagctacg gcgaggtgaa actgttggag tccggaggcg gactggtgca gcccggaggt    120
agccttaggc tgagctgtgc cgcaagtggc ttcaccttca gcagctacta catgagctgg    180
gtgaggcagg cccctggcaa gcgcctggag ctggtgagcg ccatcaacag caacggcggc    240
agcacctact accccgacag cgtgaagggc aggttcacca tcagcaggga caatagcaag    300
aacaccctgt acctgcagat gaacagcctg agggccgagg acacagccgt gtactactgc    360
gccaggcatg gcggcaacta ctggtacttc gacgtgtggg gtcaaggaac aactgtgaca    420
gttagttccg ctagcaccaa gggccccagc gtgttccctc tggccccccag cagcaagagc    480
accagcggcg gaaccgccgc cctgggctgc ctggtgaagg actacttccc cgagcccgtg    540
accgtgtcct ggaacagcgg cgctctgacc agcggagtgc acaccttccc tgccgtgctg    600
cagagcagcg gcctgtactc cctgagcagc gtggtgaccg tgcccagcag cagcctgggc    660
acccagacct acatctgcaa cgtgaaccac aagccctcca acaccaaggt ggacaagaag    720
gtggagccta agagctgcga caagacccac acctgccctc cctgccccgc ccccgagctg    780
ctgggcggac ccagcgtgtt cctgttccct cccaagccca aggacaccct gatgatcagc    840
cgcacccccg aggtgacctg cgtggtggtg gacgtgagcc acgaggaccc cgaggtgaag    900
ttcaactggt acgtggacgg cgtggaggtg cacaacgcca agaccaagcc tcgggaggag    960
cagtacaact ccacctaccg cgtggtgagc gtgctgaccg tgctgcacca ggactggctg    1020
aacggcaagg agtacaagtg caaggtgagc aacaaggccc tgcccgctcc catcgcaaag    1080
accatcagca aggccaaggg ccagcccgg gagcctcagg tgtacaccct gcccccagc     1140
cgcgacgagc tgaccaagaa ccaggtgagc ctgacctgcc tggtgaaggg cttctacccc    1200
tccgacatcg ccgtggagtg ggagagcaac ggccagcctg agaacaacta caagaccacc    1260
cctcccgtgc tggacagcga cggcagcttc ttcctgtaca gcaagctgac cgtggacaag    1320
tcccggtggc agcagggcaa cgtgttcagc tgcagcgtga tgcacgaggc cctgcacaac    1380
cactacaccc agaagagcct gagcctgagc cccggatagt aa                       1422

SEQ ID NO: 35            moltype = DNA   length = 414
FEATURE                  Location/Qualifiers
misc_feature             1..414
                         note = Description of Artificial Sequence: Synthetic
                          polynucleotide
source                   1..414
```

```
                        mol_type = other DNA
                        organism = synthetic construct
SEQUENCE: 35
atggagtttg ggctgagctg gcttttcctt gtggctaaaa taaaaggtgt ccagtgtgag    60
gtgcagctgg tggagtctgg gggaggcttg gtacagcctg gggggtccct gagactctcc   120
tgtgcagcct ctggattcac ctttagcagc tattacatga gctgggtccg ccaggctcca   180
gggaaggggc tggagtgggt ctcagctatt aactccaacg gtggtagcac atactaccca   240
gacaccgtga agggccggtt caccatctcc agagacaatt ccaagaacac gctgtatctg   300
caaatgaaca gcctgagagc cgaggacacg gccgtatatt actgtgcgaa catgggggt    360
aactactggg actttgacgt ctggggccaa ggaaccctgg tcaccgtctc ctca         414

SEQ ID NO: 36          moltype = DNA   length = 414
FEATURE                Location/Qualifiers
misc_feature           1..414
                       note = Description of Artificial Sequence: Synthetic
                         polynucleotide
source                 1..414
                       mol_type = other DNA
                       organism = synthetic construct
SEQUENCE: 36
atggagtttg ggctgagctg gcttttcctt gtggctaaaa taaaaggtgt ccagtgtgag    60
gtgcagctgg tggagtctgg gggaggcttg gtacagcctg gggggtccct gagactctcc   120
tgtgcagcct ctggattcac ctttagcagc tattacatga gctgggtccg ccaggctcca   180
gggaaggggc tggagtgggt ctcagctatt aactccaacg gtggtagcac atactaccca   240
gacaccgtga agggccggtt caccatctcc agagacaatt ccaagaacac gctgtatctg   300
caaatgaaca gcctgagagc cgaggacacg gccgtatatt actgtgcgag catgggggt    360
aactactggg actttgacgt ctggggccaa ggaaccctgg tcaccgtctc ctca         414

SEQ ID NO: 37          moltype = DNA   length = 414
FEATURE                Location/Qualifiers
misc_feature           1..414
                       note = Description of Artificial Sequence: Synthetic
                         polynucleotide
source                 1..414
                       mol_type = other DNA
                       organism = synthetic construct
SEQUENCE: 37
atggagtttg ggctgagctg gcttttcctt gtggctaaaa taaaaggtgt ccagtgtgag    60
gtgcagctgg tggagtctgg gggaggcttg gtacagcctg gggggtccct gagactctcc   120
tgtgcagcct ctggattcac ctttagcagc tattacatga gctgggtccg ccaggctcca   180
gggaaggggc tggagtgggt cgcagctatt aactccaacg gtggtagcac atactaccca   240
gacaccgtga agggccggtt caccatctcc agagacaatt ccaagaacac gctgtatctg   300
caaatgaaca gcctgagagc cgaggacacg gccgtatatt actgtgcgag catgggggt    360
aactactggg actttgacgt ctggggccaa ggaaccctgg tcaccgtctc ctca         414

SEQ ID NO: 38          moltype = DNA   length = 414
FEATURE                Location/Qualifiers
misc_feature           1..414
                       note = Description of Artificial Sequence: Synthetic
                         polynucleotide
source                 1..414
                       mol_type = other DNA
                       organism = synthetic construct
SEQUENCE: 38
atggagtttg ggctgagctg gcttttcctt gtggctaaaa taaaaggtgt ccagtgtgag    60
gtgcagctgg tggagtctgg gggaggcttg gtacagcctg gggggtccct gagactctcc   120
tgtgcagcct ctggattcac ctttagcagc tattacatga gctgggtccg ccaggctcca   180
gggaaggggc tggagctggt cgcagctatt aactccaacg gtggtagcac atactaccca   240
gacaccgtga agggccggtt caccatctcc agagacaatt ccaagaacac gctgtatctg   300
caaatgaaca gcctgagagc cgaggacacg gccgtatatt actgtgcgag catgggggt    360
aactactggg actttgacgt ctggggccaa ggaaccctgg tcaccgtctc ctca         414

SEQ ID NO: 39          moltype = DNA   length = 414
FEATURE                Location/Qualifiers
misc_feature           1..414
                       note = Description of Artificial Sequence: Synthetic
                         polynucleotide
source                 1..414
                       mol_type = other DNA
                       organism = synthetic construct
SEQUENCE: 39
atggagtttg ggctgagctg gcttttcctt gtggctaaaa taaaaggtgt ccagtgtgag    60
gtgcagctgg tggagtctgg gggaggcttg gtacagcctg gggggtccct gagactctcc   120
tgtgcagcct ctggattcac ctttagcagc tattacagc gctgggtccg ccaggctcca    180
gggaaggggc tggagtgggt ctcagctatt aactccagcg gtggtagcac atactacgct   240
gactccgtga agggccggtt caccatctcc agagacaatt ccaagaacac gctgtatctg   300
caaatgaaca gcctgagagc cgaggacacg gccgtatatt actgtgcgag catgggggt    360
aactactggg actttgacgt ctggggccaa ggaaccctgg tcaccgtctc ctca         414
```

```
SEQ ID NO: 40            moltype = DNA  length = 414
FEATURE                  Location/Qualifiers
misc_feature             1..414
                         note = Description of Artificial Sequence: Synthetic
                         polynucleotide
source                   1..414
                         mol_type = other DNA
                         organism = synthetic construct
SEQUENCE: 40
atggagtttg ggctgagctg gcttttcctt gtggctaaaa taaaaggtgt ccagtgtgag    60
gtgcagctgg tggagtctgg gggaggcttg gtacagcctg ggggtccct gagactctcc    120
tgtgcagcct ctggattcac ctttagcagc tattacatga gctgggtccg ccaggctcca   180
gggaagggc tggagctggt cgcagctatt aactccagcg tggtagcac atactaccca    240
gactccgtga agggccggtt caccatctcc agagacaatt ccaagaacac gctgtatctg   300
caaatgaaca gcctgagagc cgaggacacg gccgtatatt actgtgcgag acatgggggt   360
aactactggt actttgacgt ctgggggccaa ggaaccctgg tcaccgtctc ctca         414

SEQ ID NO: 41            moltype = DNA  length = 723
FEATURE                  Location/Qualifiers
misc_feature             1..723
                         note = Description of Artificial Sequence: Synthetic
                         polynucleotide
source                   1..723
                         mol_type = other DNA
                         organism = synthetic construct
SEQUENCE: 41
atggagaccg acaccctgct gctctgggtg ctgctgctct gggtgcccgg ctccaccgga   60
gacatcgtga tgacccaaag ccccgactcc ctggcggtta gcctgggcga gagggccacg   120
atcaactgca gagcagcca gagcctgttg tacagcagca accagaagaa ctacctggcc   180
tggtatcagc agaagcctgg ccaaccccg aagctgctca tctactgggc cagcacccgg   240
gagagcggcg tgcccgacag gttcagcggc agtgggagcg gcaccgactt ccccctgacc   300
atcagctcct gcaggctga ggacgtggcc gtgtactact gccagcagta ctacagctac    360
ccctacacct tcggccaggg caccaaactg gagatcaagc ggaccgtggc cgcccccagc   420
gtgttcatct tccctcccag cgacgagcag ctgaagtctg gcaccgccag cgtggtgtgc   480
ctgctgaaca acttctaccc ccgcgaggcc aaggtcagt ggaaggtgga caacgccctg    540
cagagcggca acagccagga gagcgtgacc gagcaggact ccaaggacag cacctacagc   600
ctgagcagca ccctgaccct gagcaaggcc gactacgaga gcacaaggt gtacgcctgc   660
gaggtgaccc accagggact gtctagcccc gtgaccaaga gcttcaaccg gggcgagtgc   720
taa                                                                  723

SEQ ID NO: 42            moltype = DNA  length = 723
FEATURE                  Location/Qualifiers
misc_feature             1..723
                         note = Description of Artificial Sequence: Synthetic
                         polynucleotide
source                   1..723
                         mol_type = other DNA
                         organism = synthetic construct
SEQUENCE: 42
atggagaccg acaccctgct gctctgggtg ctgctgctct gggtgcccgg ctccaccgga   60
gacatcgtga tgacccaaag ccccgactcc ctggcggtta gcctgggcga gagggccacg   120
atcaactgca gagcagcca gagcctgttg tacagcagca accagaagaa ctacctggcc   180
tggtatcagc agaagcctgg ccaatccccg aagctgctca tctactgggc cagcacccgg   240
gagagcggcg tgcccgacag gttcagcggc agtgggagcg gcaccgactt ccccctgacc   300
atcagctcct gcaggctga ggacgtggcc gtgtactact gccagcagta ctacagctac    360
ccctacacct tcggccaggg caccaaactg gagatcaagc ggaccgtggc cgcccccagc   420
gtgttcatct tccctcccag cgacgagcag ctgaagtctg gcaccgccag cgtggtgtgc   480
ctgctgaaca acttctaccc ccgcgaggcc aaggtcagt ggaaggtgga caacgccctg    540
cagagcggca acagccagga gagcgtgacc gagcaggact ccaaggacag cacctacagc   600
ctgagcagca ccctgaccct gagcaaggcc gactacgaga gcacaaggt gtacgcctgc   660
gaggtgaccc accagggact gtctagcccc gtgaccaaga gcttcaaccg gggcgagtgc   720
taa                                                                  723

SEQ ID NO: 43            moltype = DNA  length = 723
FEATURE                  Location/Qualifiers
misc_feature             1..723
                         note = Description of Artificial Sequence: Synthetic
                         polynucleotide
source                   1..723
                         mol_type = other DNA
                         organism = synthetic construct
SEQUENCE: 43
atggagaccg acaccctgct gctctgggtg ctgctgctct gggtgcccgg ctccaccgga   60
gacatcgtga tgacccaaag ccccgactcc ctggcggtta gcctgggcga gagggccacg   120
atcaactgca gagcagcca gagcctgttg tacagcagca accagaagaa ctacctggcc   180
tggtatcagc agaagcctgg ccaatccccg aagctgctca tctactgggc cagcacccgg   240
gagagcggcg tgcccgacag gttcagcggc agtgggagcg gcaccgactt ccccctgacc   300
atcagctcct gcaggctga ggacgtggcc gtgtactact gccagcagta ctacagctac    360
ccctacacct tcggcggagg caccaaagtg gagatcaagc ggaccgtggc cgcccccagc   420
```

-continued

```
gtgttcatct tccctcccag cgacgagcag ctgaagtctg gcaccgccag cgtggtgtgc    480
ctgctgaaca acttctaccc ccgcgaggcc aaggtgcagt ggaaggtgga caacgccctg    540
cagagcggca acagccagga gagcgtgacc gagcaggact ccaaggacag cacctacagc    600
ctgagcagca ccctgaccct gagcaaggcc gactacgaga agcacaaggt gtacgcctgc    660
gaggtgaccc accagggact gtctagcccc gtgaccaaga gcttcaaccg gggcgagtgc    720
taa                                                                  723

SEQ ID NO: 44           moltype = DNA  length = 399
FEATURE                 Location/Qualifiers
misc_feature            1..399
                        note = Description of Artificial Sequence: Synthetic
                          polynucleotide
source                  1..399
                        mol_type = other DNA
                        organism = synthetic construct
SEQUENCE: 44
atggtgttgc agacccaggt cttcatttct ctgttgctct ggatctctgg tgcctacggg     60
gacatcgtga tgacccagtc tccagactcc ctggctgtgt ctctgggcga gagggccacc    120
atcaactgca agtccagcca gagtttgtta tacagctcca accagaagaa ctacttagct    180
tggtaccagc agaaaccagg acagcctcct aagctgctca tttactgggc atctacccgg    240
gaatccgggg tccctgaccg attcagtggc agcgggtctg gacagatttt cactctcacc    300
atcagcagcc tgcaggctga agatgtggca gtttattact gtcagcaata ttatagttac    360
ccttacactt ttggccaggg gaccaagctg gagatcaaa                           399

SEQ ID NO: 45           moltype = DNA  length = 399
FEATURE                 Location/Qualifiers
misc_feature            1..399
                        note = Description of Artificial Sequence: Synthetic
                          polynucleotide
source                  1..399
                        mol_type = other DNA
                        organism = synthetic construct
SEQUENCE: 45
atggtgttgc agacccaggt cttcatttct ctgttgctct ggatctctgg tgcctacggg     60
gacatcgtga tgtcccagtc tccagactcc ctggctgtgt ctctgggcga gagggccacc    120
atctcctgca agtccagcca gagtttgtta tacagctcca accagaagaa ctacttagct    180
tggtaccagc agaaaccagg acagcctcct aagctgctca tttactgggc atctacccgg    240
gaatccgggg tccctgaccg attcagtggc agcgggtctg gacagatttt cactctcacc    300
atcagcagcc tgcaggctga agatgtggca gtttattact gtcagcaata ttatagttac    360
ccttacactt ttggccaggg gaccaagctg gagatcaaa                           399

SEQ ID NO: 46           moltype = DNA  length = 414
FEATURE                 Location/Qualifiers
misc_feature            1..414
                        note = Description of Artificial Sequence: Synthetic
                          polynucleotide
source                  1..414
                        mol_type = other DNA
                        organism = synthetic construct
SEQUENCE: 46
atgaacttcg ggctcagatt gattttcctt gtccttgttt taaaaggtgt cctgtgcgac     60
gtgaagctcg tggagtctgg gggaggctta gtgaagcttg gagggtccct gaaactctcc    120
tgtgcagcct ctggattcac tttcagtagc tattacatgt cttgggttcg ccagactcca    180
gagaagaggc tggagttggt cgcagccatt aatagtaatg gtggtagcac ctactatcca    240
gacactgtga agggccgatt caccatctcc agagacaatc caagaacac cctgtacctg    300
caaatgagca gtctgaagtc tgaggacaca gccttgtatt actgtgcaag acatggggt    360
aactactggt acttcgatgt ctggggcgca gggaccacgg tcaccgtctc ctca          414

SEQ ID NO: 47           moltype = DNA  length = 357
FEATURE                 Location/Qualifiers
misc_feature            1..357
                        note = Description of Artificial Sequence: Synthetic
                          polynucleotide
source                  1..357
                        mol_type = other DNA
                        organism = synthetic construct
SEQUENCE: 47
gacgtgaagc tcgtggagtc tgggggaggc ttagtgaagc ttggagggtc cctgaaactc     60
tcctgtgcag cctctggatt cactttcagt agctattaca tgtcttgggt tcgccagact    120
ccagagaaga ggctggagtt ggtcgcagcc attaatagta atggtggtag cacctactat    180
ccagacactg tgaagggccg attcaccatc tccagagaca atgccaagaa caccctgtac    240
ctgcaaatga gcagtctgaa gtctgaggac acagccttgt attactgtgc aagacatggg    300
ggtaactact ggtacttcga tgtctggggc gcagggacca cggtcaccgt ctcctca       357

SEQ ID NO: 48           moltype = DNA  length = 399
FEATURE                 Location/Qualifiers
misc_feature            1..399
                        note = Description of Artificial Sequence: Synthetic
                          polynucleotide
```

```
source                  1..399
                        mol_type = other DNA
                        organism = synthetic construct
SEQUENCE: 48
atggattcac aggcccaggt tcttatgtta ctgctgctat gggtatctgg tacctgtggg    60
gacattgtga tgtcacagtc tccatcctcc ctagctgtgt cagttggaga gaaggttact   120
atgagctgca agtccagtca gagccttta tatagtagca atcaaaagaa ctacttggcc    180
tggtaccagc agaaaccagg gcagtctcct aaactgctga tttactgggc atccactagg   240
gaatctgggg tccctgatcg cttcacaggc agtggatctg gacagattt cactctcacc    300
atcagcagtg tgaaggctga agacctggca gtttattact gtcagcaata ttatagctat   360
ccgtacacgt tcggaggggg gaccaagctg gaaataaaa                          399

SEQ ID NO: 49           moltype = DNA  length = 339
FEATURE                 Location/Qualifiers
misc_feature            1..339
                        note = Description of Artificial Sequence: Synthetic
                        polynucleotide
source                  1..339
                        mol_type = other DNA
                        organism = synthetic construct
SEQUENCE: 49
gacattgtga tgtcacagtc tccatcctcc ctagctgtgt cagttggaga gaaggttact    60
atgagctgca agtccagtca gagccttta tatagtagca atcaaaagaa ctacttggcc    120
tggtaccagc agaaaccagg gcagtctcct aaactgctga tttactgggc atccactagg   180
gaatctgggg tccctgatcg cttcacaggc agtggatctg gacagattt cactctcacc    240
atcagcagtg tgaaggctga agacctggca gtttattact gtcagcaata ttatagctat   300
ccgtacacgt tcggaggggg gaccaagctg gaaataaaa                          339

SEQ ID NO: 50           moltype = AA  length = 729
FEATURE                 Location/Qualifiers
source                  1..729
                        mol_type = protein
                        organism = Homo sapiens
SEQUENCE: 50
MSFGRDMELE HFDERDKAQR YSRGSRVNGL PSPTHSAHCS FYRTRTLQTL SSEKKAKKVR     60
FYRNGDRYFK GIVYAISPDR FRSFEALLAD LTRTLSDNVN LPQGVRTIYT IDGLKKISSL   120
DQLVEGESYV CGSIEPFKKL EYTKNVNPNW SVNVKTTSAS RAVSSLATAK GSPSEVRENK   180
DFIRPKLVTI IRSGVKPRKA VRILLNKKTA HSFEQVLTDI TDAIKLDSGV VKRLYTLDGK   240
QVMCLQDFFG DDDIFIACGP EKFRYQDDFL LDESECRVVK STSYTKIASS SRRSTTKSPG   300
PSRRSKSPAS TSSVNGTPGS QLSTPRSGKS PSPSPTSPGS LRKQRSSQHG GSSTSLASTK   360
VCSSMDENDG PGEEVSEEGF QIPATITERY KVGRTIGDGN FAVVKECVER STAREYALKI   420
IKKSKCRGKE HMIQNEVSIL RRVKHPNIVL LIEEMDVPTE LYLVMELVKG GDLFDAITST   480
NKYTERDASG MLYNLASAIK YLHSLNIVHR DIKPENLLVY EHQDGSKSLK LGDFGLATIV   540
DGPLYTVCGT PTYVAPEIIA ETGYGLKVDI WAAGVITYIL LCGFPPFRGS GDDQEVLFDQ   600
ILMGQVDFPS PYWDNVSDSA KELITMMLLV DVDQRFSAVQ VLEHPWVNDD GLPENEHQLS   660
VAGKIKKHFN TGPKPNSTAA GVSVIALDHG FTIKRSGSLD YYQQPGMYWI RPPLLIRRGR   720
FSDEDATRM                                                           729

SEQ ID NO: 51           moltype = AA  length = 740
FEATURE                 Location/Qualifiers
source                  1..740
                        mol_type = protein
                        organism = Homo sapiens
SEQUENCE: 51
MSFGRDMELE HFDERDKAQR YSRGSRVNGL PSPTHSAHCS FYRTRTLQTL SSEKKAKKVR     60
FYRNGDRYFK GIVYAISPDR FRSFEALLAD LTRTLSDNVN LPQGVRTIYT IDGLKKISSL   120
DQLVEGESYV CGSIEPFKKL EYTKNVNPNW SVNVKTTSAS RAVSSLATAK GSPSEVRENK   180
DFIRPKLVTI IRSGVKPRKA VRILLNKKTA HSFEQVLTDI TDAIKLDSGV VKRLYTLDGK   240
QVMCLQDFFG DDDIFIACGP EKFRYQDDFL LDESECRVVK STSYTKIASS SRRSTTKSPG   300
PSRRSKSPAS TSSVNGTPGS QLSTPRSGKS PSPSPTSPGS LRKQRSSQHG GSSTSLASTK   360
VCSSMDENDG PGEEVSEEGF QIPATITERY KVGRTIGDGN FAVVKECVER STAREYALKI   420
IKKSKCRGKE HMIQNEVSIL RRVKHPNIVL LIEEMDVPTE LYLVMELVKG GDLFDAITST   480
NKYTERDASG MLYNLASAIK YLHSLNIVHR DIKPENLLVY EHQDGSKSLK LGDFGLATIV   540
DGPLYTVCGT PTYVAPEIIA ETGYGLKVDI WAAGVITYIL LCGFPPFRGS GDDQEVLFDQ   600
ILMGQVDFPS PYWDNVSDSA KELITMMLLV DVDQRFSAVQ VLEHPWVNDD GLPENEHQLS   660
VAGKIKKHFN TGPKPNSTAA GVSVIATTAL DKERQVFRRR RNQDVRSRYK AQPAPPELNS   720
ESEDYSPSSS ETVRSPNSPF                                               740

SEQ ID NO: 52           moltype = AA  length = 422
FEATURE                 Location/Qualifiers
source                  1..422
                        mol_type = protein
                        organism = Homo sapiens
SEQUENCE: 52
MLELIEVNGT PGSQLSTPRS GKSPSPSPTS PGSLRKQRSS QHGGSSTSLA STKVCSSMDE     60
NDGPGEEVSE EGFQIPATIT ERYKVGRTIG DGNFAVVKEC VERSTAREYA LKIIKKSKCR   120
GKEHMIQNEV SILRRVKHPN IVLLIEEMDV PTELYLVMEL VKGGDLFDAI TSTNKYTERD   180
ASGMLYNLAS AIKYLHSLNI VHRDIKPENL LVYEHQDGSK SLKLGDFGLA TIVDGPLYTV   240
CGTPTYVAPE IIAETGYGLK VDIWAAGVIT YILLCGFPPF RGSGDDQEVL FDQILMGQVD   300
```

```
FPSPYWDNVS DSAKELITMM LLVDVDQRFS AVQVLEHPWV NDDGLPENEH QLSVAGKIKK   360
HFNTGPKPNS TAAGVSVIAL DHGFTIKRSG SLDYYQQPGM YWIRPPLLIR RGRFSDEDAT   420
RM                                                                 422

SEQ ID NO: 53           moltype = AA  length = 433
FEATURE                 Location/Qualifiers
source                  1..433
                        mol_type = protein
                        organism = Homo sapiens
SEQUENCE: 53
MLELIEVNGT PGSQLSTPRS GKSPSPSPTS PGSLRKQRSS QHGGSSTSLA STKVCSSMDE   60
NDGPGEEVSE EGFQIPATIT ERYKVGRTIG DGNFAVVKEC VERSTAREYA LKIIKKSKCR   120
GKEHMIQNEV SILRRVKHPN IVLLIEEMDV PTELYLVMEL VKGGDLFDAI TSTNKYTERD   180
ASGMLYNLAS AIKYLHSLNI VHRDIKPENL LVYEHQDGSK SLKLGDFGLA TIVDGPLYTV   240
CGTPTYVAPE IIAETGYGLK VDIWAAGVIT YILLCGFPPF RGSGDDQEVL FDQILMGQVD   300
FPSPYWDNVS DSAKELITMM LLVDVDQRFS AVQVLEHPWV NDDGLPENEH QLSVAGKIKK   360
HFNTGPKPNS TAAGVSVIAT TALDKERQVF RRRRNQDVRS RYKAQPAPPE LNSESEDYSP   420
SSSETVRSPN SPF                                                     433

SEQ ID NO: 54           moltype = AA  length = 81
FEATURE                 Location/Qualifiers
source                  1..81
                        mol_type = protein
                        organism = Homo sapiens
SEQUENCE: 54
DDGLPENEHQ LSVAGKIKKH FNTGPKPNST AAGVSVIALD HGFTIKRSGS LDYYQQPGMY   60
WIRPPLLIRR GRFSDEDATR M                                            81

SEQ ID NO: 55           moltype = AA  length = 30
FEATURE                 Location/Qualifiers
source                  1..30
                        mol_type = protein
                        organism = Homo sapiens
SEQUENCE: 55
DYYQQPGMYW IRPPLLIRRG RFSDEDATRM                                   30

SEQ ID NO: 56           moltype = AA  length = 30
FEATURE                 Location/Qualifiers
source                  1..30
                        mol_type = protein
                        organism = Homo sapiens
SEQUENCE: 56
AGVSVIALDH GFTIKRSGSL DYYQQPGMYW                                   30

SEQ ID NO: 57           moltype = AA  length = 92
FEATURE                 Location/Qualifiers
source                  1..92
                        mol_type = protein
                        organism = Homo sapiens
SEQUENCE: 57
DDGLPENEHQ LSVAGKIKKH FNTGPKPNST AAGVSVIATT ALDKERQVFR RRRNQDVRSR   60
YKAQPAPPEL NSESEDYSPS SSETVRSPNS PF                                92

SEQ ID NO: 58           moltype = AA  length = 81
FEATURE                 Location/Qualifiers
source                  1..81
                        mol_type = protein
                        organism = Homo sapiens
SEQUENCE: 58
DDGLPENEHQ LSVAGKIKKH FNTGPKPNST AAGVSVIALD HGFTIKRSGS LDYYQQPGMY   60
WIRPPLLIRR GRFSDEDATR M                                            81

SEQ ID NO: 59           moltype = AA  length = 71
FEATURE                 Location/Qualifiers
source                  1..71
                        mol_type = protein
                        organism = Homo sapiens
SEQUENCE: 59
DDGLPENEHQ LSVAGKIKKH FNTGPKPNST AAGVSVIATT ALDKERQVFR RRRNQDVRSR   60
YKAQPAPPEL N                                                       71

SEQ ID NO: 60           moltype = AA  length = 384
FEATURE                 Location/Qualifiers
source                  1..384
                        mol_type = protein
                        organism = Homo sapiens
SEQUENCE: 60
APTKAPDVFP IISGCRHPKD NSPVVLACLI TGYHPTSVTV TWYMGTQSQP QRTFPEIQRR   60
DSYYMTSSQL STPLQQWRQG EYKCVVQHTA SKSKKEIFRW PESPKAQASS VPTAQPQAEG   120
```

```
SLAKATTAPA TTRNTGRGGE EKKKEKEKEE QEERETKTPE CPSHTQPLGV YLLTPAVQDL    180
WLRDKATFTC FVVGSDLKDA HLTWEVAGKV PTGGVEEGLL ERHSNGSQSQ HSRLTLPRSL    240
WNAGTSVTCT LNHPSLPPQR LMALREPAAQ APVKLSLNLL ASSDPPEAAS WLLCEVSGFS    300
PPNILLMWLE DQREVNTSGF APARPPPQPG STTFWAWSVL RVPAPPSPQP ATYTCVVSHE    360
DSRTLLNASR SLEVSYVTDH GPMK                                           384

SEQ ID NO: 61              moltype = AA  length = 330
FEATURE                    Location/Qualifiers
source                     1..330
                           mol_type = protein
                           organism = Homo sapiens
SEQUENCE: 61
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKKVEP KSCDKTHTCP PCPAPELLGG    120
PSVFLFPPKP KDTLMISRTP EVTCVVVDVS HEDPEVKFNW YVDGVEVHNA KTKPREEQYN    180
STYRVVSVLT VLHQDWLNGK EYKCKVSNKA LPAPIEKTIS KAKGQPREPQ VYTLPPSRDE    240
LTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                     330

SEQ ID NO: 62              moltype = AA  length = 326
FEATURE                    Location/Qualifiers
source                     1..326
                           mol_type = protein
                           organism = Homo sapiens
SEQUENCE: 62
ASTKGPSVFP LAPCSRSTSE STAALGCLVK DYFPEPVTVS WNSGALTSGV HTFPAVLQSS     60
GLYSLSSVVT VPSSNFGTQT YTCNVDHKPS NTKVDKTVER KCCVECPPCP APPVAGPSVF    120
LFPPKPKDTL MISRTPEVTC VVVDVSHEDP EVQFNWYVDG VEVHNAKTKP REEQFNSTFR    180
VVSVLTVVHQ DWLNGKEYKC KVSNKGLPAP IEKTISKTKG QPREPQVYTL PPSREEMTKN    240
QVSLTCLVKG FYPSDISVEW ESNGQPENNY KTTPPMLDSD GSFFLYSKLT VDKSRWQQGN    300
VFSCSVMHEA LHNHYTQKSL SLSPGK                                         326

SEQ ID NO: 63              moltype = AA  length = 377
FEATURE                    Location/Qualifiers
source                     1..377
                           mol_type = protein
                           organism = Homo sapiens
SEQUENCE: 63
ASTKGPSVFP LAPCSRSTSG GTAALGCLVK DYFPEPVTVS WNSGALTSGV HTFPAVLQSS     60
GLYSLSSVVT VPSSSLGTQT YTCNVNHKPS NTKVDKRVEL KTPLGDTTHT CPRCPEPKSC    120
DTPPPCPRCP EPKSCDTPPP CPRCPEPKSC DTPPPCPRCP APELLGGPSV FLFPPKPKDT    180
LMISRTPEVT CVVVDVSHED PEVQFKWYVD GVEVHNAKTK PREEQYNSTF RVVSVLTVLH    240
QDWLNGKEYK CKVSNKALPA PIEKTISKTK GQPREPQVYT LPPSREEMTK NQVSLTCLVK    300
GFYPSDIAVE WESSGQPENN YNTTPPMLDS DGSFFLYSKL TVDKSRWQQG NIFSCSVMHE    360
ALHNRFTQKS LSLSPGK                                                    377

SEQ ID NO: 64              moltype = AA  length = 452
FEATURE                    Location/Qualifiers
source                     1..452
                           mol_type = protein
                           organism = Homo sapiens
SEQUENCE: 64
GSASAPTLFP LVSCENSPSD TSSVAVGCLA QDFLPDSITL SWKYKNNSDI SSTRGFPSVL     60
RGGKYAATSQ VLLPSKDVMQ GTDEHVVCKV QHPNGNKEKN VPLPVIAELP PKVSVFPPR     120
DGFFGNPRKS KLICQATGFS PRQIQVSWLR EGKQVGSGVT TDQVQAEAKE SGPTTYKVTS    180
TLTIKESDWL GQSMFTCRVD HRGLTFQQNA SSMCVPDQDT AIRVFAIPPS FASIFLTKST    240
KLTCLVTDLT TYDSVTISWT RQNGEAVKTH TNISESHPNA TFSAVGEASI CEDDWNSGER    300
FTCTVTHTDL PSPLKQTISR PKGVALHRPD VYLLPPAREQ LNLRESATIT CLVTGFSPAD    360
VFVQWMQRGQ PLSPEKYVTS APMPEPQAPG RYFAHSILTV SEEEWNTGET YTCVAHEALP    420
NRVTERTVDK STGKPTLYNV SLVMSDTAGT CY                                   452

SEQ ID NO: 65              moltype = AA  length = 327
FEATURE                    Location/Qualifiers
source                     1..327
                           mol_type = protein
                           organism = Homo sapiens
SEQUENCE: 65
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327

SEQ ID NO: 66              moltype = AA  length = 353
FEATURE                    Location/Qualifiers
source                     1..353
                           mol_type = protein
                           organism = Homo sapiens
```

```
SEQUENCE: 66
ASPTSPKVFP LSLCSTQPDG NVVIACLVQG FFPQEPLSVT WSESGQGVTA RNFPPSQDAS    60
GDLYTTSSQL TLPATQCLAG KSVTCHVKHY TNPSQDVTVP CPVPSTPPTP SPSTPPTPSP   120
SCCHPRLSLH RPALEDLLLG SEANLTCTLT GLRDASGVTF TWTPSSGKSA VQGPPERDLC   180
GCYSVSSVLP GCAEPWNHGK TFTCTAAYPE SKTPLTATLS KSGNTFRPEV HLLPPPSEEL   240
ALNELVTLTC LARGFSPKDV LVRWLQGSQE LPREKYLTWA SRQEPSQGTT TFAVTSILRV   300
AAEDWKKGDT FSCMVGHEAL PLAFTQKTID RLAGKPTHVN VSVVMAEVDG TCY          353

SEQ ID NO: 67            moltype = AA   length = 340
FEATURE                  Location/Qualifiers
source                   1..340
                         mol_type = protein
                         organism = Homo sapiens
SEQUENCE: 67
ASPTSPKVFP LSLDSTPQDG NVVVACLVQG FFPQEPLSVT WSESGQNVTA RNFPPSQDAS    60
GDLYTTSSQL TLPATQCPDG KSVTCHVKHY TNPSQDVTVP CPVPPPPPCC HPRLSLHRPA   120
LEDLLLGSEA NLTCTLTGLR DASGATFTWT PSSGKSAVQG PPERDLCGCY SVSSVLPGCA   180
QPWNHGETFT CTAAHPELKT PLTANITKSG NTFRPEVHLL PPPSEELALN ELVTLTCLAR   240
GFSPKDVLVR WLQGSQELPR EKYLTWASRQ EPSQGTTTFA VTSILRVAAE DWKKGDTFSC   300
MVGHEALPLA FTQKTIDRMA GKPTHVNVSV VMAEVDGTCY                         340

SEQ ID NO: 68            moltype = AA   length = 106
FEATURE                  Location/Qualifiers
source                   1..106
                         mol_type = protein
                         organism = Homo sapiens
SEQUENCE: 68
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                  106

SEQ ID NO: 69            moltype = DNA   length = 48
FEATURE                  Location/Qualifiers
misc_feature             1..48
                         note = Description of Artificial Sequence: Synthetic
                           oligonucleotide
source                   1..48
                         mol_type = other DNA
                         organism = synthetic construct
SEQUENCE: 69
ctcgagccca atcttgtga caaaactcac acatgcccac cgtgcccg                  48

SEQ ID NO: 70            moltype = DNA   length = 81
FEATURE                  Location/Qualifiers
misc_feature             1..81
                         note = Description of Artificial Sequence: Synthetic
                           oligonucleotide
source                   1..81
                         mol_type = other DNA
                         organism = synthetic construct
SEQUENCE: 70
ttttgggtgc tggtggtggt tggtggagtc ctggcttgct atagcttgct agtaacagtg    60
gcctttatta ttttctgggt g                                              81

SEQ ID NO: 71            moltype = DNA   length = 126
FEATURE                  Location/Qualifiers
misc_feature             1..126
                         note = Description of Artificial Sequence: Synthetic
                           polynucleotide
source                   1..126
                         mol_type = other DNA
                         organism = synthetic construct
SEQUENCE: 71
aaacggggca gaaagaaact cctgtatata ttcaaacaac catttatgag accagtacaa    60
actactcaag aggaagatgg ctgtagctgc cgatttccaa agaagaaga aggaggatgt    120
gaactg                                                              126

SEQ ID NO: 72            moltype = DNA   length = 123
FEATURE                  Location/Qualifiers
misc_feature             1..123
                         note = Description of Artificial Sequence: Synthetic
                           polynucleotide
source                   1..123
                         mol_type = other DNA
                         organism = synthetic construct
SEQUENCE: 72
aggagtaaga ggagcaggct cctgcacagt gactacatga acatgactcc ccgccgcccc    60
gggcccaccc gcaagcatta ccagcccat gccccaccac gcgacttcgc agcctatcgc   120
tcc                                                                 123
```

| | | |
|---|---|---|
| SEQ ID NO: 73<br>FEATURE<br>misc_feature | moltype = DNA length = 339<br>Location/Qualifiers<br>1..339<br>note = Description of Artificial Sequence: Synthetic<br>polynucleotide | |
| source | 1..339<br>mol_type = other DNA<br>organism = synthetic construct | |
| SEQUENCE: 73 | | |
| agagtgaagt tcagcaggag cgcagacgcc cccgcgtacc agcagggcca gaaccagctc | | 60 |
| tataacgagc tcaatctagg acgaagagag gagtacgatg ttttggacaa gagacgtggc | | 120 |
| cgggaccctg agatgggggg aaagccgaga aggaagaacc ctcaggaagg cctgtacaat | | 180 |
| gaactgcaga aagataagat ggcggaggcc tacagtgaga ttgggatgaa aggcgagcgc | | 240 |
| cggagggggca aggggcacga tggcctttac cagggtctca gtacagccac caaggacacc | | 300 |
| tacgacgccc ttcacatgca ggccctgccc cctcgctaa | | 339 |
| SEQ ID NO: 74<br>FEATURE<br>source | moltype = AA length = 51<br>Location/Qualifiers<br>1..51<br>mol_type = protein<br>organism = Homo sapiens | |
| SEQUENCE: 74 | | |
| PAKPTTTPAP RPPTPAPTIA SQPLSLRPEA CRPAAGGAVH TRGLDFACDI Y | | 51 |
| SEQ ID NO: 75<br>FEATURE<br>source | moltype = AA length = 49<br>Location/Qualifiers<br>1..49<br>mol_type = protein<br>organism = Mus musculus | |
| SEQUENCE: 75 | | |
| KVNSTTTKPV LRTPSPVHPT GTSQPQRPED CRPRGSVKGT GLDFACDIY | | 49 |
| SEQ ID NO: 76<br>FEATURE<br>source | moltype = AA length = 51<br>Location/Qualifiers<br>1..51<br>mol_type = protein<br>organism = Felis catus | |
| SEQUENCE: 76 | | |
| PVKPTTTPAP RPPTQAPITT SQRVSLRPGT CQPSAGSTVE ASGLDLSCDI Y | | 51 |
| SEQ ID NO: 77<br>FEATURE<br>source | moltype = AA length = 21<br>Location/Qualifiers<br>1..21<br>mol_type = protein<br>organism = Homo sapiens | |
| SEQUENCE: 77 | | |
| IYIWAPLAGT CGVLLLSLVI T | | 21 |
| SEQ ID NO: 78<br>FEATURE<br>source | moltype = AA length = 21<br>Location/Qualifiers<br>1..21<br>mol_type = protein<br>organism = Mus musculus | |
| SEQUENCE: 78 | | |
| IWAPLAGICV ALLLSLIITL I | | 21 |
| SEQ ID NO: 79<br>FEATURE<br>source | moltype = AA length = 21<br>Location/Qualifiers<br>1..21<br>mol_type = protein<br>organism = Rattus norvegicus | |
| SEQUENCE: 79 | | |
| IWAPLAGICA VLLLSLVITL I | | 21 |
| SEQ ID NO: 80<br>FEATURE<br>REGION | moltype = AA length = 42<br>Location/Qualifiers<br>1..42<br>note = Description of Artificial Sequence: Synthetic<br>polypeptide | |
| source | 1..42<br>mol_type = protein<br>organism = synthetic construct | |
| SEQUENCE: 80 | | |
| KRGRKKLLYI FKQPFMRPVQ TTQEEDGCSC RFPEEEEGGC EL | | 42 |
| SEQ ID NO: 81<br>FEATURE<br>REGION | moltype = AA length = 220<br>Location/Qualifiers<br>1..220<br>note = Description of Artificial Sequence: Synthetic | |

```
                          polypeptide
source                    1..220
                          mol_type = protein
                          organism = synthetic construct
SEQUENCE: 81
MLRLLLALNL FPSIQVTGNK ILVKQSPMLV AYDNAVNLSC KYSYNLFSRE FRASLHKGLD    60
SAVEVCVVYG NYSQQLQVYS KTGFNCDGKL GNESVTFYLQ NLYVNQTDIY FCKIEVMYPP   120
PYLDNEKSNG TIIHVKGKHL CPSPLFPGPS KPFWVLVVVG GVLACYSLLV TVAFIIFWVR   180
SKRSRLLHSD YMNMTPRRPG PTRKHYQPYA PPRDFAAYRS                         220

SEQ ID NO: 82             moltype = DNA  length = 105
FEATURE                   Location/Qualifiers
misc_feature              1..105
                          note = Description of Artificial Sequence: Synthetic
                           polynucleotide
source                    1..105
                          mol_type = other DNA
                          organism = synthetic construct
SEQUENCE: 82
acaaaaaaga agtattcatc cagtgtgcac gaccctaacg gtgaatacat gttcatgaga    60
gcagtgaaca cagccaaaaa atccagactc acagatgtga cccta                  105

SEQ ID NO: 83             moltype = DNA  length = 108
FEATURE                   Location/Qualifiers
misc_feature              1..108
                          note = Description of Artificial Sequence: Synthetic
                           polynucleotide
source                    1..108
                          mol_type = other DNA
                          organism = synthetic construct
SEQUENCE: 83
agggaccaga ggctgccccc cgatgcccac aagcccctg ggggaggcag tttccggacc     60
cccatccaag aggagcaggc cgacgcccac tccaccctgg ccaagatc               108

SEQ ID NO: 84             moltype = AA  length = 112
FEATURE                   Location/Qualifiers
REGION                    1..112
                          note = Description of Artificial Sequence: Synthetic
                           polypeptide
source                    1..112
                          mol_type = protein
                          organism = synthetic construct
SEQUENCE: 84
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 85             moltype = AA  length = 8
FEATURE                   Location/Qualifiers
REGION                    1..8
                          note = Description of Artificial Sequence: Synthetic peptide
MOD_RES                   2
                          note = Val or Ile
MOD_RES                   4
                          note = Any amino acid
source                    1..8
                          mol_type = protein
                          organism = synthetic construct
SEQUENCE: 85
DXEXNPGP                                                             8

SEQ ID NO: 86             moltype = AA  length = 15
FEATURE                   Location/Qualifiers
REGION                    1..15
                          note = Description of Artificial Sequence: Synthetic peptide
source                    1..15
                          mol_type = protein
                          organism = synthetic construct
SEQUENCE: 86
GGGGSGGGGS GGGGS                                                    15

SEQ ID NO: 87             moltype = AA  length = 5
FEATURE                   Location/Qualifiers
REGION                    1..5
                          note = Description of Artificial Sequence: Synthetic peptide
source                    1..5
                          mol_type = protein
                          organism = synthetic construct
SEQUENCE: 87
GGGGS                                                                5
```

```
SEQ ID NO: 88              moltype = AA   length = 14
FEATURE                    Location/Qualifiers
REGION                     1..14
                           note = Description of Artificial Sequence: Synthetic peptide
source                     1..14
                           mol_type = protein
                           organism = synthetic construct
SEQUENCE: 88
GGGGSGGGGS GGGG                                                              14

SEQ ID NO: 89              moltype = AA   length = 13
FEATURE                    Location/Qualifiers
REGION                     1..13
                           note = Description of Artificial Sequence: Synthetic peptide
source                     1..13
                           mol_type = protein
                           organism = synthetic construct
SEQUENCE: 89
EFGAGLVLGG QFM                                                               13

SEQ ID NO: 90              moltype = AA   length = 30
FEATURE                    Location/Qualifiers
REGION                     1..30
                           note = Description of Artificial Sequence: Synthetic
                            polypeptide
REGION                     1..30
                           note = MISC_FEATURE - This sequence may encompass 1-6 'Gly
                            Gly Gly Gly Ser' repeating units
source                     1..30
                           mol_type = protein
                           organism = synthetic construct
SEQUENCE: 90
GGGGSGGGGS GGGGSGGGGS GGGGSGGGGS                                             30

SEQ ID NO: 91              moltype = AA   length = 119
FEATURE                    Location/Qualifiers
source                     1..119
                           mol_type = protein
                           organism = Mus musculus
SEQUENCE: 91
DVKLVESGGG LVKLGGSLKL SCAASGFTFS SYYMSWVRQT PEKRLELVAA INSNGGSTYY            60
PDTVKGRFTI SRDNAKNTLY LQMSSLKSED TALYYCARHG GNYWYFDVWG AGTTVTVSS            119

SEQ ID NO: 92              moltype = AA   length = 98
FEATURE                    Location/Qualifiers
source                     1..98
                           mol_type = protein
                           organism = Homo sapiens
SEQUENCE: 92
EVQLVESGGG LVQPGGSLRL SCAASGFTFS SYAMSWVRQA PGKGLEWVSA ISGSGGSTYY            60
ADSVKGRFTI SRDNSKNTLY LQMNSLRAED TAVYYCAK                                    98

SEQ ID NO: 93              moltype = AA   length = 113
FEATURE                    Location/Qualifiers
source                     1..113
                           mol_type = protein
                           organism = Mus musculus
SEQUENCE: 93
DIVMSQSPSS LAVSVGEKVT MSCKSSQSLL YSSNQKNYLA WYQQKPGQSP KLLIYWASTR            60
ESGVPDRFTG SGSGTDFTLT ISSVKAEDLA VYYCQQYYSY PYTFGGGTKL EIK                  113

SEQ ID NO: 94              moltype = AA   length = 101
FEATURE                    Location/Qualifiers
source                     1..101
                           mol_type = protein
                           organism = Homo sapiens
SEQUENCE: 94
DIVMTQSPDS LAVSLGERAT INCKSSQSVL YSSNNKNYLA WYQQKPGQPP KLLIYWASTR            60
ESGVPDRFSG SGSGTDFTLT ISSLQAEDVA VYYCQQYYST P                               101

SEQ ID NO: 95              moltype = AA   length = 21
FEATURE                    Location/Qualifiers
REGION                     1..21
                           note = Description of Artificial Sequence: Synthetic peptide
source                     1..21
                           mol_type = protein
                           organism = synthetic construct
SEQUENCE: 95
```

```
MALPVTALLL PLALLLHAAR P                                             21

SEQ ID NO: 96              moltype = AA   length = 8
FEATURE                    Location/Qualifiers
REGION                     1..8
                           note = Description of Artificial Sequence: Synthetic peptide
source                     1..8
                           mol_type = protein
                           organism = synthetic construct
SEQUENCE: 96
DYKDDDDK                                                            8

SEQ ID NO: 97              moltype = AA   length = 49
FEATURE                    Location/Qualifiers
REGION                     1..49
                           note = Description of Artificial Sequence: Synthetic
                            polypeptide
source                     1..49
                           mol_type = protein
                           organism = synthetic construct
SEQUENCE: 97
KPTTTPAPRP PTPAPTIASQ PLSLRPEASR PAAGGAVHTR GLDFASDKP               49

SEQ ID NO: 98              moltype = AA   length = 217
FEATURE                    Location/Qualifiers
REGION                     1..217
                           note = Description of Artificial Sequence: Synthetic
                            polypeptide
source                     1..217
                           mol_type = protein
                           organism = synthetic construct
SEQUENCE: 98
MLRLLLALNL FPSIQVTGNK ILVKQSPMLV AYDNAVNLSC KYSYNLFSRE FRASLHKGLD   60
SAVEVCVVYG NYSQQLQVYS KTGFNCDGKL GNESVTFYLQ NLYVNQTDIY FCKIEVMYPP   120
PYLDNEKSNG TIIHVGHLCP SPLFPGPSKP FWVLVWGGVL ACYSLLVTVA FIIFWVKSKR   180
SRLLHSDYMN MTPRRPGPTR KHYQPYAPPR DFAAYRS                            217

SEQ ID NO: 99              moltype = AA   length = 4
FEATURE                    Location/Qualifiers
REGION                     1..4
                           note = Description of Artificial Sequence: Synthetic peptide
source                     1..4
                           mol_type = protein
                           organism = synthetic construct
SEQUENCE: 99
YMNM                                                                4

SEQ ID NO: 100             moltype = AA   length = 4
FEATURE                    Location/Qualifiers
REGION                     1..4
                           note = Description of Artificial Sequence: Synthetic peptide
source                     1..4
                           mol_type = protein
                           organism = synthetic construct
SEQUENCE: 100
PYAP                                                                4

SEQ ID NO: 101             moltype = AA   length = 27
FEATURE                    Location/Qualifiers
REGION                     1..27
                           note = Description of Artificial Sequence: Synthetic peptide
source                     1..27
                           mol_type = protein
                           organism = synthetic construct
SEQUENCE: 101
FWVLVVVGGV LACYSLLVTV AFIIFWV                                       27

SEQ ID NO: 102             moltype = AA   length = 41
FEATURE                    Location/Qualifiers
REGION                     1..41
                           note = Description of Artificial Sequence: Synthetic
                            polypeptide
source                     1..41
                           mol_type = protein
                           organism = synthetic construct
SEQUENCE: 102
RSKRSRLLHS DYMNMTPRRP GPTRKHYQPY APPRDFAAYR S                       41

SEQ ID NO: 103             moltype = AA   length = 75
```

```
FEATURE            Location/Qualifiers
REGION             1..75
                   note = Description of Artificial Sequence: Synthetic
                    polypeptide
source             1..75
                   mol_type = protein
                   organism = synthetic construct
SEQUENCE: 103
FWVLVVVGGV LACYSLLVTV AFIIFWVRSK RSRLLHSDYM NMYMNMTPRR PGPTRKHYQY    60
APPYAPPRDF AAYRS                                                    75

SEQ ID NO: 104     moltype = AA  length = 75
FEATURE            Location/Qualifiers
REGION             1..75
                   note = Description of Artificial Sequence: Synthetic
                    polypeptide
source             1..75
                   mol_type = protein
                   organism = synthetic construct
SEQUENCE: 104
FWVLVVVGGV LACYSLLVTV AFIIFWVRSK RSRLLHSDYM NMYMNMPPRR PGPTRKHYQY    60
APPYAPPRDF AAYRS                                                    75

SEQ ID NO: 105     moltype = AA  length = 114
FEATURE            Location/Qualifiers
REGION             1..114
                   note = Description of Artificial Sequence: Synthetic
                    polypeptide
source             1..114
                   mol_type = protein
                   organism = synthetic construct
SEQUENCE: 105
RVKFSRSADA PAYQQGQNQL YNELNLGRRE EYDVLDKRRG RDPEMETGGK PRRKNPQEGL    60
YNELQKDKMA EAYSEIGMKG ERRRGKGHDG LYQGLSTATK DTYDALHMQA LPPR         114
```

ANTI-DCLK1 ANTIBODIES AND CHIMERIC ANTIGEN RECEPTORS, AND COMPOSITIONS AND METHODS OF USE THEREOF

CROSS-REFERENCE TO RELATED APPLICATIONS

This application is a continuation of U.S. application Ser. No. 16/769,567, filed Jun. 3, 2020; which is a national stage application filed under 35 U.S.C. § 371 of International Application No. PCT/US2018/063702, filed Dec. 3, 2018; which claims the benefit under 35 U.S.C. § 119(c) of U.S. Provisional Application No. 62/594,464, filed Dec. 4, 2017. The entire contents of each of the above-referenced patent applications are incorporated by reference into the present disclosure.

SEQUENCE LISTING

The instant application contains a Sequence Listing which has been submitted electronically in XML format and is hereby incorporated by reference in its entirety. Said XML copy, created on Jan. 29, 2024, is named "5864. 168 Sequence Listing. XML" and is 149,113 bytes in size.

TECHNICAL FIELD

This disclosure relates to humanized anti-DCLK1 antibodies and chimeric antigen receptor (CAR) cells and compositions comprising the same, and methods for using them for therapy including the treatment of solid tumors. Also provided herein are isolated peptides and fusion proteins containing immunogenic determinants for DCLK1.

BACKGROUND

The following discussion of the background of the disclosure is merely provided to aid the reader in the understanding the disclosure and is not admitted to describe or constitute prior art to the present disclosure.

Solid tumors, such as those in colon, rectal, intestinal, gastric, and pancreatic cancers, vary from being easily treatable to highly malignant. Biomarkers and symptoms can be used as prognostic indicators—for example, in colon cancer, elevated pretreatment serum levels of carcinoembryonic antigen (CEA) and/or carbohydrate antigen 19-9 (CA 19-9) correspond to negative prognosis; in intestinal cancer, Musashi-1 (Msi-1) may serve as a marker of intestinal tumors. Further, markers of particular cell lineages associated with the origin of the cancer can be used to detect circulating tumor cells. See U.S. Pat. No. 9,663,585 (discussing further details of these cancers in the Background section).

While great strides have been made in detecting cancer, there remains a need for safe and effective treatment of cancer. This disclosure satisfies this need and provides related advantages as well.

DETAILED DESCRIPTION

Figure 1:
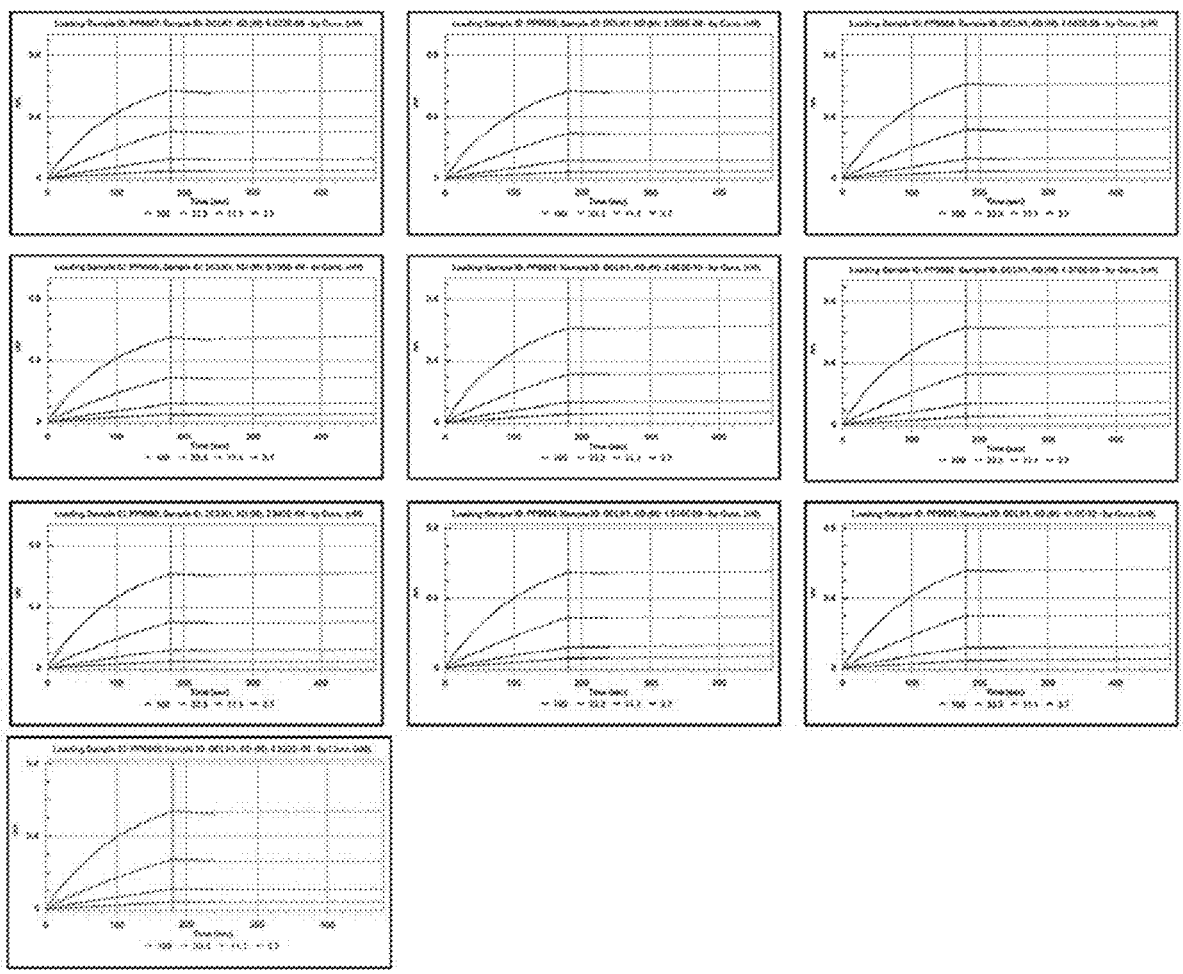
FIG. 1 depicts sensorgrams of anti-DCKL1 humanized antibodies.

Due to the unprecedented results being recently obtained in B-cell lymphomas and leukemias using autologous treatment with genetically engineered chimeric antigen receptor (CAR) T-cells, a number of laboratories have begun to apply this approach to solid tumors. CAR modified cells combine the HLA-independent targeting specificity of a monoclonal antibody with the cytolytic activity, proliferation, and homing properties of activated T-cells, but do not respond to checkpoint suppression. Because of their ability to kill antigen expressing targets directly, CAR cells are highly toxic to any antigen positive cells or tissues making it a requirement to construct CARs with highly specific antibodies. Thus, in one aspect this disclosure provides DCLK1 as a target for the treatment of cancer. DCLK1 is often expressed on tumor cells. Thus, in one aspect, the compositions are particularly useful in the treatment of solid tumors or corresponding circulating cancer cells that express or overexpress DCLK1. In one aspect, disclosed herein are novel DCLK1 antibodies and methods of their use diagnostically and therapeutically. In this regard, provide herein is an isolated antibody comprising, or consisting essentially of, or yet further consisting of a heavy chain (HC) immunoglobulin variable domain sequence and a light chain (LC) immunoglobulin variable domain sequence, wherein the antibody binds to an isoform of DCLK1.

In one aspect, the present disclosure provides isolated, humanized antibodies, the antibodies comprising, or consisting essentially of, or yet further consisting of a heavy chain (HC) immunoglobulin variable domain sequence and a light chain (LC) immunoglobulin variable domain sequence, wherein the antibody binds to an epitope of DCLK1. In a further aspect, this disclosure provides isolated anti-DCLK1 antibodies or fragments thereof as disclosed herein and a detectable or purification label, alone or in combination with an DCLK1 antigen or fragment thereof. Further provided herein is an ex vivo cell comprising, or consisting essentially of, or yet further consisting of this antigen/antibody complex.

In some aspect, the humanized heavy chain (HC) immunoglobulin variable domain sequence comprises or alternatively consists essentially of, or yet further consists of one or more of the following amino acids sequences: SEQ ID Nos: 1-9 or 16-24 or an equivalent of each thereof.

In another aspect, the heavy chain (HC) immunoglobulin variable domain sequence comprises or alternatively consists essentially of, or yet further consists of one or more amino acid sequence encoded by the following nucleic acid sequences: SEQ ID Nos: 32-40 or an equivalent of each thereof.

In a further aspect, the light chain (LC) immunoglobulin variable domain sequence comprises or alternatively consists essentially of, or yet further consists of one or more of one or more of the following amino acids sequences: SEQ ID Nos: 11-14 or 26-30 or an equivalent of each thereof.

In a yet further aspect, the light chain (LC) immunoglobulin variable domain sequence comprises or alternatively consists essentially of, or yet further consists of one or more of one or more amino acid sequence encoded by the following nucleic acid sequences: SEQ ID Nos:41-45 or an equivalent of each thereof.

Also provided herein are the heavy chain (HC) immunoglobulin variable domain sequence and the light chain (LC) immunoglobulin variable domain sequence, which are humanized from a murine antibody sequence. In one aspect, the heavy chain (HC) immunoglobulin variable domain sequence of the humanized murine antibody comprises or alternatively consists essentially of, or yet further consists of one or more of the following amino acid sequences: SEQ ID Nos: 10 or 25 or an equivalent of each thereof and/or a sequence encoded by one or more of the following nucleic acid sequences: SEQ ID Nos: 46 or 47 or an equivalent of each thereof.

In another aspect, the light chain (LC) immunoglobulin variable domain sequence of the humanized murine antibody comprises or alternatively consists essentially of, or yet further consists of one or more of the following amino acid sequences: SEQ ID Nos: 15 or 31 or an equivalent of each thereof and/or a sequence encoded by one or more of the following nucleic acid sequences: SEQ ID Nos: 48 or 49 or an equivalent of each thereof.

Aspects of the disclosure relate to a chimeric antigen receptor (CAR) comprising, or consisting essentially of, or yet further consisting of: (a) an antigen binding domain of an anti-DCLK1 antibody; (b) a hinge domain; (c) a transmembrane domain; and (d) an intracellular domain.

Further aspects of the disclosure relate to a chimeric antigen receptor (CAR) comprising, or consisting essentially of, or yet further consisting of: (a) an antigen binding domain of an anti-DCLK1 antibody; (b) a hinge domain; (c) a CD28 transmembrane domain; (d) one or more costimulatory regions selected from a CD28 costimulatory signaling region, a 4-1BB costimulatory signaling region, an ICOS costimulatory signaling region, and an OX40 costimulatory region; and (e) a CD3 zeta signaling domain and alternatives thereof. In a yet further aspect, the present disclosure provides a chimeric antigen receptor (CAR) comprising, or consisting essentially of, or yet further consisting of: (a) an antigen binding domain of an anti-DCLK1 antibody, (b) a CD8 α or an IgG1 hinge domain; (c) a CD8 α transmembrane domain; (d) a CD28 and/or a 4-1BB costimulatory signaling region; and (e) a CD3 zeta signaling domain and alternatives thereof.

Further provided herein is an isolated nucleic acid sequence encoding the heavy chain (HC) immunoglobulin variable domain amino acid sequence comprising, or consisting essentially of, or yet further consisting of a sequence selected from the group of SEQ ID Nos: 1-10 or 16-25 of the humanized anti-DCLK1 antibody, or an equivalent of each thereof. In a further aspect, the present disclosure provides an isolated nucleic acid sequence encoding the light chain (LC) immunoglobulin variable domain amino acid sequence comprising, or consisting essentially of, or yet further consisting of a sequence selected from the group of SEQ ID Nos: 11-15 or 26-31 of the humanized anti-DCLK1 antibody, or an equivalent of each thereof. In another aspect, the present disclosure provides an isolated nucleic acid sequence encoding the anti-DCLK1 antibody, or the anti-DCLK1 CAR construct.

Also provided herein is a vector comprising, or consisting essentially of, or yet further consisting of the isolated nucleic acid sequence encoding the anti-DCLK1 antibody, or the anti-DCLK1 CAR construct. In one aspect, the present disclosure provides a vector comprising, or consisting essentially of, or yet further consisting of the isolated nucleic acid sequence encoding the anti-DCLK1 antibody, or the anti-DCLK1 CAR construct.

In another aspect, the present disclosure provides a composition comprising, or consisting essentially of, or yet further consisting of a carrier and one or more of: the anti-DCLK1 antibody; and/or the anti-DCLK1 CAR; and/or the isolated nucleic acid encoding the anti-DCLK1 antibody or the anti-DCLK1 CAR; and/or the vector comprising, or consisting essentially of, or yet further consisting of the isolated nucleic acid sequence encoding the anti-DCLK1 antibody, or the anti-DCLK1; and/or an isolated cell comprising, or consisting essentially of, or yet further consisting of the anti-DCLK1 construct.

Other aspects of the disclosure relate to an isolated cell comprising, or consisting essentially of, or yet further consisting of an anti-DCLK1 CAR and methods of producing such cells. Still other method aspects of the disclosure relate to methods of producing the anti-DCLK1 antibody and methods of inhibiting the growth of cancer cells or a tumor, e.g., a solid tumor, and treating a cancer patient cell by a method comprising, or consisting essentially of, or yet further consisting of administering an effective amount of the isolated cell.

In one aspect, the disclosure provides a composition comprising, or alternatively consisting essentially of, or yet further consisting of a carrier and one or more of: an antibody or fragment thereof, a nucleic acid encoding the antibody or fragment thereof, an isolated cell comprising, or consisting essentially of, or yet further consisting of an anti-DCLK1 CAR; and/or the isolated nucleic acid encoding the CAR; and/or the vector comprising, or consisting essentially of, or yet further consisting of the nucleic acid encoding the CAR; and/or the isolated cell expressing an anti-DCLK1 CAR; and/or the anti-DCLK1 antibody.

Also provided herein are kits containing the materials for making and using the anti-DCLK1 antibodies or the anti-DCLK1 CAR cells.

Definitions

It is to be understood that the present disclosure is not limited to particular aspects described, as such may, of course, vary. It is also to be understood that the terminology used herein is for the purpose of describing particular aspects only, and is not intended to be limiting, since the scope of the present disclosure will be limited only by the appended claims.

Unless defined otherwise, all technical and scientific terms used herein have the same meanings as commonly understood by one of ordinary skill in the art to which this technology belongs. Although any methods and materials similar or equivalent to those described herein can be used in the practice or testing of the present technology, the particular methods, devices, and materials are now described. All technical and patent publications cited herein are incorporated herein by reference in their entirety. Nothing herein is to be construed as an admission that the present technology is not entitled to antedate such disclosure by virtue of prior disclosure.

The practice of the present technology will employ, unless otherwise indicated, conventional techniques of tissue culture, immunology, molecular biology, microbiology, cell biology, and recombinant DNA, which are within the skill of the art. See, e.g., Sambrook and Russell eds. (2001) Molecular Cloning: A Laboratory Manual, 3rd edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5th edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and Walker eds. (1987) Immunochemical Methods in Cell and Molecular Biology (Academic Press, London); and Herzenberg et al. eds (1996) Weir's Handbook of Experimental Immunology.

All numerical designations, e.g., pH, temperature, time, concentration, and molecular weight, including ranges, are approximations which are varied (+) or (−) by increments of 1.0 or 0.1, as appropriate, or alternatively by a variation of +/−15%, or alternatively 10%, or alternatively 5%, or alternatively 2%. It is to be understood, although not always explicitly stated, that all numerical designations are preceded by the term "about". It also is to be understood, although not always explicitly stated, that the reagents described herein are merely exemplary and that equivalents of such are known in the art.

It is to be inferred without explicit recitation and unless otherwise intended, that when the present technology relates to a polypeptide, protein, polynucleotide or antibody, an equivalent or a biologically equivalent of such is intended within the scope of the present technology.

As used in the specification and claims, the singular form "a", "an", and "the" include plural references unless the context clearly dictates otherwise. For example, the term "a cell" includes a plurality of cells, including mixtures thereof.

As used herein, the term "comprising" is intended to mean that the compositions and methods include the recited elements, but do not exclude others. "Consisting essentially of" when used to define compositions and methods, shall mean excluding other elements of any essential significance to the combination for the intended use. For example, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions disclosed herein. Aspects defined by each of these transition terms are within the scope of the present disclosure.

As used herein, the term "animal" refers to living multicellular vertebrate organisms, a category that includes, for example, mammals and birds. The term "mammal" includes both human and non-human mammals.

The term "subject," "host," "individual," and "patient" are as used interchangeably herein to refer to animals, typically mammalian animals. Any suitable mammal can be treated by a method, cell or composition described herein. Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In some embodiments a mammal is a human. A mammal can be any age or at any stage of development (e.g., an adult, teen, child, infant, or a mammal in utero). A mammal can be male or female. A mammal can be a pregnant female. In some embodiments a subject is a human. In some embodiments, a subject has or is suspected of having a cancer or neoplastic disorder.

"Eukaryotic cells" comprise all of the life kingdoms except monera. They can be easily distinguished through a membrane-bound nucleus. Animals, plants, fungi, and protists are eukaryotes or organisms whose cells are organized into complex structures by internal membranes and a cytoskeleton. The most characteristic membrane-bound structure is the nucleus. Unless specifically recited, the term "host" includes a eukaryotic host, including, for example, yeast, higher plant, insect and mammalian cells. Non-limiting examples of eukaryotic cells or hosts include simian, bovine, porcine, murine, rat, avian, reptilian and human.

As used herein "a population of cells" intends a collection of more than one cell that is identical (clonal) or non-identical in phenotype and/or genotype.

As used herein, "substantially homogenous" population of cells is a population having at least 70%, or alternatively at least 75%, or alternatively at least 80%, or alternatively at least 85%, or alternatively at least 90%, or alternatively at least 95%, or alternatively at least 98% identical phenotype, as measured by pre-selected markers, phenotypic or genomic traits. In one aspect, the population is a clonal population.

As used herein, "heterogeneous" population of cells is a population having up to 69%, or alternatively up to 60%, or alternatively up to 50%, or alternatively up to 40%, or alternatively up to 30%, or alternatively up to 20%, or alternatively up to 10%, or alternatively up to 5%, or alternatively up to 4%, or alternatively up to 3%, or alternatively up to 2%, or alternatively up to 61%, or alternatively up to 0.5% identical phenotype, as measured by pre-selected markers, phenotypic or genomic traits.

As used herein, the term "antibody" collectively refers to immunoglobulins or immunoglobulin-like molecules including by way of example and without limitation, IgA, IgD, IgE, IgG and IgM, combinations thereof, and similar molecules produced during an immune response in any vertebrate, for example, in mammals such as humans, goats, rabbits and mice, as well as non-mammalian species, such as shark immunoglobulins. Unless specifically noted otherwise, the term "antibody" includes intact immunoglobulins and "antibody fragments" or "antigen binding fragments" that specifically bind to a molecule of interest (or a group of highly similar molecules of interest) to the substantial exclusion of binding to other molecules (for example, antibodies and antibody fragments that have a binding constant for the molecule of interest that is at least $10^3$ $M^{-1}$ greater, at least $10^4$ $M^{-1}$ greater or at least $10^5$ $M^{-1}$ greater than a binding constant for other molecules in a biological sample). In certain aspects, antibodies bind with affinities of less than or about $10^{-6}$ M, or alternatively less than about $10^{-7}$ M, or alternatively less than or about $10^{-8}$ M, or alternatively less than or about $10^{-9}$ M, or alternatively less than or about $10^{-10}$ M, or alternatively less than or about $10^{-11}$ M, or alternatively less than or about $10^{-12}$ M.

The term "antibody" also includes genetically engineered forms such as chimeric antibodies (for example, humanized murine antibodies), heteroconjugate antibodies (such as, bispecific antibodies). See also, Pierce Catalog and Handbook, 1994-1995 (Pierce Chemical Co., Rockford, Ill.); Kuby, J., Immunology, 3rd Ed., W.H. Freeman & Co., New York, 1997. An "antigen binding fragment" of an antibody is a portion of an antibody that retains the ability to specifically bind to the target antigen of the antibody.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies and human antibodies.

In terms of antibody structure, an immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE. Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, largely adopts a p-sheet conformation and the CDRs form loops which connect, and in some cases form part of, the j-sheet structure. Thus, framework regions act to form a scaffold that provides for positioning the CDRs in correct orientation by inter-chain, non-covalent interactions.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds DCLK1 will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding.

These positions within the CDRs are called specificity determining residues (SDRs).

The term "humanized" when used in reference to an antibody, means that the amino acid sequence of the antibody has non-human amino acid residues (e.g., mouse, rat, goat, rabbit, etc.) of one or more complementarity determining regions (CDRs) that specifically bind to the desired antigen in an acceptor human immunoglobulin molecule, and one or more human amino acid residues in the Fv framework region (FR), which are amino acid residues that flank the CDRs. Such antibodies typically have reduced immunogenicity and therefore a longer half-life in humans as compared to the non-human parent antibody from which one or more CDRs were obtained or are based upon.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, and proteins. Common categories of antigens include, but are not limited to, viral antigens, bacterial antigens, fungal antigens, protozoa and other parasitic antigens, tumor antigens, antigens involved in autoimmune disease, allergy and graft rejection, toxins, and other miscellaneous antigens.

As used herein, the term "antigen binding domain" refers to any protein or polypeptide domain that can specifically bind to an antigen target.

In the context of a nucleic acid or amino acid sequence, the term "chimeric" intends that the sequence contains is comprised of at least one substituent unit (e.g. fragment, region, portion, domain, polynucleotide, or polypeptide) that is derived from, obtained or isolated from, or based upon other distinct physical or chemical entities. For example, a chimera of two or more different proteins may comprise the sequence of a variable region domain from an antibody fused to the transmembrane domain of a cell signaling molecule. In some aspect, a chimera intends that the sequence is comprised of sequences from at least two distinct species. The term "chimeric antigen receptor" (CAR), as used herein, refers to a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell. In certain embodiments, the intracellular domain may comprise, alternatively consist essentially of, or yet further comprise one or more costimulatory signaling domains in addition to the primary signaling domain. The "transmembrane domain" means any oligopeptide or polypeptide known to span the cell membrane and that can function to link the extracellular and signaling domains. A chimeric antigen receptor may optionally comprise a "hinge domain" which serves as a linker between the extracellular and transmembrane domains. Non-limiting exemplary polynucleotide sequences that encode for components of each domain are disclosed herein, e.g.:

```
Hinge domain: IgG1 heavy chain hinge sequence:
                                         (SEQ ID NO: 69)
CTCGAGCCCAAATCTTGTGACAAAACTCACACATGCCCACCGTGCCCG Transmembrane domain: CD28 transmembrane region:
                                         (SEQ ID NO: 70)
TTTTGGGTGCTGGTGGTGGTTGGTGGAGTCCTGGCTTGCTATAGCTTGC

TAGTAACAGTGGCCTTTATTATTTTCTGGGTG

Intracellular domain: 4-1BB co-stimulatory
signaling region:
                                         (SEQ ID NO: 71)
AAACGGGGCAGAAAGAAACTCCTGTATATATTCAAACAACCATTTATGA

GACCAGTACAAACTACTCAAGAGGAAGATGGCTGTAGCTGCCGATTTCC

AGAAGAAGAAGAAGGAGGATGTGAACTG

Intracellular domain: CD28 co-stimulatory
signaling region:
                                         (SEQ ID NO: 72)
AGGAGTAAGAGGAGCAGGCTCCTGCACAGTGACTACATGAACATGACTC

CCCGCCGCCCCGGGCCCACCCGCAAGCATTACCAGCCCTATGCCCCACC

ACGCGACTTCGCAGCCTATCGCTCC

Intracellular domain: CD3 zeta signaling region:
                                         (SEQ ID NO: 73)
AGAGTGAAGTTCAGCAGGAGCGCAGACGCCCCCGCGTACCAGCAGGGCC

AGAACCAGCTCTATAACGAGCTCAATCTAGGACGAAGAGAGGAGTACGA

TGTTTTGGACAAGAGACGTGGCCGGGACCCTGAGATGGGGGGAAAGCCG

AGAAGGAAGAACCCTCAGGAAGGCCTGTACAATGAACTGCAGAAAGATA

AGATGGCGGAGGCCTACAGTGAGATTGGGATGAAAGGCGAGCGCCGGAG

GGGCAAGGGGCACGATGGCCTTTACCAGGGTCTCAGTACAGCCACCAAG

GACACCTACGACGCCCTTCACATGCAGGCCCTGCCCCCTCGCTAA
```

Further embodiments of each exemplary domain component include other proteins that have analogous biological function that share at least 70%, or alternatively at least 80% amino acid sequence identity, such as (but not limited to) 90% sequence identity, or at least 95% sequence identity with the proteins encoded by the above disclosed nucleic acid sequences.

Further, non-limiting examples of such domains are provided herein.

As used herein, the term "DCLK1" refers to doublecortin and Ca2+/calmodulin-dependent kinase-like-1 protein associated with this name and any other molecules that have analogous biological function that share at least 80% amino acid sequence identity, such as (but not limited to) 90% sequence identity, or alternatively at least 95% sequence identity with any DCLK1 variant, including but not limited to any one of its several variants, including but not limited to isoforms 1 through 4. Examples of the DCLK1 sequences are known in the art and non-limited examples of such are disclosed in various genetic databases, including but not limited to those found under reference numbers GeneCards Ref. No.: GC13M035768; HGNC Ref. No: 2700; Entrez Gene Ref. No.: 9201, Ensembl Ref. No.: ENSG00000133083, OMIM Ref. No.: 604742; and UniProtKB Ref. No.: O15075. Non-limiting exemplary sequences of each of isoforms 1-4 are provided below: SEQ ID NOs: 50-53 as well as equivalents of each thereof. The sequences associated with each of the listed reference(s) and GenBank Accession Numbers that correspond to the name DCLK1 or its equivalents including but not limited to the specified DCLK1 subtypes are herein incorporated by reference as additional non-limiting examples.

As used herein, a "first generation CAR" refers to a CAR comprising an extracellular domain capable of binding to an antigen, a transmembrane domain derived from a polypeptide different from a polypeptide from which the extracellular domain is derived, and at least one intracellular domain. A "second generation CAR" refers to a first generation CAR further comprising one co-stimulation domain (e.g. 4-1BB or CD28). A "third generation CAR" refers to a first generation CAR further comprising two co-stimulation domains (e.g. CD27, CD28, ICOS, 4-1BB, or OX40). A "fourth generation CAR" (also known as a "TRUCK") refers to a CAR T-cell further engineered to secrete an additional factor (e.g. proinflammatory cytokine IL-12). A review of these CAR technologies and cell therapy is found in Maus, M. et al. Clin. Cancer Res. 22(3): 1875-84 (2016).

As used herein, the term "signal peptide" or "signal polypeptide" intends an amino acid sequence usually present at the N-terminal end of newly synthesized secretory or membrane polypeptides or proteins. It acts to direct the polypeptide across or into a cell membrane and is then subsequently removed. Examples of such are well known in the art. Non-limiting examples are those described in U.S. Pat. Nos. 8,853,381 and 5,958,736.

As used herein in reference to a regulatory polynucleotide, the term "operatively linked" refers to an association between the regulatory polynucleotide and the polynucleotide sequence to which it is linked such that, when a specific protein binds to the regulatory polynucleotide, the linked polynucleotide is transcribed.

A "composition" typically intends a combination of the active agent, e.g., a CAR T cell or a CAR NK cell, an antibody, a compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers. Carriers also include pharmaceutical excipients and additives proteins, peptides, amino acids, lipids, and carbohydrates (e.g., sugars, including monosaccharides, di-, tri-, tetra-oligosaccharides, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, arginine, glycine, arginine, betaine, histidine, glutamic acid, aspartic acid, cysteine, lysine, leucine, isoleucine, valine, methionine, phenylalanine, aspartame, and the like. Carbohydrate excipients are also intended within the scope of this technology, examples of which include but are not limited to monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol) and myoinositol.

The compositions used in accordance with the disclosure, including cells, treatments, therapies, agents, drugs and pharmaceutical formulations can be packaged in dosage unit form for ease of administration and uniformity of dosage.

The term "unit dose" or "dosage" refers to physically discrete units suitable for use in a subject, each unit containing a predetermined quantity of the composition calculated to produce the desired responses in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described herein.

The term "consensus sequence" as used herein refers to an amino acid or nucleic acid sequence that is determined by aligning a series of multiple sequences and that defines an idealized sequence that represents the predominant choice of amino acid or base at each corresponding position of the multiple sequences. Depending on the sequences of the series of multiple sequences, the consensus sequence for the series can differ from each of the sequences by zero, one, a few, or more substitutions. Also, depending on the sequences of the series of multiple sequences, more than one consensus sequence may be determined for the series. The generation of consensus sequences has been subjected to intensive mathematical analysis. Various software programs can be used to determine a consensus sequence.

As used herein, the term "CD8 α hinge domain" refers to a specific protein fragment associated with this name and any other molecules that have analogous biological function that share at least 70%, or alternatively at least 80% amino acid sequence identity, such as (but not limited to) 90% sequence identity, or at least 95% sequence identity with the CD8 α hinge domain sequence as shown herein. The example sequences of CD8 α hinge domain for human, mouse, and other species are provided in Pinto, R. D. et al. (2006) Vet. Immunol. Immunopathol. 110:169-177. Non-limiting examples of such include:

```
Human CD8 alpha hinge domain:
                                    (SEQ ID NO: 74)
PAKPTTTPAPRPPTPAPTIASQPLSLRPEACRPAAGGAVHTRGLDFACD
IY Mouse CD8 alpha hinge domain:
                                    (SEQ ID NO: 75)
KVNSTTTKPVLRTPSPVHPTGTSQPQRPEDCRPRGSVKGTGLDFACDIY Cat CD8 alpha hinge domain:
                                    (SEQ ID NO: 76)
PVKPTTTPAPRPPTQAPITTSQRVSLRPGTCQPSAGSTVEASGLDLSCD
IY
```

As used herein, the term "CD8 α transmembrane domain" refers to a specific protein fragment associated with this name and any other molecules that have analogous biological function that share at least 70%, or alternatively at least 80% amino acid sequence identity, such as (but not limited to) 90% sequence identity, or at least 95% sequence identity with the CD8 α transmembrane domain sequence as shown herein. The fragment sequences associated with the amino acid positions 183 to 203 of the human T-cell surface glycoprotein CD8 alpha chain (NCBI Reference Sequence:

NP_001759.3), or the amino acid positions 197 to 217 of the mouse T-cell surface glycoprotein CD8 alpha chain (NCBI Reference Sequence: NP_001074579.1), and the amino acid positions 190 to 210 of the rat T-cell surface glycoprotein CD8 alpha chain (NCBI Reference Sequence: NP_113726.1) provide additional example sequences of the CD8 α transmembrane domain. The sequences associated with each of the listed NCBI are provided as follows:

```
Human CD8 alpha transmembrane domain:
                                        (SEQ ID NO: 77)
IYIWAPLAGTCGVLLLSLVIT Mouse CD8 alpha transmembrane domain:
                                        (SEQ ID NO: 78)
IWAPLAGICVALLLSLIITLI Rat CD8 alpha transmembrane domain:
                                        (SEQ ID NO: 79)
IWAPLAGICAVLLLSLVITLI
```

As used herein, the term "CD28 transmembrane domain" refers to a specific protein fragment associated with this name and any other molecules that have analogous biological function that share at least 70%, or alternatively at least 80% amino acid sequence identity, at least 90% sequence identity, or alternatively at least 95% sequence identity with the CD28 transmembrane domain sequence as shown herein. The fragment sequences associated with the GenBank Accession Nos: XM_006712862.2 and XM_009444056.1 provide additional, non-limiting, example sequences of the CD28 transmembrane domain. The sequences associated with each of the listed accession numbers are incorporated herein.

As used herein, the term "4-1BB costimulatory signaling region" refers to a specific protein fragment associated with this name and any other molecules that have analogous biological function that share at least 70%, or alternatively at least 80% amino acid sequence identity, such as (but not limited to) 90% sequence identity, or at least 95% sequence identity with the 4-1BB costimulatory signaling region sequence as shown herein. The example sequence of the 4-1BB costimulatory signaling region is provided in U.S. App. No. U.S. Ser. No. 13/826,258. The sequence of the 4-1BB costimulatory signaling region associated disclosed in the U.S. App. No. U.S. Ser. No. 13/826,258 is listed as follows: The 4-1BB costimulatory signaling region:

```
                                        (SEQ ID NO: 80)
KRGRKKLLYIFKQPFMRPVQTTQEEDGCSCRFPEEEEGGCEL
```

As used herein, the term "CD28 costimulatory signaling region" refers to a specific protein fragment associated with this name and any other molecules that have analogous biological function that share at least 70%, or alternatively at least 80% amino acid sequence identity, such as (but not limited to) 90% sequence identity, or at least 95% sequence identity with the CD28 costimulatory signaling region sequence shown herein. Exemplary CD28 costimulatory signaling domains are provided in U.S. Pat. No. 5,686,281; Geiger, T. L. et al., Blood 98: 2364-2371 (2001); Hombach, A. et al., J Immunol 167: 6123-6131 (2001); Maher, J. et al. Nat Biotechnol 20: 70-75 (2002); Haynes, N. M. et al., J Immunol 169: 5780-5786 (2002); Haynes, N. M. et al., Blood 100: 3155-3163 (2002). Non-limiting examples include residues 114-220 of the below CD28 Sequence: MLRLLLALNL FPSIQVTGNK ILVKQSPMLV AYD-NAVNLSC KYSYNLFSRE FRASLHKGLD SAVEVCV-VYG NYSQQLQVYS KTGFNCDGKL GNESVTFYLQ NLYVNQTDIY FCKIEVMYPP PYLDNEKSNG TIIHVKGKHL CPSPLFPGPS KPFWVLVVVG GVLA-CYSLLV TVAFIIFWVR SKRSRLLHSD YMNMTPRRPG PTRKHYQPYA PPRDFAAYRS (SEQ ID NO: 81), and equivalents thereof.

As used herein, the term "ICOS costimulatory signaling region" refers to a specific protein fragment associated with this name and any other molecules that have analogous biological function that share at least 70%, or alternatively at least 80% amino acid sequence identity, such as (but not limited to) 90% sequence identity, or at least 95% sequence identity with the ICOS costimulatory signaling region sequence as shown herein. Non-limiting example sequences of the ICOS costimulatory signaling region are provided in U.S. Publication 2015/0017141A1 the exemplary polynucleotide sequence provided below. ICOS costimulatory signaling region:

```
                                        (SEQ ID NO: 82)
ACAAAAAAGA AGTATTCATC CAGTGTGCAC GACCCTAACG
GTGAATACAT GTTCATGAGA GCAGTGAACA CAGCCAAAAA
ATCCAGACTC ACAGATGTGA CCCTA
```

As used herein, the term "OX40 costimulatory signaling region" refers to a specific protein fragment associated with this name and any other molecules that have analogous biological function that share at least 70%, or alternatively at least 80% amino acid sequence identity, or alternatively 90% sequence identity, or alternatively at least 95% sequence identity with the OX40 costimulatory signaling region sequence as shown herein. Non-limiting example sequences of the OX40 costimulatory signaling region are disclosed in U.S. Publication 2012/20148552A1, and include the exemplary sequence provided below. OX40 costimulatory signaling region:

```
                                        (SEQ ID NO: 83)
AGGGACCAG AGGCTGCCCC CCGATGCCCA CAAGCCCCCT
GGGGGAGGCA GTTTCCGGAC CCCCATCCAA GAGGAGCAGG
CCGACGCCCA CTCCACCCTG GCCAAGATC
```

As used herein, the term "CD3 zeta signaling domain" refers to a specific protein fragment associated with this name and any other molecules that have analogous biological function that share at least 70%, or alternatively at least 80% amino acid sequence identity, such as (but not limited to) 90% sequence identity, or at least 95% sequence identity with the CD3 zeta signaling domain sequence as shown herein. The example sequences of the CD3 zeta signaling domain are provided in U.S. Pub. No. US 2013/0266551A1. The sequence associated with the CD3 zeta signaling domain is listed as follows: The CD3 zeta signaling domain:

```
                                        (SEQ ID NO: 84)
RVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATK
DTYDALHMQALPPR
```

As used herein, the term "suicide gene" is a gene capable of inducing cell apoptosis; non-limiting examples include HSV-TK (Herpes simplex virus thymidine kinase), cytosine deaminase, nitroreductase, carboxylesterase, cytochrome P450 or PNP (Purine nucleoside phosphorylase), truncated EGFR, or inducible caspase ("iCasp"). Suicide genes may function along a variety of pathways, and, in some cases, may be inducible by an inducing agent such as a small molecule. For example, the iCasp suicide gene comprises portion of a caspase protein operatively linked to a protein optimized to bind to an inducing agent; introduction of the inducing agent into a cell comprising the suicide gene results in the activation of caspase and the subsequent apoptosis of said cell.

As used herein, the term "switch mechanism for controlling expression and/or activation of the CAR" refers to an extracellular, transmembrane, and intracellular domain, in which the extracellular domain comprises a target-specific binding element that comprises a label, binding domain, or tag that is specific for a molecule other than the target antigen that is expressed on or by a target cell. The specificity of the CAR is provided by a second construct that comprises a target antigen binding domain (e.g., an anti-DCLK1 antibody or fragment thereof or a bispecific antibody that binds DCLK1 and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but it cannot bind its target antigen (i.e., DCLK1) until the second composition comprising a DCLK1-specific binding domain is administered.

As used herein, the term "B cell," refers to a type of lymphocyte in the humoral immunity of the adaptive immune system. B cells principally function to make antibodies, serve as antigen presenting cells, release cytokines, and develop memory B cells after activation by antigen interaction. B cells are distinguished from other lymphocytes, such as T cells, by the presence of a B-cell receptor on the cell surface. B cells may either be isolated or obtained from a commercially available source. Non-limiting examples of commercially available B cell lines include lines AHH-1 (ATCC® CRL-8146™), BC-1 (ATCC® CRL-2230™), BC-2 (ATCC® CRL-2231™), BC-3 (ATCC® CRL-2277™), CA46 (ATCC® CRL-1648™), DG-75 [D.G.-75] (ATCC® CRL-2625™), DS-1 (ATCC® CRL-11102™), EB-3 [EB3] (ATCC® CCL-85™), Z-138 (ATCC #CRL-3001), DB (ATCC CRL-2289), Toledo (ATCC CRL-2631), Pfiffer (ATCC CRL-2632), SR (ATCC CRL-2262), JM-1 (ATCC CRL-10421), NFS-5 C-1 (ATCC CRL-1693); NFS-70 C10 (ATCC CRL-1694), NFS-25 C-3 (ATCC CRL-1695), AND SUP-B15 (ATCC CRL-1929). Further examples include but are not limited to cell lines derived from anaplastic and large cell lymphomas, e.g., DEL, DL-40, FE-PD, JB6, Karpas 299, Ki-JK, Mac-2A Ply1, SR-786, SU-DHL-1, -2, -4, -5, -6, -7, -8, -9, -10, and -16, DOHH-2, NU-DHL-1, U-937, Granda 519, USC-DHL-1, RL; Hodgkin's lymphomas, e.g., DEV, HD-70, HDLM-2, HD-MyZ, HKB-1, KM-H2, L 428, L 540, L1236, SBH-1, SUP-HD1, SU/RH-HD-1. Non-limiting exemplary sources for such commercially available cell lines include the American Type Culture Collection, or ATCC, (www.atcc.org/) and the German Collection of Microorganisms and Cell Cultures (https://www.dsmz.de/).

As used herein, the term "CRISPR" refers to a technique of sequence specific genetic manipulation relying on the clustered regularly interspaced short palindromic repeats pathway. CRISPR can be used to perform gene editing and/or gene regulation, as well as to simply target proteins to a specific genomic location. "Gene editing" refers to a type of genetic engineering in which the nucleotide sequence of a target polynucleotide is changed through introduction of deletions, insertions, single stranded or double stranded breaks, or base substitutions to the polynucleotide sequence. In some aspect, CRISPR-mediated gene editing utilizes the pathways of nonhomologous end-joining (NHEJ) or homologous recombination to perform the edits. Gene regulation refers to increasing or decreasing the production of specific gene products such as protein or RNA.

The term "gRNA" or "guide RNA" as used herein refers to guide RNA sequences used to target specific polynucleotide sequences for gene editing employing the CRISPR technique.

Techniques of designing gRNAs and donor therapeutic polynucleotides for target specificity are well known in the art. For example, Doench, J., et al. Nature biotechnology 2014; 32(12):1262-7, Mohr, S. et al. (2016) FEBS Journal 283: 3232-38, and Graham, D., et al. Genome Biol. 2015; 16: 260. gRNA comprises or alternatively consists essentially of, or yet further consists of a fusion polynucleotide comprising CRISPR RNA (crRNA) and trans-activating CRIPSPR RNA (tracrRNA); or a polynucleotide comprising CRISPR RNA (crRNA) and trans-activating CRIPSPR RNA (tracrRNA). In some aspect, a gRNA is synthetic (Kelley, M. et al. (2016) J of Biotechnology 233 (2016) 74-83).

The term "Cas9" refers to a CRISPR associated endonuclease referred to by this name. Non-limiting exemplary Cas9s include Staphylococcus aureus Cas9, nuclease dead Cas9, and orthologs and biological equivalents each thereof. Orthologs include but are not limited to Streptococcus pyogenes Cas9 ("spCas9"), Cas 9 from Streptococcus thermophiles, Legionella pneumophilia, Neisseria lactamica, Neisseria meningitidis, Francisella novicida; and Cpf1 (which performs cutting functions analogous to Cas9) from various bacterial species including Acidaminococcus spp. and Francisella novicida U112.

The term "transduce" or "transduction" as it is applied to the production of chimeric antigen receptor cells refers to the process whereby a foreign nucleotide sequence is introduced into a cell. In some embodiments, this transduction is done via a vector.

As used herein, the term "vector" refers to a nucleic acid construct deigned for transfer between different hosts, including but not limited to a plasmid, a virus, a cosmid, a phage, a BAC, a YAC, etc. A "viral vector" is defined as a recombinantly produced virus or viral particle that comprises a polynucleotide to be delivered into a host cell, either in vivo, ex vivo or in vitro. In some embodiments, plasmid vectors may be prepared from commercially available vectors. In other embodiments, viral vectors may be produced from baculoviruses, retroviruses, adenoviruses, AAVs, etc. according to techniques known in the art. In one embodiment, the viral vector is a lentiviral vector. Examples of viral vectors include retroviral vectors, adenovirus vectors, adeno-associated virus vectors, alphavirus vectors and the like. Infectious tobacco mosaic virus (TMV)-based vectors can be used to manufacturer proteins and have been reported to express Griffithsin in tobacco leaves (O'Keefe et al. (2009) Proc. Nat. Acad. Sci. USA 106(15):6099-6104). Alphavirus vectors, such as Semliki Forest virus-based vectors and Sindbis virus-based vectors, have also been developed for use in gene therapy and immunotherapy. See, Schlesinger & Dubensky (1999) Curr. Opin. Biotechnol. 5:434-439 and Ying et al. (1999) Nat. Med. 5(7):823-827. In aspects where gene transfer is mediated by a retroviral vector, a vector construct refers to the polynucleotide comprising the retroviral genome or part thereof, and a gene of interest such as a polynucleotide encoding a CAR. Further details as to modern methods of vectors for use in gene transfer may be found in, for example, Kotterman et al. (2015) Viral Vectors for Gene Therapy: Translational and Clinical Outlook Annual Review of Biomedical Engineering 17. Vectors that contain both a promoter and a cloning site into which a polynucleotide can be operatively linked are well known in the art. Such vectors are capable of transcribing RNA in vitro or in vivo and are commercially available from sources such as Agilent Technologies (Santa Clara, Calif.) and Promega Biotech (Madison, Wis.).

As used herein, the terms "T2A" and "2A peptide" are used interchangeably to refer to any 2A peptide or fragment thereof, any 2A-like peptide or fragment thereof, or an artificial peptide comprising the requisite amino acids in a relatively short peptide sequence (on the order of 20 amino acids long depending on the virus of origin) containing the consensus polypeptide motif D-V/I-E-X-N-P-G-P (SEQ ID NO: 85), wherein X refers to any amino acid generally thought to be self-cleaving.

"Immune cells" include all cells that are produced by hematopoietic stem cells (HSC) including, but not limited to, HSCs, white blood cells (leukocytes), lymphocytes (including T cells, B cells, and natural killer (NK) cells) and myeloid-derived cells (neutrophils, eosinophils, basophils, monocytes, macrophages, dendritic cells). "Leukocytes" include but are not limited to lymphocytes, granulocytes, monocytes, and macrophages.

As used herein, the phrase "immune response" or its equivalent "immunological response" refers to the development of a cell-mediated response (e.g. mediated by antigen-specific T cells or their secretion products). A cellular immune response is elicited by the presentation of polypeptide epitopes in association with Class I or Class II MHC molecules, to treat or prevent a viral infection, expand antigen-specific B-reg cells, TC1, CD4+T helper cells and/or CD8+ cytotoxic T cells and/or disease generated, auto-regulatory T cell and B cell "memory" cells. The response may also involve activation of other components. In some aspect, the term "immune response" may be used to encompass the formation of a regulatory network of immune cells. Thus, the term "regulatory network formation" may refer to an immune response elicited such that an immune cell, such as (but not limited to) a T cell, and in particular (but not by way of limitation) a T regulatory cell, triggers further differentiation of other immune cells, such as but not limited to, B cells or antigen-presenting cells—non-limiting examples of which include dendritic cells, monocytes, and macrophages. In certain embodiments, regulatory network formation involves B cells being differentiated into regulatory B cells; in certain embodiments, regulatory network formation involves the formation of tolerogenic antigen-presenting cells.

The terms "inflammatory response" and "inflammation" as used herein indicate the complex biological response of immune cells, humoral factors, and vascular tissues of an individual or subject to exogenous or endogenous stimuli, such as pathogens, damaged cells, or irritants, and/or inflammatory signals such as pro-inflammatory cytokines. The inflammatory response includes secretion of cytokines and, more particularly, of pro-inflammatory cytokines, i.e. cytokines which are produced predominantly by activated immune cells and are involved in the amplification of inflammatory reactions. Exemplary pro-inflammatory cytokines and chemokines include but are not limited to IL-1β, TNF-α, IFN-γ, IL-8, IL-6, IL-12, IL-15, IL-16, IL-17 (including family members IL17A, IL17B, IL-17C, IL-17D, IL-17E, IL17F), IL-18, GM-CSF, IL-21, IL-23, IL-27 and TGF-β. Exemplary anti-inflammatory cytokines include but are not limited to TGF-β, IL-1Rα, IL-4, IL-6, IL-10, IL-11, IL-13, IL-35, INF-α. A cytokine may have either pro-inflammatory and anti-inflammatory properties depending on the particular biological context (Cavaillon, J. M (2001) Cell Mol. Biol 47(4): 695-702). Exemplary inflammations include acute inflammation and chronic inflammation. Acute inflammation indicates a short-term process characterized by the classic signs of inflammation (swelling, redness, pain, heat, and loss of function) due to the infiltration of the tissues by plasma and leukocytes. An acute inflammation typically occurs as long as the injurious stimulus is present and ceases once the stimulus has been removed, broken down, or walled off by scarring (fibrosis). Chronic inflammation indicates a condition characterized by concurrent active inflammation, tissue destruction, and attempts at repair. Chronic inflammation is not characterized by the classic signs of acute inflammation listed above. Instead, chronically inflamed tissue is characterized by the infiltration of mononuclear immune cells (monocytes, macrophages, lymphocytes, and plasma cells), tissue destruction, and attempts at healing, which include angiogenesis and fibrosis. An inflammation can be inhibited in the sense of the present disclosure by affecting and in particular inhibiting any one of the events that form the complex biological response associated with an inflammation in an individual.

As used herein, the term "T cell," refers to a type of lymphocyte that matures in the thymus. T cells play an important role in cell-mediated immunity and are distinguished from other lymphocytes, such as B cells, by the presence of a T-cell receptor on the cell surface. T-cells may either be isolated or obtained from a commercially available source. "T cell" includes all types of immune cells expressing CD3 including T-helper cells (CD4+ cells), cytotoxic T-cells (CD8+ cells), natural killer T-cells, T-regulatory cells (T-reg) and gamma-delta T cells. A "cytotoxic cell" includes CD8+ T cells, natural-killer (NK) cells, and neutrophils, which cells are capable of mediating cytotoxicity responses. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC #CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-KI, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4; 11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCC TIB-162). Null leukemia cell lines, including but not limited to REH, NALL-1, KM-3, L92-221, are a another commercially available source of immune cells, as are cell lines derived from other leukemias and lymphomas, such as K562 erythroleukemia, THP-1 monocytic leukemia, U937 lymphoma, HEL erythroleukemia, HL60 leukemia, HMC-1 leukemia, KG-1 leukemia, U266 myeloma. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the term "NK cell," also known as natural killer cell, refers to a type of lymphocyte that originates in the bone marrow and play a critical role in the innate immune system. NK cells provide rapid immune responses against viral-infected cells, tumor cells or other stressed cell, even in the absence of antibodies and major histocompatibility complex on the cell surfaces. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (http://www.atcc.org/) and the German Collection of Microorganisms and Cell Cultures (https://www.dsmz.de/).

As used herein, the terms "nucleic acid sequence" and "polynucleotide" are used interchangeably to refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "encode" as it is applied to nucleic acid sequences refers to a polynucleotide which is said to "encode" a polypeptide if, in its native state or when manipulated by methods well known to those skilled in the art, can be transcribed and/or translated to produce the mRNA for the polypeptide and/or a fragment thereof. The antisense strand is the complement of such a nucleic acid, and the encoding sequence can be deduced therefrom.

As used herein, the term signal peptide or signal polypeptide intends an amino acid sequence usually present at the N-terminal end of newly synthesized secretory or membrane polypeptides or proteins. It acts to direct the polypeptide across or into a cell membrane and is then subsequently removed. Examples of such are well known in the art. Non-limiting examples are those described in U.S. Pat. Nos. 8,853,381 and 5,958,736.

The term "promoter" as used herein refers to any sequence that regulates the expression of a coding sequence, such as a gene. Promoters may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors.

As used herein, the term "isolated cell" generally refers to a cell that is substantially separated from other cells of a tissue. "Immune cells" includes, e.g., white blood cells (leukocytes) which are derived from hematopoietic stem cells (HSC) produced in the bone marrow, lymphocytes (T cells, B cells, natural killer (NK) cells), myeloid-derived cells (neutrophil, eosinophil, basophil, monocyte, macrophage, dendritic cells), as well as precursors thereof committed to immune lineages. Precursors of T-cells are lineage restricted stem and progenitor cells capable of differentiating to produce a mature T-cell. Precursors of T-cells include HSCs, long term HSCs, short term HSCs, multipotent progenitor cells (MPPs), lymphoid primed multipotent progenitor cells (LMPPs), early lymphoid progenitor cells (ELPs), common lymphoid progenitor cells (CLPs), Pro-T-cells (ProT), early T-lineage progenitors/double negative 1 cells (ETPs/DN1), double negative (DN) 2a, DN2b, DN3a, DN3b, DN4, and double positive (DP) cells. Markers of such T-cell precursors in humans include but are not limited to: HSCs: CD34+ and, optionally, CD38−; long term HSCs: CD34+CD38− and lineage negative, wherein lineage negative means negative for one or more lineage specific markers selected from the group of TER119, Mac1, Gr1, CD45R/B220, CD3, CD4, and CD8; MPPs: CD34+CD38− CD45RA− CD90− and, optionally, lineage negative; CLP: CD34+CD38+CD10+ and, optionally, lineage negative; LMPP/ELP: CD45RA+CD62L+CD38− and, optionally, lineage negative; DN1: CD117− CD34+CD38− CD1a−; DN2: CD117+CD34+CD38+CD1a−; DN3: CD34+CD38+CD1a+; DN4: CD4+CD3−; DP: CD4+CD8+ and, optionally, CD3+. Precursors of NK cells are lineage restricted stem and progenitor cells capable of differentiating to produce a mature NK cell. NK precursors include HSCs, long term HSCs, short term HSCs, multipotent progenitor cells (MPPs), common myeloid progenitors (CMP), granulocyte-macrophage progenitors (GMP), pro-NK, pre-NK, and immature NK (iNK). Markers of such NK precursors include but are not limited to: CMP: CD56− CD36− CD33+ CD34+ NKG2D− NKp46−; GMP: CD56− CD36− CD33+ CD34+ NKG2D− NKp46−; pro-NK: CD34+CD45RA+ CD10+CD117− CD161−; pre-NK: CD34+CD45RA+ CD10− CD117+CD161+/−; and iNK: CD34− CD117+ CD161+ NKp46− CD94/NKG2A−. In some aspect, markers of NK cell precursors include but are not limited to CD117+ CD161+CD244+CD33+CD56− NCR− CD94/NKG2A− and LFA-1−. Phenotyping reagents to detect precursor cell surface markers are available from, for example, BD Biosciences (San Jose, CA) and BioLegend (San Diego, CA). "T cell" includes all types of immune cells expressing CD3 including T-helper cells (CD4+ cells), cytotoxic T-cells (CD8+ cells), natural killer T-cells, T-regulatory cells (T-reg) and gamma-delta T cells. A "cytotoxic cell" includes CD8+ T cells, natural-killer (NK) cells, and neutrophils, which cells are capable of mediating cytotoxicity responses.

The term "transduce" or "transduction" as it is applied to the production of chimeric antigen receptor cells refers to the process whereby a foreign nucleotide sequence is introduced into a cell. In some embodiments, this transduction is done via a vector.

As used herein, the term "autologous," in reference to cells refers to cells that are isolated and infused back into the same subject (recipient or host). "Allogeneic" refers to non-autologous cells.

An "effective amount" or "efficacious amount" refers to the amount of an agent, or combined amounts of two or more agents, that, when administered for the treatment of a mammal or other subject, is sufficient to affect such treatment for the disease. The "effective amount" will vary depending on the agent(s), the disease and its severity and the age, weight, etc., of the subject to be treated.

As used herein, a "cancer" is a disease state characterized by the presence in a subject of cells demonstrating abnormal uncontrolled replication and may be used interchangeably with the term "tumor." In some embodiments, the cancer is colon, rectal, intestinal, gastric, pancreatic, prostate, cervical, or ovarian cancer, or fibrosarcoma, lung cancer, liver cancer, esophageal cancer, breast cancer, major salivary gland carcinoma, neuroblastoma or renal cell carcinoma, or blood cancers such as leukemian and multiple myeloma. Colon and rectal cancer, or colorectal cancer, refers to a cancer that starts in the large intestine (colon) or the rectum (end of the colon). Non-limiting examples of colorectal cancer cells are HCT116, HT29, SW620 CaCo2, LS123 or LoVo cells. Phenotypes of these colorectal cancer cells are described in Ahmed, D et al. "Epigenetic and genetic features of 24 colon cancer cell lines" Oncogenesis vol. 2, 9 e71. (2013).

Intestinal cancer refers to a cancer that starts in the small intestine. Gastric or stomach cancer refers to the cancer that develops in the stomach generally in the cells forming the lining of the stomach. Pancreatic cancer refers to a cancer that starts in the pancreas. Non-liming examples of pancreatic cancer cells are BxPC3 cells. Phenotypes of these pancreatic cancer cells are described in Deer, Emily L et al. "Phenotype and genotype of pancreatic cancer cell lines" Pancreas vol. 39, 4: 425-35 (2010).

Cervical cancer refers to a cancer that develops in the cervix. Non-limiting examples of cervical cancer cells are HeLa cells. Phenotypes of these cervical cancer cells are described in Chen T R. (1988) "Re-evaluation of HeLa, HeLa S3, and HEp-2 karyotypes" Cytogenet. Cell Genet. 48:19-24, and Macville M, et al. (1999) "Comprehensive and definitive molecular cytogenetic characterization of HeLa cells by spectral karyotyping" Cancer Res. 59:141-150.

Fibrosarcoma refers to the cancer that starts in the fibroblast cells. Non-limiting examples of fibrosarcoma cells are HT1080 cells. Phenotypes of these fibrosarcoma cells are described in Rasheed, S. et al. "Characterization of a newly derived human sarcoma cell line (HT-1080)" Cancer 33, 1027-1033 (1974) and Hu M et al. "Purification and characterization of human lung fibroblast motility-stimulating factor for human soft tissue sarcoma cells: identification as an NH2-terminal fragment of human fibronectin" Cancer Res. Vol. 57:3577-3584 (1997).

Multiple myeloma refers to a cancer that starts in the plasma cells in the blood. Non-limiting examples of multiple myeloma cells are RPMI8226, MM1S, or K562 cells. Phenotypes of these multiple myeloma cells are described in Moore G E et al. "Cell line derived from patient with myeloma" N.Y. State J. Med. 68: 2054-2060 (1968), Pellat-Deceunynk C, et al. "Human myeloma cell lines as a tool for studying the biology of multiple myeloma: a reappraisal 18 years after" Blood 86: 4001-4002 (1995), Goldman-Leikin R E, et al. "Characterization of a novel myeloma cell line, MM.1" J. Lab. Clin. Med. 113(3):335-345 (1989), Greenstein S, et al. "Characterization of the MM.1 human multiple myeloma (MM) cell lines: A model system to elucidate the characteristics, behavior, and signaling of steroid-sensitive and -resistant MM cells" Exp. Hematol.:31:271-282 (2003), Moalli P A, et al. "A mechanism of resistance to glucocorticoids in multiple myeloma: transient expression of a truncated glucocorticoid receptor mRNA" Blood. 79:213-222 (1992), H P Koeffler et al. "Human myeloid leukemia cell lines: a review" Blood 56:344-350 (1980), Lozzio B B et al. "Properties and usefulness of the original K-562 human myelogenous leukemia cell line" Leuk. Res. 3:363-370 (1979), Andersson L C, et al. K562—a human erythroleukemic cell line. Int. J. Cancer 23:143-147 (1979), and Lozzio B B, et al. A multipotential leukemia cell line (K-562) of human origin. Proc. Soc. Exp. Biol. Med. 166:546-550 (1981).

The term "ovarian cancer" refers to a type of cancer that forms in issues of the ovary and has undergone a malignant transformation that makes the cells within the cancer pathological to the host organism with the ability to invade or spread to other parts of the body. The ovarian cancer herein comprises type I cancers of low histological grade and type II cancer of higher histological grade. Particularly, the ovarian cancer includes but is not limited to epithelial carcinoma, serous carcinoma, clear-cell carcinoma, sex cord stromal tumor, germ cell tumor, dysgerminoma, mixed tumors, secondary ovarian cancer, low malignant potential tumors. Non-limiting examples of ovarian cancer cells are SKOV3 or OVCAR-3 cells. Phenotypes of these ovarian cancer cells are described in Fogh J. "Human tumor cells in vitro" New York: Plenum Press; (1975), Wiechen K, et al. "Suppression of the c-erbB-2 gene product decreases transformation abilities but not the proliferation and secretion of proteases of SK-OV-3 ovarian cancer cells" Br. J. Cancer 81:790-795 (1999) and Hamilton T C, et al. "Characterization of a human ovarian carcinoma cell line (NIH: OVCAR-3) with androgen and estrogen receptors" Cancer Res. 43:5379-5389, (1983).

The term "prostate cancer" refers to a type of cancer that develops in the prostate, a gland in the male reproductive system. The prostate cancer herein includes but is not limited to adenocarcinoma, sarcomas, small cell carcinomas, neuroendocrine tumors, transitional cell carcinomas. Non-liming examples of prostate cancer cells are LNCaP cells. Phenotypes of these prostate cancer cells are described in "Models for prostate cancer" 37 New York: Liss; (1980), Gibas Z, et al. "A high-resolution study of chromosome changes in a human prostatic carcinoma cell line (LNCaP)" Cancer Genet. Cytogenet. 11:399-404, (1984), Horoszewicz J S, et al. "LNCaP model of human prostatic carcinoma" Cancer Res. 43:1809-1818, (1983) and Sieh, Shirly et al. "Phenotypic characterization of prostate cancer LNCaP cells cultured within a bioengineered microenvironment" PloS one vol. 7, 9:e40217 (2012).

As used herein, the terms "lung cancer," "liver cancer," "esophageal cancer," and "breast cancer" refer to cancers that start in the lung, liver, esophagus, and breast respectively.

"Renal cell carcinoma" refers to a cancer that starts in tubules of a kidney.

"Major salivary gland carcinoma" refers to a cancer that develops in one or more of the parotid salivary glands or submandibular salivary glands or sublingual salivary glands.

"Neuroblastoma" refers to a cancer that develops from immature nerve cells found in several areas of the body. Non-limiting examples of areas around which neuroblastoma develops are the adrenal glands, abdomen, chest, neck and spine.

A "solid tumor" is an abnormal mass of tissue that usually does not contain cysts or liquid areas. Solid tumors can be benign or malignant. Different types of solid tumors are named for the type of cells that form them. Examples of solid tumors include sarcomas, carcinomas, and lymphomas.

The term "B cell lymphoma or leukemia" refers to a type of cancer that forms in issues of the lymphatic system or bone marrow and has undergone a malignant transformation that makes the cells within the cancer pathological to the host organism with the ability to invade or spread to other parts of the body.

The term "thyroid cancer" refers to a type of cancer that develops in the thyroid.

As used herein, the term "detectable marker" refers to at least one marker capable of directly or indirectly, producing a detectable signal. A non-exhaustive list of this marker includes enzymes which produce a detectable signal, for example by colorimetry, fluorescence, luminescence, such as horseradish peroxidase, alkaline phosphatase, β-galactosidase, glucose-6-phosphate dehydrogenase, chromophores such as fluorescent, luminescent dyes, groups with electron density detected by electron microscopy or by their electrical property such as conductivity, amperometry, voltammetry, impedance, detectable groups, for example whose molecules are of sufficient size to induce detectable modifications in their physical and/or chemical properties, such detection may be accomplished by optical methods such as diffraction, surface plasmon resonance, surface variation, the contact angle change or physical methods such as atomic force spectroscopy, tunnel effect, or radioactive molecules such as $^{32}$ P, $^{35}$ S or $^{125}$ I.

As used herein, the term "purification marker" refers to at least one marker useful for purification or identification. A non-exhaustive list of this marker includes His, lacZ, GST, maltose-binding protein, NusA, BCCP, c-myc, CaM, FLAG, GFP, YFP, cherry, thioredoxin, poly (NANP), V5, Snap, HA, chitin-binding protein, Softag 1, Softag 3, Strep, or S-protein. Suitable direct or indirect fluorescence marker comprise FLAG, GFP, YFP, RFP, dTomato, cherry, Cy3, Cy 5, Cy 5.5, Cy 7, DNP, AMCA, Biotin, Digoxigenin, Tamra, Texas Red, rhodamine, Alexa fluors, FITC, TRITC or any other fluorescent dye or hapten.

As used herein, the term "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound. The terms "upregulate" and "downregulate" and variations thereof when used in context of gene expression, respectively, refer to the increase and decrease of gene expression relative to a normal or expected threshold expression for cells, in general, or the sub-type of cell, in particular.

As used herein, the term "reduce or eliminate expression and/or function of" refers to reducing or eliminating the transcription of said polynucleotides into mRNA, or alternatively reducing or eliminating the translation of said mRNA into peptides, polypeptides, or proteins, or reducing or eliminating the functioning of said peptides, polypeptides, or proteins. In a non-limiting example, the transcription of polynucleotides into mRNA is reduced to at least half of its normal level found in wild type cells.

As used herein, the term "increase expression of" refers to increasing the transcription of said polynucleotides into mRNA, or alternatively increasing the translation of said mRNA into peptides, polypeptides, or proteins, or increasing the functioning of said peptides, polypeptides, or proteins. In a non-limiting example, the transcription of polynucleotides into mRNA is increased to at least twice of its normal level found in wild type cells.

The phrase "first line" or "second line" or "third line" refers to the order of treatment received by a patient. First line therapy regimens are treatments given first, whereas second or third line therapy are given after the first line therapy or after the second line therapy, respectively. The National Cancer Institute defines first line therapy as "the first treatment for a disease or condition. In patients with cancer, primary treatment can be surgery, chemotherapy, radiation therapy, or a combination of these therapies. First line therapy is also referred to those skilled in the art as "primary therapy and primary treatment." See National Cancer Institute website at cancer.gov, last visited Nov. 15, 2017. Typically, a patient is given a subsequent chemotherapy regimen because the patient did not show a positive clinical or sub-clinical response to the first line therapy or the first line therapy has stopped.

In one aspect, the term "equivalent" or "biological equivalent" of an antibody means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody.

It is to be inferred without explicit recitation and unless otherwise intended, that when the present disclosure relates to a polypeptide, protein, polynucleotide or antibody, an equivalent or a biologically equivalent of such is intended within the scope of this disclosure. As used herein, the term "biological equivalent thereof" is intended to be synonymous with "equivalent thereof" when referring to a reference protein, antibody, polypeptide or nucleic acid, intends those having minimal homology while still maintaining desired structure or functionality. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement.

A polynucleotide or polynucleotide region (or a polypeptide or polypeptide region) having a certain percentage (for example, 80%, 85%, 90%, or 95%) of "sequence identity" to another sequence means that, when aligned, that percentage of bases (or amino acids) are the same in comparing the two sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain non-limiting embodiments, default parameters are used for alignment. One particular (but non-limiting) alignment program is BLAST, using default parameters. In particular, certain non-limiting programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST.

As used herein, "homology" or "identical", percent "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, such as (but not limited to) at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The alignment and the percent homology or sequence identity can be determined using software programs known in the art, for example those described in Current Protocols in Molecular Biology (Ausubel et al., eds. 1987) Supplement 30, section 7.7.18, Table 7.7.1. In certain particular (but non-limiting) embodiments, default parameters are used for alignment. A particular (but non-limiting) alignment program is BLAST, using default parameters. In particular (but not by way of limitation), certain programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+ EMBL+DDBJ+PDB+GenBank CDS translations+ SwissProtein+SPupdate+PIR. Details of these programs can be found at the following Internet address: ncbi.nlm.nih.gov/cgi-bin/BLAST. The terms "homology" or "identical", percent "identity" or "similarity" also refer to, or can be applied to, the complement of a test sequence. The terms also include sequences that have deletions and/or additions, as well as those that have substitutions. As described herein, the particular algorithms can account for gaps and the like. In certain non-limiting embodiments, identity exists over a region that is at least about 25 amino acids or nucleotides in length, or over a region that is at least 50-100 amino acids or nucleotides in length. An "unrelated" or "non-homologous" sequence shares less than 40% identity, or alternatively less than 25% identity, with one of the sequences disclosed herein.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

A "normal cell corresponding to the tumor tissue type" refers to a normal cell from a same tissue type as the tumor tissue. A non-limiting example is a normal lung cell from a patient having lung tumor, or a normal colon cell from a patient having colon tumor.

The term "isolated" as used herein refers to molecules or biologicals or cellular materials being substantially free from other materials. In one aspect, the term "isolated" refers to nucleic acid, such as DNA or RNA, or protein or polypeptide (e.g., an antibody or derivative thereof), or cell or cellular organelle, or tissue or organ, separated from other DNAs or RNAs, or proteins or polypeptides, or cells or cellular organelles, or tissues or organs, respectively, that are present in the natural source. The term "isolated" also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. The term "isolated" is also used herein to refer to cells or tissues that are isolated from other cells or tissues and is meant to encompass both cultured and engineered cells or tissues.

As used herein, the term "monoclonal antibody" refers to an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

The term "protein", "peptide" and "polypeptide" are used interchangeably and in their broadest sense to refer to a compound of two or more subunit amino acids, amino acid analogs or peptidomimetics. The subunits may be linked by peptide bonds. In another aspect, the subunit may be linked by other bonds, e.g., ester, ether, etc. A protein or peptide must contain at least two amino acids and no limitation is placed on the maximum number of amino acids which may comprise a protein's or peptide's sequence. As used herein the term "amino acid" refers to either natural and/or unnatural or synthetic amino acids, including glycine and both the D and L optical isomers, amino acid analogs and peptidomimetics.

The terms "polynucleotide" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, RNAi, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any aspect of this technology that is a polynucleotide encompasses both the double-stranded form and each of two complementary single-stranded forms known or predicted to make up the double-stranded form.

As used herein, the term "purified" does not require absolute purity; rather, it is intended as a relative term. Thus, for example, a purified nucleic acid, peptide, protein, biological complexes or other active compound is one that is isolated in whole or in part from proteins or other contaminants. Generally, substantially purified peptides, proteins, biological complexes, or other active compounds for use within the disclosure comprise more than 80% of all macromolecular species present in a preparation prior to admixture or formulation of the peptide, protein, biological complex or other active compound with a pharmaceutical carrier, excipient, buffer, absorption enhancing agent, stabilizer, preservative, adjuvant or other co-ingredient in a complete pharmaceutical formulation for therapeutic administration. More typically, the peptide, protein, biological complex or other active compound is purified to represent greater than 90%, often greater than 95% of all macromolecular species present in a purified preparation prior to admixture with other formulation ingredients. In other cases, the purified preparation may be essentially homogeneous, wherein other macromolecular species are not detectable by conventional techniques.

As used herein, the term "specific binding" means the contact between an antibody or antigen binding domain and an antigen with a binding affinity less as disclosed herein, e.g., than or about $10^{-6}$ M. In certain aspects, antibodies bind with affinities less than or about $10^{-7}$M, such as (but not limited to) about $10^{-8}$M, about $10^{-9}$M, about $10^{-10}$ M, about $10^{-11}$ M, or about $10^{-12}$ M.

As used herein, the term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

As used herein, "treating" or "treatment" of a disease in a subject refers to (1) preventing the symptoms or disease from occurring in a subject that is predisposed or does not yet display symptoms of the disease; (2) inhibiting the disease or arresting its development or relapse; or (3) ameliorating or causing regression of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. When the disease is cancer, the following clinical end points are non-limiting examples of treatment: reduction in tumor burden, slowing of tumor growth, longer overall survival, longer time to tumor progression, inhibition of metastasis or a reduction in metastasis of the tumor. In one aspect, treatment excludes prophylaxis.

As used herein, the term "overexpress" with respect to a cell, a tissue, or an organ expresses a protein to an amount that is greater than the amount that is produced in a control cell, a control issue, or an organ. A protein that is overexpressed may be endogenous to the host cell or exogenous to the host cell.

As used herein the term "linker sequence" relates to any amino acid sequence comprising from 1 to 10, or alternatively, 8 amino acids, or alternatively 6 amino acids, or alternatively 5 amino acids that may be repeated from 1 to 10, or alternatively to about 8, or alternatively to about 6, or alternatively about 5, or 4 or alternatively 3, or alternatively 2 times. For example, the linker may comprise up to 15 amino acid residues consisting of a pentapeptide repeated three times. In one aspect, the linker sequence is a (Glycine4Serine)3_(SEQ ID NO: 86) flexible polypeptide linker comprising three copies of gly-gly-gly-gly-ser (SEQ ID NO: 87), or equivalents thereof. Non-limiting examples of linker sequences are known in the art, e.g., GGGGSGGGGSGGGG (SEQ ID NO: 88) (and equivalents thereof); the tripeptide EFM; or Glu-Phe-Gly-Ala-Gly-Leu-Val-Leu-Gly-Gly-Gln-Phe-Met (SEQ ID NO: 89), and equivalents of each thereof.

As used herein, the term "enhancer", as used herein, denotes sequence elements that augment, improve or ameliorate transcription of a nucleic acid sequence irrespective of its location and orientation in relation to the nucleic acid sequence to be expressed. An enhancer may enhance transcription from a single promoter or simultaneously from more than one promoter. As long as this functionality of improving transcription is retained or substantially retained (e.g., at least 70%, at least 80%, at least 90% or at least 95% of wild-type activity, that is, activity of a full-length sequence), any truncated, mutated or otherwise modified variants of a wild-type enhancer sequence are also within the above definition.

An example of an enhancer sequence is WPRE. As used herein, the term "WPRE" or "Woodchuck Hepatitis Virus (WHP) Post-transcriptional Regulatory Element" refers to a specific nucleotide fragment associated with this name and any other molecules that have analogous biological function that share at least 70%, or alternatively at least 80% amino acid sequence identity, such as (but not limited to) 90% sequence identity, or at least 95% sequence identity with the WPRE sequence as shown herein. For example, WPRE refers to a region similar to the human hepatitis B virus posttranscriptional regulatory element (HBVPRE) present in the Woodchuck hepatitis virus genomic sequence (GenBank Accession No. J04514), and that the 592 nucleotides from position 1093 to 1684 of this genomic sequence correspond to the post-transcriptional regulatory region (Journal of Virology, Vol. 72, p. 5085-5092, 1998). The analysis using retroviral vectors revealed that WPRE inserted into the 3'-terminal untranslated region of a gene of interest increases the amount of protein produced by 5 to 8 folds. It has also been reported that the introduction of WPRE suppresses mRNA degradation (Journal of Virology, Vol. 73, p. 2886-2892, 1999). In a broad sense, elements such as WPRE that increase the efficiency of amino acid translation by stabilizing mRNAs are also thought to be enhancers.

The term "contacting" means direct or indirect binding or interaction between two or more entities (e.g., between target cell population and anti-DCLK1 CAR expressing cells). A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration.

As used herein, the term "binds" or "antibody binding" or "specific binding" means the contact between the antigen binding domain of an antibody, antibody fragment, CAR, TCR, engineered TCR, BCR, MHC, immunoglobulin-like molecule, scFv, CDR or other antigen presentation molecule and an antigen, epitope, or peptide with a binding affinity (KD) of less than $10^{-5}$ M. In some aspect, an antigen binding domain binds to both a complex of both an antigen and an MHC molecule. In some aspect, antigen binding domains bind with affinities of less than about $10^{-6}$ M, or less than about $10^{-7}$ M, or less than about $10^{-8}$ M, or less than about $10^{-9}$ M, or less than about $10^{-10}$ M, or less than about $10^{-11}$ M, or less than about $10^{-12}$ M.

As used herein, the term "administer" and "administering" are used to mean introducing the therapeutic agent (e.g., polynucleotide, vector, cell, modified cell, population) into a subject. The therapeutic administration of this substance serves to attenuate any symptom or prevent additional symptoms from arising. When administration is for the purposes of preventing or reducing the likelihood of developing an autoimmune disease or disorder, the substance is provided in advance of any visible or detectable symptom. Routes of administration include, but are not limited to, oral (such as a tablet, capsule or suspension), topical, transdermal, intranasal, vaginal, rectal, subcutaneous intravenous, intraarterial, intramuscular, intraosseous, intraperitoneal, epidural and intrathecal.

The term "introduce" as applied to methods of producing modified cells such as chimeric antigen receptor cells refers to the process whereby a foreign (i.e. extrinsic or extracellular) agent is introduced into a host cell thereby producing a cell comprising the foreign agent. Methods of introducing nucleic acids include but are not limited to transduction, retroviral gene transfer, transfection, electroporation, transformation, viral infection, and other recombinant DNA techniques known in the art. In some embodiments, transduction is done via a vector (e.g., a viral vector). In some embodiments, transfection is done via a chemical carrier, DNA/liposome complex, or micelle (e.g., Lipofectamine (Invitrogen)). In some embodiments, viral infection is done via infecting the cells with a viral particle comprising the polynucleotide of interest (e.g., AAV). In some embodiments, introduction further comprises CRISPR mediated gene editing or Transcription activator-like effector nuclease (TALEN) mediated gene editing. Methods of introducing non-nucleic acid foreign agents (e.g., soluble factors, cytokines, proteins, peptides, enzymes, growth factors, signaling molecules, small molecule inhibitors) include but are not limited to culturing the cells in the presence of the foreign agent, contacting the cells with the agent, contacting the cells with a composition comprising the agent and an excipient, and contacting the cells with vesicles or viral particles comprising the agent.

The term "adherent cells" refer to cells that adhere to the surface of their growth or culture surface. Methods of culturing adherent cells in vitro are well-known in the art. Some non-limiting examples of methods of culturing adherent cells are described in Smalley K S et al. "Life isn't flat: taking cancer biology to the next dimension" In Vitro Cell Dev Biol Anim 42: 242-247 (2006), Qureshi-Baig, Komal et al. "What Do We Learn from Spheroid Culture Systems? Insights from Tumorspheres Derived from Primary Colon Cancer Tissue" PloS one vol. 11, 1 e0146052. (2016) and Nath, S. et al. "Three-dimensional culture systems in cancer research: Focus on tumor spheroid model" Pharmacology & therapeutics vol. 163: 94-108 (2016). The term "non-adherent cells" refer to cells that do not adhere to the surface of their growth or culture surface. Methods of growing non-adherent cells in vitro are well-known in the art. Non-limiting examples of methods of growing non-adherent cells in vitro are described in Culture of Animal Cells: A Manual of Basic Technique, 5th edition; Gait ed. (1984).

The term "culturing" refers to growing cells in a culture medium under conditions that favor expansion and proliferation of the cell. The term "culture medium" or "medium" is recognized in the art and refers generally to any substance or preparation used for the cultivation of living cells. The term "medium", as used in reference to a cell culture, includes the components of the environment surrounding the cells. Media may be solid, liquid, gaseous or a mixture of phases and materials. Media include liquid growth media as well as liquid media that do not sustain cell growth. Media also include gelatinous media such as agar, agarose, gelatin and collagen matrices. Exemplary gaseous media include the gaseous phase to which cells growing on a petri dish or other solid or semisolid support are exposed. The term "medium" also refers to material that is intended for use in a cell culture, even if it has not yet been contacted with cells. In other words, a nutrient rich liquid prepared for culture is a medium. Similarly, a powder mixture that when mixed with water or other liquid becomes suitable for cell culture may be termed a "powdered medium." "Defined medium" refers to media that are made of chemically defined (usually purified) components. "Defined media" do not contain poorly characterized biological extracts such as yeast extract and beef broth. "Rich medium" includes media that are designed to support growth of most or all viable forms of a particular species. Rich media often include complex biological extracts. A "medium suitable for growth of a high-density culture" is any medium that allows a cell culture to reach an OD600 of 3 or greater when other conditions (such as temperature and oxygen transfer rate) permit such growth. The term "basal medium" refers to a medium which promotes the growth of many types of microorganisms which do not require any special nutrient supplements. Most basal media generally comprise of four basic chemical groups: amino acids, carbohydrates, inorganic salts, and vitamins. A basal medium generally serves as the basis for a more complex medium, to which supplements such as serum, buffers, growth factors, lipids, and the like are added. In one aspect, the growth medium may be a complex medium with the necessary growth factors to support the growth and expansion of the cells of the disclosure while maintaining their self-renewal capability. Examples of basal media include, but are not limited to, Eagles Basal Medium, Minimum Essential Medium, Dulbecco's Modified Eagle's Medium, Medium 199, Nutrient Mixtures Ham's F-10 and Ham's F-12, McCoy's 5A, Dulbecco's MEM/F-I 2, RPMI 1640, and Iscove's Modified Dulbecco's Medium (IDMD).

"Cryoprotectants" are known in the art and include without limitation, e.g., sucrose, trehalose, and glycerol. A cryoprotectant exhibiting low toxicity in biological systems is generally used.

LIST OF ABBREVIATIONS

CAR: chimeric antigen receptor
IRES: internal ribosomal entry site
MFI: mean fluorescence intensity
MOI: multiplicity of infection
PBMC: peripheral blood mononuclear cells
PBS: phosphate buffered saline
scFv: single chain variable fragment
WPRE: woodchuck hepatitis virus post-transcriptional regulatory element

MODES FOR CARRYING OUT THE DISCLOSURE

CAR T-cells are genetically engineered autologous T-cells in which single chain antibody fragments (scFv) or ligands are attached to the T-cell signaling domain capable of facilitating T-cell activation (Maher, J. (2012) ISRN Oncol. 2012:278093; Curran, K. J. et al. (2012) J. Gene Med. 14:405-415; Fedorov, V. D. et al. (2014) Cancer J. 20:160-165; Barrett, D. M. et al. (2014) Annu. Rev. Med. 65:333-347). CARs combine HLA-independent targeting specificity of a monoclonal antibody with the cytolytic activity and homing properties of activated T-cells. These properties enable the recognition of target cells with reduced HLA expression or down-regulated antigen processing pathways, two common methods tumors employ to evade the host immune response (Jakobsen, M. K. et al. (1995) J. Immunother. Emphasis Tumor Immunol. 17:222-228; Lou, Y. et al. (2008) Clin. Cancer Res. 14:1494-1501; Singh, R. et al. (2007) Cancer Res. 67:1887-1892). CAR-modified T-cells have shown great promise in preclinical and clinical settings as novel therapeutics in various diseases including cancer.

This disclosure provides antibodies specific to DCLK1 and methods and compositions relating to the use and production thereof. In addition, this disclosure provides as a chimeric antigen receptor (CAR) comprising an antigen binding domain specific to DCLK1, that in some aspect, is the antigen binding domain of an anti-DCLK1 antibody and methods and compositions relating to the use and production thereof.

Consistent with these principles and discoveries, this disclosure provides the following embodiments.

Antibodies and Uses Thereof

The general structure of antibodies is known in the art and will only be briefly summarized here. An immunoglobulin monomer comprises two heavy chains and two light chains connected by disulfide bonds. Each heavy chain is paired with one of the light chains to which it is directly bound via a disulfide bond. Each heavy chain comprises a constant region (which varies depending on the isotype of the antibody) and a variable region. The variable region comprises three hypervariable regions (or complementarity determining regions) which are designated CDRH1, CDRH2 and CDRH3 and which are supported within framework regions. Each light chain comprises a constant region and a variable region, with the variable region comprising three hypervariable regions (designated CDRL1, CDRL2 and CDRL3) supported by framework regions in an analogous manner to the variable region of the heavy chain.

The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include: SEQ ID Nos: 60-68 or an equivalent of each thereof.

In some embodiments, the immunoglobulin-related compositions of the present technology comprise a heavy chain constant region that is at least 80%, at least 85%, at least 90%, at least 95%, at least 99%, or is 100% identical to SEQ ID Nos: 60-68.

The hypervariable regions of each pair of heavy and light chains mutually cooperate to provide an antigen binding site that is capable of binding a target antigen. The binding specificity of a pair of heavy and light chains is defined by the sequence of CDR1, CDR2 and CDR3 of the heavy and light chains. Thus once a set of CDR sequences (i.e. the sequence of CDR1, CDR2 and CDR3 for the heavy and light chains) is determined which gives rise to a particular binding specificity, the set of CDR sequences can, in principle, be inserted into the appropriate positions within any other antibody framework regions linked with any antibody constant regions in order to provide a different antibody with the same antigen binding specificity.

In one embodiment, the disclosure provides an isolated antibody comprising, or alternatively consisting essentially of, or yet further consisting of a heavy chain (HC) immunoglobulin variable domain sequence and a light chain (LC) immunoglobulin variable domain sequence, wherein the antibody binds to an epitope of a DCLK1.

Anti-DCLK1 Antibodies

In one aspect, the present disclosure provides an isolated antibody comprising, or alternatively consisting essentially of, or yet further consisting of a heavy chain (HC) immunoglobulin variable domain sequence and a light chain (LC) immunoglobulin variable domain sequence, wherein the heavy chain and light chain immunoglobulin variable domain sequences form an antigen binding site that binds to an epitope of DCLK1. In one aspect, the antibodies possess a binding affinity of at least $10^{-6}$ M. In certain aspects, antibodies bind with affinities of at least about $10^{-7}$M, and alternatively of at least about $10^{-8}$M, $10^{-9}$ M, $10^{-10}$ M, $10^{-11}$ M, or $10^{-12}$ M.

In some embodiments, the CDRH1 sequence of the heavy chain variable region comprises, or alternatively consists essentially of, or yet further consists of an amino acid sequence of the CDHR1 region of any one of the HC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRH2 sequence of the heavy chain variable region comprises, or alternatively consists essentially of, or yet further consists of an amino acid sequence of the CDHR2 region of any one of the HC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRH3 sequence of the heavy chain variable region comprises, or alternatively consists essentially of, or yet further consists of an amino acid sequence of the CDHR3 region of any one of the HC sequences disclosed herein or equivalents thereof, followed by followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the heavy chain variable region comprises, or alternatively consists essentially of, or yet further consists of, one of the below noted amino acid sequences: SEQ ID Nos: 1-10 or 16-25 or an antigen binding fragment thereof or an equivalent of each thereof. In some embodiments, the heavy chain variable region comprises, or alternatively consists essentially of, or yet further consists of, the polypeptide encoded by one of the below noted polynucleotide sequences: SEQ ID Nos: 32-40 or 46-47 or an antigen binding fragment thereof or an equivalent of each thereof. In one aspect, the anti-DCLK1 antibody variable region comprises, or alternatively consisting essentially of, or yet further consists of one of the below noted amino acid sequences: SEQ ID Nos: 1 and 11, or alternatively SEQ ID Nos: 1 and 12, or alternatively SEQ ID Nos: 1 and 13, or alternatively SEQ ID Nos: 1 and 14, or alternatively SEQ ID Nos: 1 and 15, or alternatively SEQ ID Nos: 2 and 11, or alternatively SEQ ID Nos: 2 and 12, or alternatively SEQ ID Nos: 2 and 13, or alternatively SEQ ID Nos: 2 and 14, or alternatively SEQ ID Nos: 2 and 15, or alternatively SEQ ID Nos: 3 and 11, or alternatively SEQ ID Nos: 3 and 12, or alternatively SEQ ID Nos: 3 and 13, or alternatively SEQ ID Nos: 3 and 14, or alternatively SEQ ID Nos: 3 and 15, or alternatively SEQ ID Nos: 4 and 11, or alternatively SEQ ID Nos: 4 and 12, or alternatively SEQ ID Nos: 4 and 13, or alternatively SEQ ID Nos: 4 and 14, or alternatively SEQ ID Nos: 4 and 15, or alternatively SEQ ID Nos: 5 and 11, or alternatively SEQ ID Nos: 5 and 12, or alternatively SEQ ID Nos: 5 and 13, or alternatively SEQ ID Nos: 5 and 14, or alternatively SEQ ID Nos: 5 and 15, or alternatively SEQ ID Nos: 6 and 11, or alternatively SEQ ID Nos: 6 and 12, or alternatively SEQ ID Nos: 6 and 13, or alternatively SEQ ID Nos: 6 and 14, or alternatively SEQ ID Nos: 6 and 15, or alternatively SEQ ID Nos: 7 and 11, or alternatively SEQ ID Nos: 7 and 12, or alternatively SEQ ID Nos: 7 and 13, or alternatively SEQ ID Nos: 7 and 14, or alternatively SEQ ID Nos: 7 and 15, or alternatively SEQ ID Nos: 8 and 11, or alternatively SEQ ID Nos: 8 and 12, or alternatively SEQ ID Nos: 8 and 13, or alternatively SEQ ID Nos: 8 and 14, or alternatively SEQ ID Nos: 8 and 15, or alternatively SEQ ID Nos: 9 and 11, or alternatively SEQ ID Nos: 9 and 12, or alternatively SEQ ID Nos: 9 and 13, or alternatively SEQ ID Nos: 9 and 14, or alternatively SEQ ID Nos: 9 and 15, or alternatively SEQ ID Nos: 10 and 11, or alternatively SEQ ID Nos: 10 and 12, or alternatively SEQ ID Nos: 10 and 13, or alternatively SEQ ID Nos: 10 and 14, or alternatively SEQ ID Nos: 10 and 15 or an antigen binding fragment thereof or an equivalent of each thereof.

In some embodiments, the CDRL1 sequence of the light chain variable region comprises, or alternatively consists essentially of, or yet further consists of an amino acid sequence the CDLR1 region of any one of the LC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRL2 sequence of the light chain variable region comprises, or alternatively consists essentially of, or yet further consists of an amino acid sequence the CDLR2 region of any one of the LC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the CDRL3 sequence of the light chain variable region comprises, or alternatively consists essentially of, or yet further consists of an amino acid sequence the CDLR3 region of any one of the LC sequences disclosed herein or equivalents thereof, followed by an additional 50 amino acids, or alternatively about 40 amino acids, or alternatively about 30 amino acids, or alternatively about 20 amino acids, or alternatively about 10 amino acids, or alternatively about 5 amino acids, or alternatively about 4, or 3, or 2 or 1 amino acids at the carboxy-terminus.

In some embodiments, the light chain variable region comprises, or alternatively consists essentially of, or yet further consists of, one of the below noted amino acid sequences: SEQ ID Nos: 11-15 or 26-31 or an antigen binding fragment thereof or an equivalent of each thereof.

In some embodiments, the light chain variable region comprises, or alternatively consists essentially of, or yet further consists of, the polypeptide encoded by one of the below noted polynucleotide sequences: SEQ ID Nos: 41-45 or 48-49 or an antigen binding fragment thereof or an equivalent of each thereof.

In another aspect of the present technology, the isolated antibody includes one or more of the following characteristics:
(a) the light chain immunoglobulin variable domain sequence comprises, or alternatively consists essentially of, or yet further consists of one or more CDRs that are at least 85% identical to a CDR of a light chain variable domain of any of the disclosed light chain sequences;
(b) the heavy chain immunoglobulin variable domain sequence comprises, or alternatively consists essentially of, or yet further consists of one or more CDRs that are at least 85% identical to a CDR of a heavy chain variable domain of any of the disclosed heavy chain sequences;
(c) the light chain immunoglobulin variable domain sequence is at least 85% identical to a light chain variable domain of any of the disclosed light chain sequences;
(d) the HC immunoglobulin variable domain sequence is at least 85% identical to a heavy chain variable domain of any of the disclosed light chain sequences; and
(e) the antibody binds an epitope that overlaps with an epitope bound by any of the disclosed sequences.

In some of the aspects of the antibodies provided herein, the antibody binds DCLK1 with a dissociation constant ($K_D$) or alternatively of less than about 104 M, or alternatively less than about $10^{-5}$ M, or alternatively of less than about $10^{-6}$ M, or alternatively of less than about $10^{-7}$ M, or alternatively of less than about $10^{-8}$ M, or alternatively of less than about $10^{-9}$ M, or alternatively of less than about $10^{-10}$ M, or alternatively of less than about $10^{-11}$ M, or alternatively of less than about or $10^{-12}$ M. In some of the aspects of the antibodies provided herein, the antigen binding site specifically binds to DCLK1.

Antibody Features and Functions

In some of the aspects of the antibodies provided herein, the antibody is soluble Fab.

In some of the aspects of the antibodies provided herein, the HC and LC variable domain sequences are components of the same polypeptide chain. In some of the aspects of the antibodies provided herein, the HC and LC variable domain sequences are components of different polypeptide chains.

In some of the aspects of the antibodies provided herein, the antibody is a full-length antibody. In other aspect, antigen binding fragments of the antibodies are provided.

In some of the aspects of the antibodies provided herein, the antibody is a monoclonal antibody.

In some of the aspects of the antibodies provided herein, the antibody is chimeric or humanized.

In some of the aspects of the antibodies provided herein, the antibody fragment is selected from the group consisting of Fab, F(ab)'2, Fab', scF$_v$, and F$_v$.

In some of the aspects of the antibodies provided herein, the antibody comprises an Fc domain. In some of the aspects of the antibodies provided herein, the antibody is a rabbit antibody. In some of the aspects of the antibodies provided herein, the antibody is a human or humanized antibody or is non-immunogenic in a human. In some of the aspects of the antibodies provided herein comprise a human antibody framework region.

In other aspects, one or more amino acid residues in a CDR of the antibodies provided herein are substituted with another amino acid. The substitution may be "conservative" in the sense of being a substitution within the same family of amino acids. The naturally occurring amino acids may be divided into the following four families and conservative substitutions will take place within those families:

1) Amino acids with basic side chains: lysine, arginine, histidine;
2) Amino acids with acidic side chains: aspartic acid, glutamic acid;
3) Amino acids with uncharged polar side chains: asparagine, glutamine, serine, threonine, tyrosine;
4) Amino acids with nonpolar side chains: glycine, alanine, valine, leucine, isoleucine, proline, phenylalanine, methionine, tryptophan, cysteine.

In another aspect, one or more amino acid residues are added to or deleted from one or more CDRs of an antibody. Such additions or deletions occur at the N or C termini of the CDR or at a position within the CDR.

By varying the amino acid sequence of the CDRs of an antibody by addition, deletion or substitution of amino acids, various effects such as increased binding affinity for the target antigen may be obtained.

It is to be appreciated that antibodies of the present disclosure comprising, or alternatively consisting essentially of, or yet further consisting of such varied CDR sequences still bind DCLK1 with similar specificity and sensitivity profiles as the disclosed antibodies. This may be tested by way of the binding assays.

The constant regions of antibodies may also be varied. For example, antibodies may be provided with Fc regions of any isotype: IgA (IgA1, IgA2), IgD, IgE, IgG (IgG1, IgG2, IgG3, IgG4) or IgM. Non-limiting examples of constant region sequences include: SEQ ID Nos: 60-68 or an equivalent of each thereof.

In some embodiments, the immunoglobulin-related compositions of the present disclosure comprise a heavy chain constant region that is at least 80%, at least 85%, at least 90%, at least 95%, at least 99%, or is 100% identical to SEQ ID Nos: 60-68.

In some aspect, the antibodies comprise, or alternatively consist essentially of, or yet further consist of a heavy chain constant region that is at least 80% identical to any one of those disclosed herein.

In some aspect, the antibodies comprise, or alternatively consist essentially of, or yet further consist of a light chain constant region that is at least 80% identical to any one of those disclosed herein.

In some aspects of the antibodies provided herein, the antibody contains structural modifications to facilitate rapid binding and cell uptake and/or slow release. In some aspect, the DCLK1 antibody contains a deletion in the CH2 constant heavy chain region of the antibody to facilitate rapid binding and cell uptake and/or slow release. In some aspect, a Fab fragment is used to facilitate rapid binding and cell uptake and/or slow release. In some aspect, a F(ab)'2 fragment is used to facilitate rapid binding and cell uptake and/or slow release.

The antibodies, fragments, and equivalents thereof can be combined with a carrier, e.g., a pharmaceutically acceptable carrier or other agents to provide a formulation for use and/or storage.

Further provided is an isolated polypeptide comprising, or alternatively consisting essentially of, or yet further consisting of, the amino acid sequence of DCLK1 or a fragment thereof, that are useful to generate antibodies that bind to DCLK1, as well as isolated polynucleotides that encode them. Also provided herein are isolated polypeptide sequences comprise, or alternatively consist essentially of, or yet further consist of SEQ ID Nos: 1-31.

In one aspect, the isolated polypeptides or polynucleotides further comprise, or alternatively consist essentially of, or yet further consist of a label or selection marker and/or contiguous polypeptide sequences (e.g., keyhole limpet haemocyanin (KLH) carrier protein) or in the case of polynucleotides, polynucleotides encoding the sequence, operatively coupled to polypeptide or polynucleotide. The polypeptides or polynucleotides can be combined with various carriers, e.g., phosphate buffered saline. Further provided are host cells, e.g., prokaryotic or eukaryotic cells, e.g., bacteria, yeast, mammalian (rat, simian, hamster, or human), comprising, or alternatively consisting essentially of, or yet further consisting of the isolated polypeptides or polynucleotides. The host cells can be combined with a carrier.

Yet further provided are the isolated nucleic acids encoding the antibodies and fragments thereof as disclosed herein. In one aspect, the isolated nucleic acids sequences comprise, or alternatively consist essentially of, or yet further consist of SEQ ID Nos: 32-49. They can be combined with a vector or appropriate host cell, and/or a suitable carrier for diagnostic or therapeutic use. In one aspect, the nucleic acids are contained with a host cell for recombinant production of polypeptides and proteins. The host cells can be eukaryotic or prokaryotic.

Processes for Preparing Antibodies

Antibodies, their manufacture and uses are well known and disclosed in, for example, Harlow, E. and Lane, D., Antibodies: A Laboratory Manual, Cold Spring Harbor Laboratory Press, Cold Spring Harbor, N.Y., 1999. The antibodies may be generated using standard methods known in the art. Examples of antibodies include (but are not limited to) monoclonal, single chain, and functional fragments of antibodies. Methods for generating such antibodies are known in the art; see, e.g. Collarini et al. (2009) J. Immunol. 183(10):6338-6345, Carter, P. et al. (1992) Proc. Natl. Acad. Sci. USA 89, 4285-4289, and Baldi L. et al. (2005) Biotechnol. Prog. 21:148-153.

Antibodies may be produced in a range of hosts, for example goats, rabbits, rats, mice, humans, and others. In one aspect, the antibodies are prepared by expression of a polynucleotide encoding the CDRs, e.g., the heavy chain and light chains, as disclosed herein, in a host cell, growing the cells and expressing then then purifying the antibodies expressed by the polynucleotides. The polynucleotides can be inserted into a vector and can further comprise regulatory sequences, e.g., promoters and enhancers selected for the expression system, operatively linked to the polynucleotide encoding the CDRs of the anti-DCKL1 antibody.

Antibodies can be prepared by injection with a target antigen or a fragment or oligopeptide thereof which has immunogenic properties, such as a C-terminal fragment of DCLK1 an isolated polypeptide thereof in the host. Depending on the host species, various adjuvants may be added and used to increase an immunological response. Such adjuvants include, but are not limited to, Freund's, mineral gels such as aluminum hydroxide, and surface-active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful. This this disclosure also provides the isolated polypeptide and an adjuvant.

In certain aspects, the antibodies of the present disclosure are polyclonal, i.e., a mixture of plural types of anti-DCLK1 antibodies having different amino acid sequences. In one aspect, the polyclonal antibody comprises a mixture of plural types of anti-DCLK1 antibodies having different CDRs. As such, a mixture of cells which produce different antibodies is cultured, and an antibody purified from the resulting culture can be used (see WO 2004/061104).

Monoclonal Antibody Production. Monoclonal antibodies to DCLK1 may be prepared using any technique which provides for the production of antibody molecules by continuous cell lines in culture. Such techniques include, but are not limited to, the hybridoma technique (see, e.g., Kohler & Milstein, Nature 256: 495-497 (1975)); the trioma technique; the human B-cell hybridoma technique (see, e.g., Kozbor, et al., Immunol. Today 4: 72 (1983)) and the EBV hybridoma technique to produce human monoclonal antibodies (see, e.g., Cole, et al., in: MONOCLONAL ANTIBODIES AND CANCER THERAPY, Alan R. Liss, Inc., pp. 77-96 (1985)). Human monoclonal antibodies can be utilized in the practice of the present technology and can be produced by using human hybridomas (see, e.g., Cote, et al., Proc. Natl. Acad. Sci. 80: 2026-2030 (1983)) or by transforming human B-cells with Epstein Barr Virus in vitro (see, e.g., Cole, et al., in: MONOCLONAL ANTIBODIES AND CANCER THERAPY, Alan R. Liss, Inc., pp. 77-96 (1985)). For example, a population of nucleic acids that encode regions of antibodies can be isolated. PCR utilizing primers derived from sequences encoding conserved regions of antibodies is used to amplify sequences encoding portions of antibodies from the population and then reconstruct DNAs encoding antibodies or fragments thereof, such as variable domains, from the amplified sequences. Such amplified sequences also can be fused to DNAs encoding other proteins—e.g., a bacteriophage coat, or a bacterial cell surface protein—for expression and display of the fusion polypeptides on phage or bacteria. Amplified sequences can then be expressed and further selected or isolated based, e.g., on the affinity of the expressed antibody or fragment thereof for an antigen or epitope present on the DCLK1 polypeptide.

Alternatively, hybridomas expressing anti-DCLK1 monoclonal antibodies can be prepared by immunizing a subject, e.g., with an isolated polypeptide comprising, or alternatively consisting essentially of, or yet further consisting of, the amino acid sequence of DCLK1 or a fragment thereof, and then isolating hybridomas from the subject's spleen using routine methods. See, e.g., Milstein et al., (Galfre and Milstein, Methods Enzymol 73: 3-46 (1981)). Screening the hybridomas using standard methods will produce monoclonal antibodies of varying specificity (i.e., for different epitopes) and affinity. A selected monoclonal antibody with the desired properties, e.g., DCLK1 binding, can be (i) used as expressed by the hybridoma, (ii) bound to a molecule such as polyethylene glycol (PEG) to alter its properties, or (iii) a cDNA encoding the monoclonal antibody can be isolated, sequenced and manipulated in various ways. In one aspect, the anti-DCLK1 monoclonal antibody is produced by a hybridoma which includes a B cell obtained from a transgenic non-human animal, e.g., a transgenic mouse, having a genome comprising, or alternatively consisting essentially of, or yet further consisting of, a human heavy chain transgene and a light chain transgene fused to an immortalized cell. Hybridoma techniques include those known in the art and taught in Harlow et al., Antibodies: A Laboratory Manual Cold Spring Harbor Laboratory, Cold Spring Harbor, N.Y., 349 (1988); Hammerling et al., Monoclonal Antibodies And T-Cell Hybridomas, 563-681 (1981).

Phage Display Technique. As noted above, the antibodies of the present disclosure can be produced through the application of recombinant DNA and phage display technology. For example, anti-DCLK1 antibodies, can be prepared using various phage display methods known in the art. In phage display methods, functional antibody domains are displayed on the surface of a phage particle which carries polynucleotide sequences encoding them. Phage with a desired binding property is selected from a repertoire or combinatorial antibody library (e.g., human or murine) by selecting directly with an antigen, typically an antigen bound or captured to a solid surface or bead. Phage used in these methods are typically filamentous phage including fd and M13 with Fab, $F_v$, or disulfide stabilized F, antibody domains are recombinantly fused to either the phage gene III or gene VIII protein. In addition, methods can be adapted for the construction of Fab expression libraries (see, e.g., Huse, et al., Science 246: 1275-1281, 1989) to allow rapid and effective identification of monoclonal Fab fragments with the desired specificity for a DCLK1 polypeptide, e.g., a polypeptide or derivatives, fragments, analogs or homologs thereof. Other examples of phage display methods that can be used to make the isolated, humanized antibodies of the present disclosure include those disclosed in Huston et al., Proc. Natl. Acad. Sci. U.S.A., 85: 5879-5883 (1988); Chaudhary et al., Proc. Natl. Acad. Sci. U.S.A., 87: 1066-1070 (1990); Brinkman et al., J. Immunol. Methods 182: 41-50 (1995); Ames et al., J. Immunol. Methods 184: 177-186 (1995); Kettleborough et al., Eur. J. Immunol. 24: 952-958 (1994); Persic et al., Gene 187: 9-18 (1997); Burton et al., Advances in Immunology 57: 191-280 (1994); PCT/GB91/01134; WO 90/02809; WO 91/10737; WO 92/01047; WO 92/18619; WO 93/11236; WO 95/15982; WO 95/20401; WO 96/06213; WO 92/01047 (Medical Research Council et al.); WO 97/08320 (Morphosys); WO 92/01047 (CAT/MRC); WO 91/17271 (Affymax); and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727 and 5,733,743.

Methods useful for displaying polypeptides on the surface of bacteriophage particles by attaching the polypeptides via disulfide bonds have been described by Lohning, U.S. Pat. No. 6,753,136. As described in the above references, after phage selection, the antibody coding regions from the phage can be isolated and used to generate whole antibodies, including human antibodies, or any other desired antigen binding fragment, and expressed in any desired host including mammalian cells, insect cells, plant cells, yeast, and bacteria. For example, techniques to recombinantly produce Fab, Fab' and F(ab')$_2$ fragments can also be employed using methods known in the art such as those disclosed in WO 92/22324; Mullinax et al., BioTechniques 12: 864-869 (1992); Sawai et al., AJRI 34: 26-34 (1995); and Better et al., Science 240: 1041-1043 (1988).

Generally, hybrid antibodies or hybrid antibody fragments that are cloned into a display vector can be selected against the appropriate antigen in order to identify variants that maintained good binding activity, because the antibody or antibody fragment will be present on the surface of the phage or phagemid particle. See e.g. Barbas III et al., Phage Display, A Laboratory Manual (Cold Spring Harbor Laboratory Press, Cold Spring Harbor, N.Y., 2001). However, other vector formats could be used for this process, such as cloning the antibody fragment library into a lytic phage vector (modified T7 or Lambda Zap systems) for selection and/or screening.

Alternate Methods of Antibody Production. Antibodies may also be produced by inducing in vivo production in the lymphocyte population or by screening recombinant immunoglobulin libraries or panels of highly specific binding reagents (Orlandi et al., PNAS 86: 3833-3837 (1989); Winter, G. et al., Nature, 349: 293-299 (1991)).

Alternatively, techniques for the production of single chain antibodies may be used. Single chain antibodies (scF$_v$s) comprise a heavy chain variable region and a light chain variable region connected with a linker peptide (typically around 5 to 25 amino acids in length). Non-limiting examples of such techniques are disclosed in Carter, P. et al. (1992) Proc. Natl. Acad. Sci. USA 89, 4285-4289, and Baldi L. et al. (2005) Biotechnol. Prog. 21:148-153. In the scF$_v$, the variable regions of the heavy chain and the light chain may be derived from the same antibody or different antibodies. scF$_v$s may be synthesized using recombinant techniques, for example by expression of a vector encoding the scF$_v$ in a host organism such as E. coli. DNA encoding scF$_v$ can be obtained by performing amplification using a partial DNA encoding the entire or a desired amino acid sequence of a DNA selected from a DNA encoding the heavy chain or the variable region of the heavy chain of the above-mentioned antibody and a DNA encoding the light chain or the variable region of the light chain thereof as a template, by PCR using a primer pair that defines both ends thereof, and further performing amplification combining a DNA encoding a polypeptide linker portion and a primer pair that defines both ends thereof, so as to ligate both ends of the linker to the heavy chain and the light chain, respectively. An expression vector containing the DNA encoding scF$_v$ and a host transformed by the expression vector can be obtained according to conventional methods known in the art.

Antigen binding fragments may also be generated, for example the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., Science, 256: 1275-1281 (1989)).

Antibody Modifications. The antibodies of the present disclosure may be multimerized to increase the affinity for an antigen. The antibody to be multimerized may be one type of antibody or a plurality of antibodies which recognize a plurality of epitopes of the same antigen. As a method of multimerization of the antibody, binding of the IgG CH3 domain to two scF$_v$ molecules, binding to streptavidin, introduction of a helix-turn-helix motif and the like can be exemplified.

The antibody compositions disclosed herein may be in the form of a conjugate formed between any of these antibodies and another agent (immunoconjugate). In one aspect, the antibodies disclosed herein are conjugated to radioactive material. In another aspect, the antibodies disclosed herein can be bound to various types of molecules such as polyethylene glycol (PEG).

Antibody Screening. Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between DCLK1, or any fragment or oligopeptide thereof and its specific antibody. A two-site, monoclonal-based immunoassay utilizing monoclonal antibodies specific to two non-interfering DCLK1 epitopes may be used, but a competitive binding assay may also be employed (Maddox et al., J. Exp. Med., 158: 1211-1216 (1983)).

Automated immunohistochemistry (IHC) screening of potential anti-DCLK1 antibodies can be performed using a Ventana Medical Systems, Inc (VMSI) Discovery XT and formalin-fixed, paraffin-embedded human tissue on glass slides. Tissue samples first undergo deparaffinization, antigen retrieval, followed by the addition of the potential anti-DCLK1 antibody and a detection antibody. The detection antibody is visualized using a chromogen detection reagent from VMSI. Stained slides are manually screened under a microscope. Samples having a correct primary antibody staining pattern are selected as potential anti-DCLK1 candidates.

Antibody Purification. The antibodies disclosed herein can be purified to homogeneity. The separation and purification of the antibodies can be performed by employing conventional protein separation and purification methods.

By way of example only, the antibody can be separated and purified by appropriately selecting and combining use of chromatography columns, filters, ultrafiltration, salt precipitation, dialysis, preparative polyacrylamide gel electrophoresis, isoelectric focusing electrophoresis, and the like. Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988).

Examples of chromatography include affinity chromatography, ion exchange chromatography, hydrophobic chromatography, gel filtration chromatography, reverse phase chromatography, and adsorption chromatography. In one aspect, chromatography can be performed by employing liquid chromatography such as HPLC or FPLC.

In one aspect, a Protein A column or a Protein G column may be used in affinity chromatography. Other exemplary columns include a Protein A column, Hyper D, POROS, Sepharose F. F. (Pharmacia) and the like.

Methods of Use

General. The antibodies disclosed herein are useful in methods known in the art relating to the localization and/or quantitation of a DCLK1 polypeptide (e.g., for use in measuring levels of the DCLK1 polypeptide within appropriate physiological samples, for use in diagnostic methods, for use in imaging the polypeptide, and the like). The antibodies disclosed herein are useful in isolating a DCLK1 polypeptide by standard techniques, such as affinity chromatography or immunoprecipitation. A DCLK1 antibody disclosed herein can facilitate the purification of natural DCLK1 polypeptides from biological samples, e.g., mammalian sera or cells as well as recombinantly-produced DCLK1 polypeptides expressed in a host system. Non-limiting examples of such techniques are disclosed in Carter, P. et al. (1992) Proc. Natl. Acad. Sci. USA 89, 4285-4289, and Baldi L. et al. (2005) Biotechnol. Prog. 21:148-153. Moreover, DCLK1 antibody can be used to detect a DCLK1 polypeptide (e.g., in plasma, a cellular lysate or cell supernatant) in order to evaluate the abundance and pattern of expression of the polypeptide. The DCLK1 antibodies disclosed herein can be used diagnostically to monitor DCLK1 levels in tissue as part of a clinical testing procedure, e.g., to determine the efficacy of a given treatment regimen. The detection can be facilitated by coupling (i.e., physically linking) the DCLK1 antibodies disclosed herein to a detectable substance.

In another aspect, provided herein is a composition comprising, or alternatively consisting essentially of, or yet further consisting of an antibody or antigen binding fragment as disclosed herein. The composition can further comprise a peptide comprising, or alternatively consisting essentially of, or yet further consisting of, for example, a human DCLK1 protein or a fragment thereof. In one aspect, the peptide is associated with a cell. For example, the composition may comprise, or alternatively consist essentially of, or yet further consist of a disaggregated cell sample labeled with an antibody or antibody fragment as disclosed herein, which composition is useful in, for example, affinity chromatography methods for isolating cells or for flow cytometry-based cellular analysis or cell sorting. As another example, the composition may comprise, or alternatively consist essentially of, or yet further consist of a fixed tissue sample or cell smear labeled with an antibody or antibody fragment as disclosed herein, which composition is useful in, for example, immunohistochemistry or cytology analysis. In another aspect, the antibody or the antibody fragment is bound to a solid support, which is useful in, for example: ELISAs; affinity chromatography or immunoprecipitation methods for isolating DCLK1 proteins or fragments thereof, DCLK1-positive cells, or complexes containing DCLK1 and other cellular components. In another aspect, the peptide is bound to a solid support. For example, the peptide may be bound to the solid support via a secondary antibody specific for the peptide, which is useful in, for example, sandwich ELISAs. As another example, the peptide may be bound to a chromatography column, which is useful in, for example, isolation or purification of antibodies according to the present technology. In another aspect, the peptide is disposed in a solution, such as a lysis solution or a solution containing a sub-cellular fraction of a fractionated cell, which is useful in, for example, ELISAs and affinity chromatography or immunoprecipitation methods of isolating DCLK1 proteins or fragments thereof or complexes containing DCLK1 and other cellular components. In another aspect, the peptide is associated with a matrix, such as, for example, a gel electrophoresis gel or a matrix commonly used for western blotting (such as membranes made of nitrocellulose or polyvinylidene difluoride), which compositions are useful for electrophoretic and/or immunoblotting techniques, such as Western blotting.

Detection of DCLK1 Polypeptides. An exemplary method for detecting the level of DCLK1 polypeptides in a biological sample involves obtaining a biological sample from a subject and contacting the biological sample with a DCLK1 antibody disclosed herein which is capable of detecting the DCLK1 polypeptides. This can be used to monitor treatment or identify subjects for treatment.

In one aspect, the disclosed antibodies or fragments thereof are detectably labeled. The term "labeled", with regard to the antibody is intended to encompass direct labeling of the antibody by coupling (i.e., physically linking) a detectable substance to the antibody, as well as indirect labeling of the antibody by reactivity with another compound that is directly labeled. Non-limiting examples of indirect labeling include detection of a primary antibody using a fluorescently-labeled secondary antibody and end-labeling of a DNA probe with biotin such that it can be detected with fluorescently-labeled streptavidin.

The detection method of the present disclosure can be used to detect expression levels of DCLK1 polypeptides in a biological sample in vitro as well as in vivo. In vitro techniques for detection of DCLK1 polypeptides include enzyme linked immunosorbent assays (ELISAs), Western blots, flow cytometry, immunoprecipitations, radioimmunoassay, and immunofluorescence (e.g., IHC). Furthermore, in vivo techniques for detection of DCLK1 polypeptides include introducing into a subject a labeled anti-DCLK1 antibody. By way of example only, the antibody can be labeled with a radioactive marker whose presence and location in a subject can be detected by standard imaging techniques. In one aspect, the biological sample contains polypeptide molecules from the test subject.

Immunoassay and Imaging. A DCLK1 antibody disclosed herein can be used to assay DCLK1 polypeptide levels in a biological sample (e.g. human plasma) using antibody-based techniques. For example, protein expression in tissues can be studied with classical immunohistochemical (IHC) staining methods. Jalkanen, M. et al., (1985) J. Cell. Biol. 101:976-985; Jalkanen, M. et al., (1987) J. Cell. Biol. 105:3087-3096. Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes or other radioactive agents, such as iodine ($^{125}$I, $^{121}$I, $^{131}$I), carbon ($^{14}$C), sulfur ($^{35}$S), tritium ($^{3}$H), indium ($^{112}$In), and technetium ($^{99}$mTc), and fluorescent labels, such as fluorescein and rhodamine, and biotin.

In addition to assaying DCLK1 polypeptide levels in a biological sample, DCLK1 polypeptide levels can also be detected in vivo by imaging. Labels that can be incorporated with anti-DCLK1 antibodies for in vivo imaging of DCLK1 polypeptide levels include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which can be incorporated into the DCLK1 antibody by labeling of nutrients for the relevant $scF_v$ clone.

A DCLK1 antibody or a polynucleotide encoding the antibody can be labeled with an appropriate detectable imaging moiety, such as a radioisotope (e.g., $^{131}$I, $^{112}$In, $^{99}$mTc), a radio-opaque substance, or a material detectable by nuclear magnetic resonance, is introduced (e.g., parenterally, subcutaneously, or intraperitoneally) into the subject. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$mTc. The labeled DCLK1 antibody will then preferentially accumulate at the location of cells which contain the specific target polypeptide. For example, in vivo tumor imaging is described in S. W. Burchiel et al., Tumor Imaging: The Radiochemical Detection of Cancer 13 (1982).

In some aspect, DCLK1 antibodies containing structural modifications that facilitate rapid binding and cell uptake and/or slow release are useful in in vivo imaging detection methods. In some aspect, the DCLK1 antibody contains a deletion in the CH2 constant heavy chain region of the antibody to facilitate rapid binding and cell uptake and/or slow release. In some aspect, a Fab fragment is used to facilitate rapid binding and cell uptake and/or slow release. In some aspect, a F(ab)'2 fragment is used to facilitate rapid binding and cell uptake and/or slow release.

Diagnostic Uses of DCLK1 Antibodies. The DCLK1 antibody compositions disclosed herein are useful in diagnostic and prognostic methods. As such, the present disclosure provides methods for using the antibodies disclosed herein in the diagnosis of DCLK1-related medical conditions in a subject. Antibodies disclosed herein may be selected such that they have a high level of epitope binding specificity and high binding affinity to the DCLK1 polypeptide. In general, the higher the binding affinity of an antibody, the more stringent wash conditions can be performed in an immunoassay to remove nonspecifically bound material without removing the target polypeptide. Accordingly, DCLK1 antibodies of the present technology useful in diagnostic assays usually have binding affinities of less than or about $10^{-6}$, or alternatively about $10^{-7}$, or alternatively about $10^{-8}$, or alternatively about $10^{-9}$, or alternatively about $10^{-10}$, or alternatively about $10^{-11}$, or 1 or alternatively about $0^{-12}$ M. In certain aspects, DCLK1 antibodies used as diagnostic reagents have a sufficient kinetic on-rate to reach equilibrium under standard conditions in at least 12 hours, at least 5 hours, at least 1 hour, or at least 30 minutes.

Some methods of the present technology employ polyclonal preparations of anti-DCLK1 antibodies and polyclonal anti-DCLK1 antibody compositions as diagnostic reagents, and other methods employ monoclonal isolates. In methods employing polyclonal human anti-DCLK1 antibodies prepared in accordance with the methods described above, the preparation typically contains an assortment of DCLK1 antibodies, e.g., antibodies, with different epitope specificities to the target polypeptide. The monoclonal anti-DCLK1 antibodies of the present disclosure are useful for detecting a single antigen in the presence or potential presence of closely related antigens.

The DCLK1 antibodies of the present disclosure can be used as diagnostic reagents for any kind of biological sample. In one aspect, the DCLK1 antibodies disclosed herein are useful as diagnostic reagents for human biological samples. DCLK1 antibodies can be used to detect DCLK1 polypeptides in a variety of standard assay formats. Such formats include immunoprecipitation, Western blotting, ELISA, radioimmunoassay, flow cytometry, IHC and immunometric assays. See Harlow & Lane, Antibodies, A Laboratory Manual (Cold Spring Harbor Publications, New York, 1988); U.S. Pat. Nos. 3,791,932; 3,839,153; 3,850,752; 3,879,262; 4,034,074, 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Biological samples can be obtained from any tissue (including biopsies), cell or body fluid of a subject.

Prognostic Uses of DCLK1 Antibodies. The present disclosure also provides for prognostic (or predictive) assays for determining whether a subject is at risk of developing a medical disease or condition associated with increased DCLK1 polypeptide expression or activity (e.g., detection of a precancerous cell). Such assays can be used for prognostic or predictive purpose to thereby prophylactically treat an individual prior to the onset of a medical disease or condition characterized by or associated with DCLK1 polypeptide expression.

Another aspect of the present disclosure provides methods for determining DCLK1 expression in a subject to thereby select appropriate therapeutic or prophylactic compounds for that subject.

Alternatively, the prognostic assays can be utilized to identify a subject having or at risk for developing cancer and/or solid tumors. In certain embodiments, the cancer and/or tumor is of the thyroid, breast, colon, prostate, ovary or more specifically a chrio-carcinoma or the caner and/or cancer is a B-cell lymphoma or leukemia. In other embodiments, the cancer and/or tumor is colorectal cancer, pancreatic cancer, fibrosarcoma cells, multiple myeloma or cervical cancer. Thus, the present disclosure provides a method for identifying a disease or condition associated with increased DCLK1 polypeptide expression levels in which a test sample is obtained from a subject and the DCLK1 polypeptide detected, wherein the presence of increased levels of DCLK1 polypeptides compared to a control sample is predictive for a subject having or at risk of developing a disease or condition associated with increased DCLK1 polypeptide expression levels. In some aspect, the disease or condition associated with increased DCLK1 polypeptide expression levels is selected from the group consisting of cancer and/or solid tumors. In certain embodiments, the cancer and/or tumor is of the thyroid, breast, colon, prostate, ovary, or a chrio-carcinoma or a B-cell lymphoma or leukemia. In other embodiments, the cancer and/or tumor is colorectal cancer, pancreatic cancer, fibrosarcoma cells, multiple myeloma or cervical cancer.

In another aspect, the present disclosure provides methods for determining whether a subject can be effectively treated with a compound for a disorder or condition associated with increased DCLK1 polypeptide expression wherein a biological sample is obtained from the subject and the DCLK1 polypeptide is detected using the DCLK1 antibody. The expression level of the DCLK1 polypeptide in the biological sample obtained from the subject is determined and compared with the DCLK1 expression levels found in a biological sample obtained from a subject or Isolated from a patient population who is free of the disease. Elevated levels of the DCLK1 polypeptide in the sample obtained from the subject suspected of having the disease or condition compared with the sample obtained from the healthy subject is indicative of the DCLK1-associated disease or condition in the subject being tested. Increased expression of the DCLK1 polypeptide, as compared to the expression level of the polypeptide or protein in the patient sample(s) from the patients free of disease indicates that the patient is likely to be responsive to the CAR T cell or CAR NK cell therapy of this disclosure, and lack of elevated expression indicates that the patient is not likely to be responsive to the CAR T cell or CAR NK cell therapy. Non-limiting examples of samples include, e.g., any body fluid including, but not limited to, e.g., sputum, serum, plasma, lymph, cystic fluid, urine, stool, cerebrospinal fluid, ascite fluid or blood and including biopsy samples of body tissue. The samples are also a tumor cell. The test sample used in the above-described method will vary based on the assay format, nature of the detection method and the tissues, cells or extracts used as the sample to be assayed.

In a particular aspect, the present disclosure relates to methods for determining if a patient is likely to respond or is not likely to DCLK1 CAR therapy. In specific embodiments, this method comprises, or alternatively consists essentially of, or yet further consists of contacting a tumor sample isolated from the patient with an effective amount of an DCLK1 binding agent, e.g., an DCLK1 antibody and detecting the presence of any agent or antibody bound to the tumor sample. In further embodiments, the presence of agent or antibody bound to the tumor sample indicates that the patient is likely to respond to the DCLK1 CAR therapy and the absence of antibody bound to the tumor sample indicates that the patient is not likely to respond to the DCLK1 therapy. Non-limiting examples of samples include, e.g., any body fluid including, but not limited to, e.g., sputum, serum, plasma, lymph, cystic fluid, urine, stool, cerebrospinal fluid, ascite fluid or blood and including biopsy samples of body tissue. The samples are also a tumor cell. The test sample used in the above-described method will vary based on the assay format, nature of the detection method and the tissues, cells or extracts used as the sample to be assayed. In some embodiments, the method comprises, or alternatively consists essentially of, or yet further consists of the additional step of administering an effective amount of the DCLK1 CAR therapy to a patient that is determined likely to respond to the DCLK1 CAR therapy. In some embodiments, the patient a DCLK1 expressing tumor and/or cancer.

There are a number of disease states in which the elevated expression level of DCLK1 polypeptides is known to be indicative of whether a subject with the disease is likely to respond to a particular type of therapy or treatment. Non-limiting examples of such disease states include cancer, e.g., a carcinoma, a sarcoma or a leukemia. Thus, the method of detecting a DCLK1 polypeptide in a biological sample can be used as a method of prognosis, e.g., to evaluate the likelihood that the subject will respond to the therapy or treatment. The level of the DCLK1 polypeptide in a suitable tissue or body fluid sample from the subject is determined and compared with a suitable control, e.g., the level in subjects with the same disease but who have responded favorably to the treatment. Non-limiting examples of samples include, e.g., any body fluid including, but not limited to, e.g., sputum, serum, plasma, lymph, cystic fluid, urine, stool, cerebrospinal fluid, ascite fluid or blood and including biopsy samples of body tissue. The samples are also a tumor cell. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

In one aspect, the present disclosure provides for methods of monitoring the influence of agents (e.g., drugs, compounds, or small molecules) on the expression of DCLK1 polypeptides. Such assays can be applied in basic drug screening and in clinical trials. For example, the effectiveness of an agent to decrease DCLK1 polypeptide levels can be monitored in clinical trials of subjects exhibiting elevated expression of DCLK1, e.g., patients diagnosed with cancer. An agent that affects the expression of DCLK1 polypeptides can be identified by administering the agent and observing a response. In this way, the expression pattern of the DCLK1 polypeptide can serve as a marker, indicative of the physiological response of the subject to the agent. Accordingly, this response state may be determined before, and at various points during, treatment of the subject with the agent. In some embodiments, the method further comprises, or alternatively consists essentially of, or yet further consists of the additional step of administering an effective amount of the DCLK1 CAR therapy to a patient that is determined to require additional therapy.

Further aspects of the present disclosure relate to methods for determining if a patient is likely to respond or is not likely to DCLK1 CAR therapy. In specific embodiments, this method comprises, or alternatively consists essentially of, or yet further consists of contacting a tumor sample isolated from the patient with an effective amount of an DCLK1 antibody and detecting the presence of any antibody bound to the tumor sample. In further embodiments, the presence of antibody bound to the tumor sample indicates that the patient is likely to respond to the DCLK1 CAR therapy and the absence of antibody bound to the tumor sample indicates that the patient is not likely to respond to the DCLK1 therapy. In some embodiments, the method comprises, or alternatively consists essentially of, or yet further consists of the additional step of administering an effective amount of the DCLK1 CAR therapy to a patient that is determined likely to respond to the DCLK1 CAR therapy. In some embodiments, the patient a B7-H4 expressing tumor and/or cancer. In some embodiments, the tumor and/or cancer is a solid tumor, e.g., breast, colon, prostate, thyroid, or chorio-carcinoma. In some embodiments, the cancer/tumor is a B-cell lymphoma or leukemia. In other embodiments, the cancer and/or tumor is colorectal cancer, pancreatic cancer, fibrosarcoma cells, multiple myeloma or cervical cancer.

Automated Embodiments. A person of ordinary skill in the art will appreciate that aspects of the methods for using the DCLK1 antibodies disclosed herein can be automated. Particular aspects of DCLK1 staining procedures can be conducted using various automated processes.

Therapeutic Application.

The DCLK1 antibody of the present disclosure may be used to treat tumors and cancers. The DCLK1 antibody of the present disclosure may be administered either alone or in combination with diluents, known anti-cancer therapeutics, and/or with other components such as cytokines or other cell populations that are immunostimulatory.

Provided herein is a method of inhibiting the growth of a tumor and/or treating a cancer and/or preventing relapse of cancer in a subject in need thereof, comprising administering to the subject an effective amount of the DCLK1 antibody generated according to any of the methods disclosed herein. In some aspect, the tumor or cancer in a subject in need of treatment expresses or overexpresses DCLK1. In one aspect, the tumor in a subject in need of treatment is a solid tumor.

Accordingly, method aspects of the present disclosure relate to methods for inhibiting the growth of a tumor in a subject in need thereof and/or for treating a cancer patient in need thereof. In some embodiments, the tumor is a solid tumor or a B-cell lymphoma or leukemia. In other embodiments, the tumors/cancer is thyroid, breast, colon, chirocarcinoma, ovarian or prostate tumors/cancer or a B-cell lymphoma or leukemia. In further embodiments, the cancer and/or tumor is colorectal cancer, pancreatic cancer, fibrosarcoma cells, multiple myeloma, cervical cancer, lung cancer, liver cancer, esophageal cancer, breast cancer, major salivary gland carcinoma, neuroblastoma, or renal cell carcinoma. In some embodiments, the tumor or cancer expresses or overexpresses DCLK1. Non-limiting examples of cancers expressing DCLK1 are provided in Westphalen, C. B. et al. "Functional implication of Dclk1 and Dclk1-expressing cells in cancer" Small GTPases, 8(3), 164-171 (2016). Non-limiting examples of cancers or tumors expressing DCLK1 include colo-rectal cancer, pancreatic cancer, prostate cancer, lung cancer, liver cancer, esophageal cancer, breast cancer, major salivary gland carcinoma, neuroblastoma and renal cell carcinoma. In another aspect, the cancer or tumor is characterized as being hyporesponsive.

In a further aspect, the tumor expresses DCLK1 antigen and the subject has been selected for the therapy by a diagnostic, such as the one described herein.

In a further aspect, a method for stimulating an immune response to a cancer or tumor cell population, the method comprising, or alternatively consisting essentially of, or yet further consisting of administering to the subject the DCLK1 antibody of this disclosure in an amount effective to stimulate the immune response. In one aspect, the subject has, has had or is in need of treatment for cancer or tumor. In another aspect, the cancer is characterized as being hyporesponsive. Further provided herein is a method for stimulating an immune response to a cancer or tumor cell, the method comprising, or alternatively consisting essentially of, or yet further consisting of contacting the cancer or tumor cell population with DCLK1 antibody of this disclosure. In a further aspect, a method for stimulating an immune response to a cancer or tumor cell is provided, the method comprising, or alternatively consisting essentially of, or yet further consisting of contacting the target cell population with the DCLK1 antibody, wherein the contacting is in vitro or in vivo. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration. In another aspect, the cancer or tumor is characterized as being hyporesponsive. In one aspect, the DCLK1 antibody is selected for specific binding to the cancer or tumor cell. The cells can be from any species, e.g., a mammalian or a human cell. They can be isolated from a subject (e.g., from a biopsy) or a cultured cell. In another aspect, the cancer or tumor cell express or overexpress DCLK1.

Also provided herein is a method of providing anti-tumor immunity in a subject, the method comprising, or alternatively consisting essentially of, or yet further consisting of administering to the subject DCLK1 antibody of this disclosure, in an amount effective to provide the immunity to the subject. The DCLK1 antibody are provided to prevent the symptoms or cancer from occurring in a subject that is predisposed or does not yet display symptoms of the cancer.

Also disclosed herein is a method for inhibiting the proliferation of cancer cells or cancer stem cells comprising contacting the cells with an effective amount of the DCLK1 antibody. In one aspect, the cancer cells or cancer stem cells that are being inhibited are adherent cancer cells. In another aspect, the cancer cells or cancer stem cells that are being inhibited are non-adherent cancer cells. In a further aspect, the cancer cells or cancer stem cells are colorectal cancer cells, pancreatic cancer cells, fibrosarcoma cells, prostate cancer cells, multiple myeloma cells, cervical cancer cells, or ovarian cancer cells, lung cancer cells, liver cancer cells, esophageal cancer cells, breast cancer cells, major salivary gland carcinoma cells, neuroblastoma cells, or renal cell carcinoma cells The methods are useful to treat subjects such as humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). A mammal can be any age or at any stage of development (e.g., an adult, teen, child, infant, or a mammal in utero). A mammal can be male or female. In certain embodiments the subject has or is suspected of having a neoplastic disorder, neoplasia, tumor, malignancy or cancer.

The DCLK1 antibody as disclosed herein may be administered either alone or in combination with diluents, known anti-cancer therapeutics, and/or with other components such as cytokines or other cell populations that are immunostimulatory. They may be administered as a first line therapy, a second line therapy, a third line therapy, or further therapy. As such, the disclosed DCLK1 antibody may be combined with other therapies (e.g., chemotherapy, radiation, surgery etc.). Non-limiting examples of additional therapies include chemotherapeutics or biologics. Appropriate treatment regimens will be determined by the treating physician or veterinarian.

In some embodiments, the disclosed DCLK1 antibody may be delivered or administered into a cavity formed by the resection of tumor tissue (i.e. intracavity delivery) or directly into a tumor prior to resection (i.e. intratumoral delivery). In some embodiments, the disclosed DCLK1 antibody may be administered intravenously, intrathecally, intraperitoneally, intramuscularly, subcutaneously, or by other suitable means of administration.

Pharmaceutical compositions of the present disclosure may be administered in a manner appropriate to the disease to be treated or prevented. The quantity and frequency of administration will be determined by such factors as the condition of the patient, and the type and severity of the patient's disease, although appropriate dosages may be determined by clinical trials.

For the above methods, an effective amount is administered, and administration of the cell or population serves to attenuate any symptom or prevent additional symptoms from arising. When administration is for the purposes of preventing or reducing the likelihood of cancer recurrence or metastasis, the cell or compositions can be administered in advance of any visible or detectable symptom. Routes of administration include, but are not limited to, oral (such as a tablet, capsule or suspension), topical, transdermal, intranasal, vaginal, rectal, subcutaneous intravenous, intraarterial, intramuscular, intraosseous, intraperitoneal, epidural and intrathecal.

The methods provide one or more of: (1) preventing the symptoms or disease from occurring in a subject that is predisposed or does not yet display symptoms of the disease; (2) inhibiting the disease or arresting its development; or (3) ameliorating or causing regression or relapse of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Treatments containing the disclosed compositions and methods can be first line, second line, third line, fourth line, fifth line therapy and are intended to be used as a sole therapy or in combination with other appropriate therapies e.g., surgical recession, chemotherapy, radiation. In one aspect, treatment excludes prophylaxis.

Kits

As set forth herein, the present disclosure provides diagnostic methods for determining the expression level of DCLK1. In one particular aspect, the present disclosure provides kits for performing these methods as well as instructions for carrying out the methods of the present disclosure such as collecting tissue and/or performing the screen, and/or analyzing the results.

The kit comprises, or alternatively consists essentially of, or yet further consists of, a DCLK1 antibody composition (e.g., monoclonal antibodies) disclosed herein, and instructions for use. The kits are useful for detecting the presence of DCLK1 polypeptides in a biological sample e.g., any bodily fluid including, but not limited to, e.g., sputum, serum, plasma, lymph, cystic fluid, urine, stool, cerebrospinal fluid, acitic fluid or blood and including biopsy samples of body tissue. The test samples may also be a tumor cell, a normal cell adjacent to a tumor, a normal cell corresponding to the tumor tissue type, a blood cell, a peripheral blood lymphocyte, or combinations thereof. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

In some aspect, the kit can comprise, or alternatively consist essentially of, or yet further consist of: one or more DCLK1 antibodies capable of binding a DCLK1 polypeptide in a biological sample (e.g., an antibody or antigen-binding fragment thereof having the same antigen-binding specificity of DCLK1 antibody, means for determining the amount of the DCLK1 polypeptide in the sample; and means for comparing the amount of the DCLK1 polypeptide in the sample with a standard. One or more of the DCLK1 antibodies may be labeled. The kit components, (e.g., reagents) can be packaged in a suitable container. The kit can further comprise, or alternatively consist essentially of, or yet further consist of instructions for using the kit to detect the DCLK1 polypeptides. In certain aspects, the kit can comprise, or alternatively consist essentially of, or yet further consist of a first antibody, e.g., attached to a solid support, which binds to a DCLK1 polypeptide; and, optionally; 2) a second, different antibody which binds to either the DCLK1 polypeptide or the first antibody and is conjugated to a detectable label.

The kit can also comprise, or alternatively consist essentially of, or yet further consist of, e.g., a buffering agent, a preservative or a protein-stabilizing agent. The kit can further comprise, or alternatively consist essentially of, or yet further consist of components necessary for detecting the detectable-label, e.g., an enzyme or a substrate. The kit can also contain a control sample or a series of control samples, which can be assayed and compared to the test sample. Each component of the kit can be enclosed within an individual container and all of the various containers can be within a single package, along with instructions for interpreting the results of the assays performed using the kit. The kits of the present disclosure may contain a written product on or in the kit container. The written product describes how to use the reagents contained in the kit.

As amenable, these suggested kit components may be packaged in a manner customary for use by those of skill in the art. For example, these suggested kit components may be provided in solution or as a liquid dispersion or the like.

Carriers

The antibodies and polynucleotides, vectors, or host cells of the present disclosure also can be bound to many different carriers. Thus, this disclosure also provides compositions containing the antibodies and another substance, active or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the disclosure. Those skilled in the art will know of other suitable carriers for binding antibodies, or will be able to ascertain such, using routine experimentation.

Chimeric Antigen Receptors and Uses Thereof

Compositions

The present disclosure provides chimeric antigen receptors (CAR) that bind to DCLK1 comprising, consisting, or consisting essentially of, a cell activation moiety comprising an extracellular, transmembrane, and intracellular domain. The extracellular domain comprises a target-specific binding element otherwise referred to as the antigen binding domain. The intracellular domain or cytoplasmic domain comprises, at least one costimulatory signaling region and a zeta chain portion.

In one aspect, the present disclosure provides isolated, humanized antibodies, the antibodies comprising, or consisting essentially of, or yet further consisting of a heavy chain (HC) immunoglobulin variable domain sequence and a light chain (LC) immunoglobulin variable domain sequence, wherein the antibody binds to an epitope of DCLK1.

In some aspect, the humanized heavy chain (HC) immunoglobulin variable domain sequence comprises or alternatively consists essentially of, or yet further consists of one or more of the following amino acids sequences: SEQ ID Nos: 1-9 or 16-24 or an equivalent of each thereof.

In another aspect, the heavy chain (HC) immunoglobulin variable domain sequence comprises or alternatively consists essentially of, or yet further consists of one or more of one or more amino acid sequence encoded by the following nucleic acid sequences: SEQ ID Nos: 32-40 or an equivalent of each thereof.

In a further aspect, the light chain (LC) immunoglobulin variable domain sequence comprises or alternatively consists essentially of, or yet further consists of one or more of one or more of the following amino acids sequences: SEQ ID Nos: 11-14 or 26-30 or an equivalent of each thereof.

In a yet further aspect, the light chain (LC) immunoglobulin variable domain sequence comprises or alternatively consists essentially of, or yet further consists of one or more of one or more amino acid sequence encoded by the following nucleic acid sequences: SEQ ID Nos:41-45 or an equivalent of each thereof.

Also provided herein are the heavy chain (HC) immunoglobulin variable domain sequence and the light chain (LC) immunoglobulin variable domain sequence, which are humanized from a murine antibody sequence. In one aspect, the heavy chain (HC) immunoglobulin variable domain sequence of the humanized murine antibody comprises or alternatively consists essentially of, or yet further consists of one or more of the following amino acid sequences: SEQ ID Nos: 10 or 25 or an equivalent of each thereof and/or a sequence encoded by one or more of the following nucleic acid sequences: SEQ ID Nos: 46 or 47 or an equivalent of each thereof.

In another aspect, the light chain (LC) immunoglobulin variable domain sequence of the humanized murine antibody comprises or alternatively consists essentially of, or yet further consists of one or more of the following amino acid sequences: SEQ ID Nos: 15 or 31 or an equivalent of each thereof and/or a sequence encoded by one or more of the following nucleic acid sequences: SEQ ID Nos: 48 or 49 or an equivalent of each thereof.

Aspects of the disclosure relate to a chimeric antigen receptor (CAR) comprising, or consisting essentially of, or yet further consisting of: (a) an antigen binding domain of an anti-DCLK1 antibody; (b) a hinge domain; (c) a transmembrane domain; and (d) an intracellular domain.

Further aspects of the disclosure relate to a chimeric antigen receptor (CAR) comprising, or consisting essentially of, or yet further consisting of: (a) an antigen binding domain of an anti-DCLK1 antibody; (b) a hinge domain; (c) a CD28 transmembrane domain; (d) one or more costimulatory regions selected from a CD28 costimulatory signaling region, a 4-1BB costimulatory signaling region, an ICOS costimulatory signaling region, and an OX40 costimulatory region; and (e) a CD3 zeta signaling domain and alternatives thereof. In a yet further aspect, the present disclosure provides a chimeric antigen receptor (CAR) comprising, or consisting essentially of, or yet further consisting of: (a) an antigen binding domain of an anti-DCLK1 antibody, (b) a CD8 α or an IgG1 hinge domain; (c) a CD8 α transmembrane domain; (d) a CD28 and/or a 4-1BB costimulatory signaling region; and (e) a CD3 zeta signaling domain and alternatives thereof.

Further provided herein is an isolated nucleic acid sequence encoding the heavy chain (HC) immunoglobulin variable domain amino acid sequence comprising, or consisting essentially of, or yet further consisting of a sequence selected from the group of SEQ ID Nos: 1-10 or 16-25 of the humanized anti-DCLK1 antibody, or an equivalent of each thereof. In a further aspect, the present disclosure provides an isolated nucleic acid sequence encoding the light chain (LC) immunoglobulin variable domain amino acid sequence comprising, or consisting essentially of, or yet further consisting of a sequence selected from the group of SEQ ID Nos: 11-15 or 26-31 of the humanized anti-DCLK1 antibody, or an equivalent of each thereof. In another aspect, the present disclosure provides an isolated nucleic acid sequence encoding the anti-DCLK1 antibody, or the anti-DCLK1 CAR construct.

Spacer Domain. The CAR may optionally further comprise, or alternatively consist essentially of, or yet further consist of a spacer domain of up to 300 amino acids, such as (but not limited to) 10 to 100 amino acids, or 25 to 50 amino acids. For example, the spacer may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. A spacer domain may comprise, for example, a portion of a human Fc domain, a CH3 domain, or the hinge region of any immunoglobulin, such as IgA, IgD, IgE, IgG, or IgM, or variants thereof. For example, some embodiments may comprise an IgG4 hinge with or without a S228P, L235E, and/or N297Q mutation (according to Kabat numbering). Additional spacers include, but are not limited to, CD4, CD8, and CD28 hinge regions.

Antigen Binding Domain. In certain aspects, the present disclosure provides a CAR that comprises, consists, or alternatively consists essentially thereof of an antigen binding domain specific DCLK1. In some embodiments, the antigen binding domain comprises, or alternatively consists essentially thereof, or yet consists of the antigen binding domain of an anti-DCLK1 antibody. In further embodiments, the heavy chain variable region and light chain variable region of an anti-DCLK1 antibody comprises, or alternatively consists essentially thereof, or yet consists of the antigen binding domain the anti-DCLK1 antibody. In some embodiments, the antigen binding domain comprises, consists, or consists essentially of a fragment of the target-specific antibody (i.e. an anti-DCLK1 antibody), for example, an scFv. The CAR of this disclosure can further comprise, or alternatively consist essentially of, or yet further consist of an antigen binding domain derived from an antibody against MUC-16 or an antibody against mesothelin.

An scFv region can comprise the variable regions of the heavy ($V_H$) and light chains ($V_L$) of immunoglobulins, connected with a short linker peptide. The linker peptide may be from 1 to 50 amino acids, for instance, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, the linker is glycine rich, although it may also contain serine or threonine.

In some embodiments, the heavy chain variable region of the antibody comprises, or consists essentially thereof, or consists of sequences of those disclosed herein or an equivalent of each thereof and/or comprises one or more CDR regions comprising, or alternatively consisting essentially of, or yet further consisting of sequences of those disclosed herein or an equivalent of each thereof. In some embodiments, the light chain variable region of the antibody comprises, or consists essentially thereof, or consists of sequences of those disclosed herein or an equivalent of each thereof and/or comprises one or more CDR regions comprising, or alternatively consisting essentially of, or yet further consisting of those sequences disclosed herein or an equivalent of each thereof.

Transmembrane Domain. The transmembrane domain may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively, the transmembrane domain may be synthetic, in which case it will comprise predominantly hydrophobic residues such as leucine and valine. In certain particular (but non-limiting) embodiments, a triplet of phenylalanine, tryptophan, and valine will be found at each end of a synthetic transmembrane domain. Optionally, a short oligo- or polypeptide linker, such as (but not limited to) between 2 and 10 amino acids in length, may form the linkage between the transmembrane domain and the cytoplasmic signaling domain of the CAR. A glycine-serine doublet provides a particularly suitable linker.

Cytoplasmic Domain. The cytoplasmic domain or intracellular signaling domain of the CAR is responsible for activation of at least one of the traditional effector functions of an immune cell in which a CAR has been placed. The intracellular signaling domain refers to a portion of a protein which transduces the effector function signal and directs the immune cell to perform its specific function. An entire signaling domain or a truncated portion thereof may be used so long as the truncated portion is sufficient to transduce the effector function signal. Cytoplasmic sequences of the T-cell receptor (TCR) and co-receptors, as well as derivatives or variants thereof, can function as intracellular signaling domains for use in a CAR. Intracellular signaling domains of particular use in this disclosure may be derived from FcR, TCR, CD3, CDS, CD22, CD79a, CD79b, CD66d. In some embodiments, the signaling domain of the CAR comprises, or consists essentially thereof, or consists of a CD3 (signaling domain.

Since signals generated through the TCR are alone insufficient for full activation of a T cell, a secondary or co-stimulatory signal may also be required. Thus, the intracellular region of at least one co-stimulatory signaling molecule, including but not limited to CD27, CD28, 4-IBB (CD 137), OX40, CD30, CD40, PD-1, ICOS, lymphocyte function-associated antigen-1 (LFA-1), CD2, CD7, LIGHT, NKG2C, B7-H3, or a ligand that specifically binds with CD83, may also be included in the cytoplasmic domain of the CAR. CARs of the present disclosure can comprise, or consist essentially thereof, or consist of one or more co-stimulatory domain. For instance, a CAR may comprise, or consist essentially thereof, or consist of one, two, or more co-stimulatory domains, in addition to a signaling domain (e.g., a CD3 (signaling domain).

In some embodiments, the cell activation moiety of the chimeric antigen receptor is a T-cell signaling domain comprising, or alternatively consisting essentially of, or yet further consisting of, one or more proteins or fragments thereof selected from the group consisting of CD8 protein, CD28 protein, 4-1BB protein, OX40, CD30, CD40, PD-1, ICOS, LFA-1, CD2, CD7, CD27, LIGHT, NKG2C, B7-H3 and CD3-zeta protein.

In specific embodiments, the CAR comprises, or alternatively consists essentially thereof, or yet consists of an antigen binding domain of an anti-DCLK1 antibody or fragment (e.g., scFv) thereof, a CD8 α or an IgG1 hinge domain, a CD8 α transmembrane domain, at least one costimulatory signaling region, and a CD3 zeta signaling domain. In further embodiments, the costimulatory signaling region comprises, or alternatively consists essentially thereof, or yet consists of either or both a CD28 costimulatory signaling region and a 4-1BB costimulatory signaling region.

In a particular embodiment, the CAR further comprises, or alternatively consists essentially thereof, or yet consists of a linker polypeptide located between the anti-DCLK1 HC variable region and the anti-DCLK1 LC variable region. In one aspect, the linker polypeptide of the CAR comprises, or alternatively consists essentially thereof, or yet consists of a polypeptide of the sequence (GGGGS)n (SEQ ID NO: 90) wherein n is an integer from 1 to 6.

In some embodiments, the CAR can further comprise, or consist essentially thereof, or consist of a detectable marker or purification marker.

Switch Mechanisms. In some embodiments, the CAR may also comprise, or consist essentially thereof, or consist of a switch mechanism for controlling expression and/or activation of the CAR. For example, a CAR may comprise, consist, or consist essentially of an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises, consists, or consists essentially of a target antigen binding domain (e.g., an anti-DCLK1 antibody or fragment thereof or a bispecific antibody that binds DCLK1 and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233, 125, US 2016/0129109. In this way, a T-cell that expresses the CAR can be administered to a subject, but it cannot bind its target antigen (i.e., DCLK1) until the second composition comprising a DCLK1-specific binding domain is administered.

CARs of the present disclosure may likewise require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015) in order to elicit a T-cell response.

Furthermore, the disclosed CARs can comprise, or consist essentially thereof, or consist of a "suicide switch" to induce cell death of the CAR T-cells following treatment (Buddee et al., PLoS One, 2013) or to downregulate expression of the CAR following binding to the target antigen (WO 2016/011210).

In a further aspect, this disclosure provides complex comprising, or alternatively consisting essentially of, or yet further consisting of an DCLK1 CAR cell bound to its target cell. In a further aspect, the complex is detectably labeled. Detectable labels are known in the art and briefly described herein.

Process for Preparing CARs

Also provided herein is a method of producing DCLK1 CAR expressing cells comprising, or alternatively consisting essentially of, or yet further consisting of the steps: (i) transducing a population of isolated cells with a nucleic acid sequence encoding the CAR as described herein; and (ii) selecting a subpopulation of said isolated cells that have been successfully transduced with said nucleic acid sequence of step (i) thereby producing a DCLK1 CAR expressing cells. In one aspect, the isolated cells are selected from a group consisting of T-cells and NK-cells.

Aspects of the present disclosure relate to an isolated cell comprising, or alternatively consisting essentially of, or yet further consisting of a DCLK1-specific CAR and methods of producing such cells. The cell is a prokaryotic or a eukaryotic cell. In one aspect, the cell is a T cell or an NK cell. The eukaryotic cell can be from any particular species, e.g., an animal cell, a mammalian cell such as a human, a feline, or a canine cell.

In some aspect of the present disclosure, the population of isolated cells transduced with the nucleic acid sequence encoding the CAR as described herein is a population of NK precursor cells and/or T-cell precursor cells. Transduction of precursor cells results in a long-lived population of cells capable of differentiating into CAR T-cells and/or CAR NK cells. T-cell precursors include but are not limited to HSCs; long term HSCs; MPPs; CLPs; LMPPs/ELPs; DN1s; DN2s; DN3s; DN4s; DPs. NK precursors include but are not limited to HSCs, long term HSCs, MPPs, CMPs, GMPs, pro-NK, pre-NK, and iNK cells. In a specific aspect, the population of isolated cells includes both mature T-cells and T-cell precursors to provide both short lived effector CAR T-cells and long-lived CAR T-cell precursors for transplant into the subject. In another aspect, the population of isolated cells includes both mature NK cells and NK precursors to provide both short lived effector CAR NK cells and long-lived CAR NK precursors for transplant into the subject.

In specific embodiments, the isolated cell comprises, or alternatively consists essentially of, or yet further consists of an exogenous CAR comprising, or alternatively consisting essentially of, or yet further consisting of, an antigen binding domain of an anti-DCLK1 antibody, a CD8 α hinge domain, a CD8 α transmembrane domain, a CD28 costimulatory signaling region and/or a 4-1BB costimulatory signaling region, and a CD3 zeta signaling domain. In certain embodiments, the isolated cell is a T-cell, e.g., an animal T-cell, a mammalian T-cell, a feline T-cell, a canine T-cell or a human T-cell. In certain embodiments, the isolated cell is an NK-cell, e.g., an animal NK-cell, a mammalian NK-cell, a feline NK-cell, a canine NK-cell or a human NK-cell.

In certain embodiments, methods of producing DCLK1 CAR expressing cells are disclosed comprising, or alternatively consisting essentially of: (i) transducing a population of isolated cells with a nucleic acid sequence encoding a DCLK1 CAR and (ii) selecting a subpopulation of cells that have been successfully transduced with said nucleic acid sequence of step (i). In some embodiments, the isolated cells are T-cells, an animal T-cell, a mammalian T-cell, a feline T-cell, a canine T-cell or a human T-cell, thereby producing DCLK1 CAR T-cells. In certain embodiments, the isolated cell is an NK-cell, e.g., an animal NK-cell, a mammalian NK-cell, a feline NK-cell, a canine NK-cell or a human NK-cell, thereby producing DCLK1 CAR NK-cells.

In some embodiments, T-cells expressing the disclosed CARs may be further modified to reduce or eliminate expression of endogenous TCRs. Reduction or elimination of endogenous TCRs can reduce off-target effects and increase the effectiveness of the T cells. T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR. Even though some TCR complexes can be recycled to the cell surface when RNA interference is used, the RNA (e.g., shRNA, siRNA, miRNA, etc.) will prevent new production of TCR proteins resulting in degradation and removal of the entire TCR complex, resulting in the production of a T cell having a stable deficiency in functional TCR expression.

Expression of inhibitory RNAs (e.g., shRNA, siRNA, miRNA, etc.) in primary T cells can be achieved using any conventional expression system, e.g., a lentiviral expression system. Although lentiviruses are useful for targeting resting primary T cells, not all T cells will express the shRNAs. Some of these T cells may not express sufficient amounts of the RNAs to allow enough inhibition of TCR expression to alter the functional activity of the T cell. Thus, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3.

Expression of CRISPR in primary T cells can be achieved using conventional CRISPR/Cas systems and guide RNAs specific to the target TCRs. Suitable expression systems, e.g. lentiviral or adenoviral expression systems are known in the art. Similar to the delivery of inhibitor RNAs, the CRISPR system can be used to specifically target resting primary T cells or other suitable immune cells for CAR cell therapy. Further, to the extent that CRISPR editing is unsuccessful, cells can be selected for success according to the methods disclosed above. For example, as noted above, T cells that retain moderate to high TCR expression after viral transduction can be removed, e.g., by cell sorting or separation techniques, so that the remaining T cells are deficient in cell surface TCR or CD3, enabling the expansion of an isolated population of T cells deficient in expression of functional TCR or CD3. It is further appreciated that a CRISPR editing construct may be useful in both knocking out the endogenous TCR and knocking in the CAR constructs disclosed herein. Accordingly, it is appreciated that a CRISPR system can be designed for to accomplish one or both of these purposes.

While many of the above techniques are described with respect to T-cells it is appreciated that the uses and methods of generation and modification described herein and throughout this disclosure are not limited to T-cells but may be expanded to any relevant cell including by not limited to immune cells such as B-cells, NK-cells, and relevant stem cells.

Sources of Isolated Cells. Prior to expansion and genetic modification of the cells disclosed herein, cells may be obtained from a subject—for instance, in embodiments involving autologous therapy—or a commercially available culture, that are available from the American Type Culture Collection (ATCC), for example.

Cells can be obtained from a number of sources in a subject, including peripheral blood mononuclear cells, bone marrow, lymph node tissue, cord blood, thymus tissue, tissue from a site of infection, ascites, pleural effusion, spleen tissue, and tumors.

Methods of isolating relevant cells are well known in the art and can be readily adapted to the present application; an exemplary method is described in the examples below. Isolation methods for use in relation to this disclosure include but are not limited to Life Technologies Dynabeads® system; STEMcell Technologies EasySep™, RoboSep™, RosetteSep™ SepMate™; Miltenyi Biotec MACS™ cell separation kits, and other commercially available cell separation and isolation kits. Particular subpopulations of immune cells and precursors may be isolated through the use of fluorescence-activated cell sorting (FACS), beads, or other binding agents available in such kits specific to unique cell surface markers. For example, MACS™ CD4+ and CD8+ MicroBeads may be used to isolate CD4+ and CD8+ T-cells.

Alternatively, cells may be obtained through commercially available cell cultures, including but not limited to, for T-cells, lines BCL2 (AAA) Jurkat (ATCC® CRL-2902™) BCL2 (S70A) Jurkat (ATCC® CRL-2900™), BCL2 (S87A) Jurkat (ATCC® CRL-2901™) BCL2 Jurkat (ATCC® CRL- 2899™), Neo Jurkat (ATCC® CRL-2898™); and, for NK cells, lines NK-92 (ATCC® CRL-2407™), NK-92MI (ATCC® CRL-2408™)

In some aspect, the subject may be administered a conditioning regimen to induce precursor cell mobilization into the peripheral blood prior to obtaining the cells from the subject. For example, a subject may be administered an effective amount of at least one of granulocyte colony-stimulating factor (G-CSF), filgrastim (Neupogen), sargramostim (Leukine), pegfilgrastim (Neulasta), and mozobil (Plerixafor) up to two weeks prior to or concurrently with isolation of cells from the subject. Mobilized precursor cells can be obtained from the subject by any method known in the art, including, for example, leukapheresis 1-14 days following administration of the conditioning regimen. In some embodiments, specific precursor cell populations are further isolated by Vectors. CARs may be prepared using vectors. Aspects of the present disclosure relate to an isolated nucleic acid sequence encoding a DCLK1 CAR and vectors comprising, or alternatively consisting essentially of, or yet further consisting of an isolated nucleic acid sequence encoding the CAR and its complement and equivalents of each thereof.

The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter and incorporating the construct into an expression vector. The vectors can be suitable for replication and integration eukaryotes.

In some embodiments, the isolated nucleic acid sequence encodes for a CAR comprising, or alternatively consisting essentially of, or yet further consisting of an antigen binding domain of an anti-DCLK1 antibody, a CD8 α hinge domain, a CD8 α transmembrane domain, a CD28 costimulatory signaling region and/or a 4-1BB costimulatory signaling region, and a CD3 zeta signaling domain. In specific embodiments, the isolated nucleic acid sequence comprises, or alternatively consisting essentially thereof, or yet further consisting of, sequences encoding (a) an antigen binding domain of an anti-DCLK1 antibody followed by (b) a CD8 α hinge domain, (c) a CD8 α transmembrane domain followed by (d) a CD28 costimulatory signaling region and/or a 4-1BB costimulatory signaling region followed by (e) a CD3 zeta signaling domain.

In some embodiments, the isolated nucleic acid sequence comprises, or alternatively consists essentially thereof, or yet further consists of, a Kozak consensus sequence upstream of the sequence encoding the antigen binding domain of the anti-DCLK1 antibody or an enhancer. In some embodiments, the isolated nucleic acid comprises, or alternatively consists essentially thereof, or yet further consists of a polynucleotide conferring antibiotic resistance.

In some embodiments, the isolated nucleic acid sequence comprises, or alternatively consists essentially thereof, or yet further consists of a signal peptide encoding polynucleotide sequence located upstream of the antigen binding domain of the anti-DCLK1 antibody.

In one particular embodiments, the isolated nucleic acid sequence comprises, or alternatively consists essentially thereof, or yet further consists of a polynucleotide sequence encoding a 2A self-cleaving peptide (T2A) located upstream of the antigen binding domain of the anti-DCLK1 antibody.

In some embodiments, the isolated nucleic acid sequence is comprised in a vector. In certain embodiments, the vector is a plasmid. In other embodiments, the vector is a viral vector. In specific embodiments, the vector is a lentiviral vector.

The preparation of exemplary vectors and the generation of CAR expressing cells using said vectors is discussed in detail in the examples below. In summary, the expression of natural or synthetic nucleic acids encoding CARs is typically achieved by operably linking a nucleic acid encoding the CAR polypeptide or portions thereof to a promoter and incorporating the construct into an expression vector. The vectors can be suitable for replication and integration eukaryotes. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York).

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type lentivirus. Examples of such, include without limitation, human immunodeficiency virus (HIV), equine infectious anemia virus (EIAV), simian immunodeficiency virus (SIV) and feline immunodeficiency virus (FIV). Alternatively, it is contemplated that other retrovirus can be used as a basis for a vector backbone such murine leukemia virus (MLV). It will be evident that a viral vector according to the disclosure need not be confined to the components of a particular virus. The viral vector may comprise components derived from two or more different viruses and may also comprise synthetic components. Vector components can be manipulated to obtain desired characteristics, such as target cell specificity.

The recombinant vectors of this disclosure may be derived from primates and non-primates. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA, and U5 is derived from the sequence unique to the 5'end of the RNA. The sizes of the three elements can vary considerably among different retroviruses. For the viral genome. and the site of poly (A) addition (termination) is at the boundary between R and U5 in the right-hand side LTR. U3 contains most of the transcriptional control elements of the provirus, which include the promoter and multiple enhancer sequences responsive to cellular and in some cases, viral transcriptional activator proteins.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome.

For the production of viral vector particles, the vector RNA genome is expressed from a DNA construct encoding it, in a host cell. The components of the particles not encoded by the vector genome are provided in trans by additional nucleic acid sequences (the "packaging system", which usually includes either or both of the gag/pol and env genes) expressed in the host cell. The set of sequences required for the production of the viral vector particles may be introduced into the host cell by transient transfection, or they may be integrated into the host cell genome, or they may be provided in a mixture of ways. The techniques involved are known to those skilled in the art.

Retroviral vectors for use in this disclosure include but are not limited to Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by Charité Medical School, Institute of Virology (CBF), Berlin, Germany.

Regardless of the method used to introduce exogenous nucleic acids into a host cell or otherwise expose a cell to the inhibitor of the present disclosure, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the disclosure.

Packaging vector and cell lines. CARs can be packaged into a lentiviral or retroviral packaging system by using a packaging vector and cell lines. The packaging plasmid includes, but is not limited to retroviral vector, lentiviral vector, adenoviral vector, and adeno-associated viral vector. The packaging vector contains elements and sequences that facilitate the delivery of genetic materials into cells. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus. The retroviral DNA sequence lacks the region encoding the native enhancer and/or promoter of the viral 5' LTR of the virus, and lacks both the psi function sequence responsible for packaging helper genome and the 3' LTR, but encodes a foreign polyadenylation site, for example the SV40 polyadenylation site, and a foreign enhancer and/or promoter which directs efficient transcription in a cell type where virus production is desired. The retrovirus is a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. The retroviral packaging plasmid may consist of two retroviral helper DNA sequences encoded by plasmid-based expression vectors, for example where a first helper sequence contains a cDNA encoding the gag and pol proteins of ecotropic MMLV or GALV and a second helper sequence contains a cDNA encoding the env protein. The Env gene, which determines the host range, may be derived from the genes encoding xenotropic, amphotropic, ecotropic, polytropic (mink focus forming) or 10A1 murine leukemia virus env proteins, or the Gibbon Ape Leukemia Virus (GALV env protein, the Human Immunodeficiency Virus env (gp160) protein, the Vesicular Stomatitus Virus (VSV) G protein, the Human T cell leukemia (HTLV) type I and II env gene products, chimeric envelope gene derived from combinations of one or more of the aforementioned env genes or chimeric envelope genes encoding the cytoplasmic and transmembrane of the aforementioned env gene products and a monoclonal antibody directed against a specific surface molecule on a desired target cell.

In the packaging process, the packaging plasmids and retroviral vectors expressing the DCLK1 are transiently co-transfected into a first population of mammalian cells that are capable of producing virus, such as human embryonic kidney cells, for example 293 cells (ATCC No. CRL1573, ATCC, Rockville, Md.), to produce high titer recombinant retrovirus-containing supernatants. In another method of the disclosure this transiently transfected first population of cells is then co-cultivated with mammalian target cells, for example human lymphocytes, to transduce the target cells with the foreign gene at high efficiencies. In yet another method of the disclosure the supernatants from the above described transiently transfected first population of cells are incubated with mammalian target cells, for example human lymphocytes or hematopoietic stem cells, to transduce the target cells with the foreign gene at high efficiencies.

In another aspect, the packaging plasmids are stably expressed in a first population of mammalian cells that are capable of producing virus, such as human embryonic kidney cells, for example 293 cells. Retroviral or lentiviral vectors are introduced into cells by either co-transfection with a selectable marker or infection with pseudotyped virus. In both cases, the vectors integrate. Alternatively, vectors can be introduced in an episomally maintained plasmid. High titer recombinant retrovirus-containing supernatants are produced.

Activation and Expansion of T Cells. Whether prior to or after genetic modification of the T cells to express a desirable CAR, the cells can be activated and expanded using generally known methods such as those described in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041. Stimulation with the DCLK1 antigen ex vivo can activate and expand the selected CAR expressing cell subpopulation. Alternatively, the cells may be activated in vivo by interaction with DCLK1 antigen.

Methods of activating relevant cells are well known in the art and can be readily adapted to the present application; an exemplary method is described in the examples below. Isolation methods for use in relation to this disclosure include but are not limited to Life Technologies Dynabeads® system activation and expansion kits; BD Biosciences Phosflow™ activation kits, Miltenyi Biotec MACS™ activation/expansion kits, and other commercially available cell kits specific to activation moieties of the relevant cell. Particular subpopulations of immune cells may be activated or expanded through the use of beads or other agents available in such kits. For example, α-CD3/α-CD28 Dynabeads® may be used to activate and expand a population of isolated T-cells Methods of Use Therapeutic Application. The CAR T-cells of the present disclosure may be used to treat tumors and cancers. The CAR-T cells of the present disclosure may be administered either alone or in combination with diluents, known anti-cancer therapeutics, and/or with other components such as cytokines or other cell populations that are immunostimulatory.

Provided herein is a method of inhibiting the growth of a tumor and/or treating a cancer and/or preventing relapse of cancer in a subject in need thereof, comprising administering to the subject an effective amount of the anti-DCLK1 CAR expressing cells generated according to any of the methods disclosed herein. In some embodiments, the anti-DCLK1 CAR expressing cells are autologous or allogenic to the subject being treated. In some aspect, the tumor or cancer in a subject in need of treatment expresses or overexpresses DCLK1. In one aspect, the tumor in a subject in need of treatment is a solid tumor.

Accordingly, method aspects of the present disclosure relate to methods for inhibiting the growth of a tumor in a subject in need thereof and/or for treating a cancer patient in need thereof. In some embodiments, the tumor is a solid tumor or a B-cell lymphoma or leukemia. In other embodiments, the tumors/cancer is thyroid, breast, colon, chirocarcinoma, ovarian or prostate tumors/cancer or a B-cell lymphoma or leukemia. In further embodiments, the cancer and/or tumor is colorectal cancer, pancreatic cancer, fibrosarcoma cells, multiple myeloma, cervical cancer, lung cancer, liver cancer, esophageal cancer, breast cancer, major salivary gland carcinoma, neuroblastoma, or renal cell carcinoma. In some embodiments, the tumor or cancer expresses or overexpresses DCLK1. Non-limiting examples of cancers expressing DCLK1 are provided in Westphalen, C. B. et al. "Functional implication of Dclk1 and Dclk1-expressing cells in cancer" Small GTPases, 8(3), 164-171 (2016). Non-limiting examples of cancers or tumors expressing DCLK1 include colo-rectal cancer, pancreatic cancer, prostate cancer, lung cancer, liver cancer, esophageal cancer, breast cancer, major salivary gland carcinoma, neuroblastoma and renal cell carcinoma. In another aspect, the cancer or tumor is characterized as being hyporesponsive.

In certain embodiments, these methods comprise, or alternatively consist essentially of, or yet further consist of, administering to the subject or patient an effective amount of the isolated cell. In further embodiments, this isolated cell comprises, or alternatively consists essentially thereof, or yet further consists of a DCLK1 CAR. In still further embodiments, the isolated cell is a T-cell or an NK cell. In some embodiments, the isolated cell is autologous to the subject or patient being treated. In a further aspect, the tumor expresses DCLK1 antigen and the subject has been selected for the therapy by a diagnostic, such as the one described herein.

In a further aspect, a method for stimulating an immune response to a cancer or tumor cell population, the method comprising, or alternatively consisting essentially of, or yet further consisting of administering to the subject the anti-DCLK1 CAR expressing cells of this disclosure in an amount effective to stimulate the immune response. In one aspect, the subject has, has had or is in need of treatment for cancer or tumor. In another aspect, the cancer is characterized as being hyporesponsive. Further provided herein is a method for stimulating an immune response to a cancer or tumor cell, the method comprising, or alternatively consisting essentially of, or yet further consisting of contacting the cancer or tumor cell population with the anti-DCLK1 CAR expressing cells of this disclosure. In a further aspect, a method for stimulating an immune response to a cancer or tumor cell is provided, the method comprising, or alternatively consisting essentially of, or yet further consisting of contacting the target cell population with the anti-DCLK1 CAR expressing cells of this disclosure, wherein the contacting is in vitro or in vivo. A particular example of direct interaction is binding. A particular example of an indirect interaction is where one entity acts upon an intermediary molecule, which in turn acts upon the second referenced entity. Contacting as used herein includes in solution, in solid phase, in vitro, ex vivo, in a cell and in vivo. Contacting in vivo can be referred to as administering, or administration. In another aspect, the cancer or tumor is characterized as being hyporesponsive. In one aspect, the anti-DCLK1 CAR expressing cell is selected for specific binding to the cancer or tumor cell. The cells can be from any species, e.g., a mammalian or a human cell. They can be isolated from a subject (e.g., from a biopsy) or a cultured cell. In another aspect, the cancer or tumor cell express or overexpress DCLK1.

Also provided herein is a method of providing anti-tumor immunity in a subject, the method comprising, or alternatively consisting essentially of, or yet further consisting of administering to the subject DCLK1 CAR expressing cells of this disclosure, in an amount effective to provide the immunity to the subject. The DCLK1 CAR expressing cells are provided to prevent the symptoms or cancer from occurring in a subject that is predisposed or does not yet display symptoms of the cancer.

Also disclosed herein is a method for inhibiting the proliferation of cancer cells or cancer stem cells comprising contacting the cells with an effective amount of the anti-DCLK1 CAR expressing cells. In one aspect, the cancer cells or cancer stem cells that are being inhibited are adherent cancer cells. In another aspect, the cancer cells or cancer stem cells that are being inhibited are non-adherent cancer cells. In a further aspect, the cancer cells or cancer stem cells are colorectal cancer cells, pancreatic cancer cells, fibrosarcoma cells, prostate cancer cells, multiple myeloma cells, cervical cancer cells, or ovarian cancer cells, lung cancer cells, liver cancer cells, esophageal cancer cells, breast cancer cells, major salivary gland carcinoma cells, neuroblastoma cells, or renal cell carcinoma cells The methods are useful to treat subjects such as humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). A mammal can be any age or at any stage of development (e.g., an adult, teen, child, infant, or a mammal in utero). A mammal can be male or female. In certain embodiments the subject has or is suspected of having a neoplastic disorder, neoplasia, tumor, malignancy or cancer.

The CAR cells as disclosed herein may be administered either alone or in combination with diluents, known anti-cancer therapeutics, and/or with other components such as cytokines or other cell populations that are immunostimulatory. They may be administered as a first line therapy, a second line therapy, a third line therapy, or further therapy. As such, the disclosed CARs may be combined with other therapies (e.g., chemotherapy, radiation, surgery etc.). Non-limiting examples of additional therapies include chemotherapeutics or biologics. Appropriate treatment regimens will be determined by the treating physician or veterinarian.

In some embodiments, the disclosed CARs may be delivered or administered into a cavity formed by the resection of tumor tissue (i.e. intracavity delivery) or directly into a tumor prior to resection (i.e. intratumoral delivery). In some embodiments, the disclosed CARs may be administered intravenously, intrathecally, intraperitoneally, intramuscularly, subcutaneously, or by other suitable means of administration.

Pharmaceutical compositions of the present disclosure may be administered in a manner appropriate to the disease to be treated or prevented. The quantity and frequency of administration will be determined by such factors as the condition of the patient, and the type and severity of the patient's disease, although appropriate dosages may be determined by clinical trials.

For the above methods, an effective amount is administered, and administration of the cell or population serves to attenuate any symptom or prevent additional symptoms from arising. When administration is for the purposes of preventing or reducing the likelihood of cancer recurrence or metastasis, the cell or compositions can be administered in advance of any visible or detectable symptom. Routes of administration include, but are not limited to, oral (such as a tablet, capsule or suspension), topical, transdermal, intranasal, vaginal, rectal, subcutaneous intravenous, intraarterial, intramuscular, intraosseous, intraperitoneal, epidural and intrathecal.

The methods provide one or more of: (1) preventing the symptoms or disease from occurring in a subject that is predisposed or does not yet display symptoms of the disease; (2) inhibiting the disease or arresting its development; or (3) ameliorating or causing regression or relapse of the disease or the symptoms of the disease. As understood in the art, "treatment" is an approach for obtaining beneficial or desired results, including clinical results. For the purposes of the present technology, beneficial or desired results can include one or more, but are not limited to, alleviation or amelioration of one or more symptoms, diminishment of extent of a condition (including a disease), stabilized (i.e., not worsening) state of a condition (including disease), delay or slowing of condition (including disease), progression, amelioration or palliation of the condition (including disease), states and remission (whether partial or total), whether detectable or undetectable. Treatments containing the disclosed compositions and methods can be first line, second line, third line, fourth line, fifth line therapy and are intended to be used as a sole therapy or in combination with other appropriate therapies e.g., surgical recession, chemotherapy, radiation. In one aspect, treatment excludes prophylaxis.

Carriers

Additional aspects of the disclosure relate to compositions comprising, or alternatively consisting essentially thereof, or yet further consisting of a carrier and one or more of the products—e.g., an isolated cell comprising, or alternatively consisting essentially thereof, or yet further consisting of a DCLK1 CAR, an isolated nucleic acid, a vector, an isolated cell of any anti-DCLK1 antibody or CAR cell, an anti-DCLK1—described in the embodiments disclosed herein.

Briefly, pharmaceutical compositions of the present disclosure including but not limited to any one of the claimed compositions may comprise, or alternatively consist essentially thereof, or yet further consist of a target cell population as described herein, in combination with one or more pharmaceutically or physiologically acceptable carriers, diluents or excipients. Such compositions may comprise, or alternatively consist essentially thereof, or yet further consist of buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Administration of the cells or compositions can be effected in one dose, continuously or intermittently throughout the course of treatment. Methods of determining the most effective means and dosage of administration are known to those of skill in the art and will vary with the composition used for therapy, the purpose of the therapy and the subject being treated. Single or multiple administrations can be carried out with the dose level and pattern being selected by the treating physician. Suitable dosage formulations and methods of administering the agents are known in the art. In a further aspect, the cells and composition of the disclosure can be administered in combination with other treatments.

The cells and populations of cell are administered to the host using methods known in the art and described, for example, in PCT/US2011/064191. This administration of the cells or compositions of the disclosure can be done to generate an animal model of the desired disease, disorder, or condition for experimental and screening assays.

Additional aspects of the disclosure relate to compositions comprising, or alternatively consisting essentially thereof, or yet further consisting of a carrier and one or more of the products—e.g., an isolated cell comprising, or alternatively consisting essentially thereof, or yet further consisting of a DCLK1 CAR, an isolated nucleic acid, a vector, an isolated cell of any anti-DCLK1 antibody or CAR cell, an anti-DCLK1—described in the embodiments disclosed herein.

Briefly, pharmaceutical compositions of the present disclosure including but not limited to any one of the claimed compositions may comprise, or alternatively consist essentially thereof, or yet further consist of a target cell population as described herein, in combination with one or more pharmaceutically or physiologically acceptable carriers, diluents or excipients. Such compositions may comprise, or alternatively consist essentially thereof, or yet further consist of buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure may be formulated for oral, intravenous, topical, enteral, and/or parenteral administration. In certain embodiments, the compositions of the present disclosure are formulated for intravenous administration.

Briefly, pharmaceutical compositions of the present disclosure including but not limited to any one of the claimed compositions may comprise, or alternatively consist essentially thereof, or yet further consist of a target cell population as described herein, in combination with one or more pharmaceutically or physiologically acceptable carriers, diluents or excipients. Such compositions may comprise, or alternatively consist essentially thereof, or yet further consist of buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In certain particular (but non-limiting) embodiments, the compositions of the present disclosure are formulated for intravenous administration.

Pharmaceutical compositions of the present disclosure may be administered in a manner appropriate to the disease to be treated or prevented. The quantity and frequency of administration will be determined by such factors as the condition of the patient, and the type and severity of the patient's disease, although appropriate dosages may be determined by clinical trials.

The following examples are illustrative of procedures which can be used in various instances in carrying the disclosure into effect.

EXAMPLES

Example 1—Generation of Humanized Antibodies

Humanized antibodies were designed by creating multiple hybrid sequences that fuse select parts of the parental antibody sequence with the human framework sequences. Using the 3D model, these humanized sequences were methodically analyzed by eye and computer modeling to isolate the sequences that would most likely retain antigen binding. The goal was to maximize the amount of human sequence in the final humanized antibodies while retaining the original antibody specificity.

Three humanized light chains and three humanized heavy chains were designed based on two different heavy and light chain human acceptor frameworks (see Table 1). The first humanized chain for each utilizes the first respective framework and contains the most human sequence with minimal parental antibody framework sequence (HC 1, LC 1). The second humanized chain for each uses the same framework as before but contains additional parental sequences (HC 2, LC 2). The third humanized chain for each utilizes the second respective framework and, similar to HC 2/LC 2, also contain additional parental sequences fused with the human framework (HC 3, LC 3).

TABLE 1

Humanized chain information table

| Chain Name | Chain Type | Acceptor Framework |
|---|---|---|
| H6166 (chimeric parental) | hIgG1 | |
| L6165 (chimeric parental) | Light chain | |

TABLE 1-continued

Humanized chain information table

| Chain Name | Chain Type | Acceptor Framework |
|---|---|---|
| 6258 (Humanized HC 1) | Heavy chain | HC framework 1 |
| 6259 (Humanized HC 3) | Heavy chain | HC framework 1 |
| 6260 (Humanized HC 3) | Heavy chain | HC framework 2 |
| 6258 (Humanized LC 1) | Light chain | LC framework 1 |
| 6259 (Humanized LC 3) | Light chain | LC framework 1 |
| 6260 (Humanized LC 3) | Light chain | LC framework 2 |

This light and heavy humanized chains are combined to create variant fully humanized antibodies. Combinations thereof were tested for their expression level and antigen binding affinity to identify antibodies that perform similar to the chimeric parental antibody from which they were derived.

"Humanness" scores were calculated according to the method described in Gao et al. (2013) "Monoclonal antibody humanness score and its applications." BMC Biotechnology 13:55. This score represents how human-like an antibody variable region sequence looks, which is an important factor when humanizing antibodies. The humanness scores for the parental and humanized antibodies are shown below. Based on our method, for heavy chains a score of 79 or above is indicative of looking human-like; for kappa light chains a score of 86 or above is indicative of looking human-like.

TABLE 2

Humanness score calculated for all humanized chains.

| VH | Full-length (Framework + CDR) Cutoff = 79 | Framework Only Cutoff = 84 |
|---|---|---|
| Parental H6166 | 75.1 | 76.3 |
| H6258 | 87.4 | 91.2 |
| H6259 | 86.6 | 90.1 |
| H6260 | 86.6 | 88.8 |

| VL | Full-length (Framework + CDR) Cutoff = 86 | Framework Only Cutoff = 90 |
|---|---|---|
| Parental L6165 | 84.6 | 83.5 |
| L6258 | 96.0 | 99.4 |
| L6259 | 95.1 | 98.2 |
| L6260 | 94.4 | 97.9 |

Full-length antibody genes were constructed by first synthesizing the variable region sequences. The sequences were optimized for expression in mammalian cells. These variable region sequences were then cloned into expression vectors that already contain human Fc domains. In addition, for comparison the variable regions of the parental heavy and light chains were constructed as full-length chimeric chains using the same backbone Fc sequences.

The humanized antibodies then underwent 0.03 liter production. The chimeric parental antibody was also scaled-up for direct comparison. Plasmids for the indicated heavy and light chains were transfected into suspension HEK293 cells using chemically defined media in the absence of serum to make the antibodies. Whole antibodies in the conditioned media were purified using MabSelect SuRe Protein A medium (GE Healthcare). The results with the tested antibodies are shown herein below.

TABLE 3

Ten antibodies produced in HEK293 cells transiently using hIgG/Kappa backbone.

| Antibody name | Heavy Chain | Light Chain | PP # | Titer (mg/L) |
|---|---|---|---|---|
| Chimeric parental | H6166 | L6165 | 9987 | 88 |
| Humanized HC1 + LC1 | H6258 | L6258 | 9988 | 75 |
| Humanized HC1 + LC2 | H6258 | L6259 | 9989 | 69 |
| Humanized HC1 + LC3 | H6258 | L6260 | 9990 | 75 |
| Humanized HC2 + LC1 | H6259 | L6258 | 9991 | 66 |
| Humanized HC2 + LC2 | H6259 | L6259 | 9992 | 65 |
| Humanized HC2 + LC3 | H6259 | L6260 | 9993 | 62 |
| Humanized HC3 + LC1 | H6260 | L6258 | 9994 | 62 |
| Humanized HC3 + LC2 | H6260 | L6259 | 9995 | 71 |
| Humanized HC3 + LC3 | H6260 | L6260 | 9996 | 66 |

Octect analysis was also performed. All experiments were performed on the Octet Red96 system (ForteBio). In the assay format, Anti-Human IgG Fc Capture (AHC) kinetic grade biosensors (ForteBio, #18-5064) were hydrated in assay buffer and preconditioned in pH 1.7 Glycine. Each antibody was immobilized onto the AHC biosensors at a concentration of 10 μg/mL for 180 seconds. A short baseline (60 seconds) was established using dissociation buffer after AHC loading ensure the antibody was stably bound to the biosensor. The antibody-loaded AHC biosensors were then dipped into an 8-point, 1:3 dilution series of the antigen starting from 300 nM. The last dilution point of the analyte column contained only assay buffer to test for non-specific binding between the buffer and the loaded biosensors. Association was observed for 180 seconds, followed by 300 seconds of dissociation. Parallel references were recorded by using an unloaded bare sensor dipped into the same 8-point dilution series of the antigen. During data processing, double reference was used for normalization. The binding affinity of the antigen to each antibody was characterized by fitting kinetic sensorgrams to a monovalent binding model (1:1 binding). FIG. 1.

Additional humanized sequences were generated and are tested according to similar means.

Example 2—Antibody Humanization and Testing

CBT-15A VH is a mouse germline $VH_{5-6-2}$. Human $VH_{3-23}$ was chosen as a "acceptor" framework for CDR grafting. CBT-15A VK is a mouse germline $VK_{8-20}$. Human $VK_{4-1}$ was chosen as an "acceptor" framework for CDR grafting.

The humanized VHs were aligned as follows (SEQ ID NOS 91, 92, and 4-9, respectively, in order of appearance):

```
CBT-15A    DVKLVESGGGLVKLGGSLKLSCAASGFTFSSYYMSWVRQTPEKRLELVAAINSNGGSTYYPDTVKG
VH3-23     EVQLVESGGGLVQPGGSLRLSCAASGFTFSSYAMSKVRQAPGKGLEWYSAISGSGGSTYYADSVKG
H1         EVQLVESGGGLVQPGGSLRLSCAASGFTFSSYYMHVRQAPGKGLEWYSAINSNGGSTYYPDTVKG
H2         EVQLVESGGGLVQPGGSLRLSCAASGFTFSSYYMSWVRQAPGKGLEWVSAINSNGGSTYYPDTVKG
H3         EVQLVESGGGLVQPGGSLRLSCAASGFTFSSYYMSKVRQAPGKGLEWVAAINSNGGSTYYPDTVKG
H4         EVQLVESGGGLVQPGGSLRLSCAASGFTFSSYYMSWVRQAPGKGLELVAAINSNGGSTYYPDTVKG
H5         EVQLVESGGGLYQPGGSLRLSCAASGFTFSSYYMSKVRQAPGKGLEWYSAINSSGGSTYYADSVKG
H6         EVQLVESGGGLVQPGGSLRLSCAASGFTFSSYYMSWVRQAPGKGLELVAAINSSGGSTYYPDSVKG

CBT-15A    RFTISRDNAKNTLYLQMSSLKSEDTALYYCARHGGNYWYFDVWGAGTTVTVSS
VH3-23     RFTISRDNSKNTLYLQHNSLRAEDTAVYYCAK
H1         RFTISRDNSKNTLYLQHNSLRAEDTAVYYCAKHGGNYWYFDVWGQGTLVTVSS
H2         RFTISRDNSKNTLYLQHNSLRAEDTAVYYCARHGGNYWYFDVWGQGTLVTVSS
H3         RFTISRDNSKNTLYLQHNSLRAEDTAVYYCARHGGNYWYFDVWGQGTLVTVSS
H4         RFTISRDNSKNTLYLQHNSLRAEDTAVYYCARHGGNYWYFDVWGQGTLVTVSS
H5         RFTISRDNSKNTLYLQHNSLRAEDTAVYYCARHGGNYWYFDVWGQGTLVTVSS
H6         RFTISRDNSKNTLYLQHNSLRAEDTAVYYCARHGGNYWYFDVWGQGTLVTVSS
```

$VH_{3-23}$ with $JH_4$ was the human germline acceptor. H1-6 are humanized VH variants containing 0-3 back mutations. The NG motif, present in CDR-H2, shows a high deamidation propensity.

The humanized VKs were aligned as follows (SEQ ID NOS 93, 94, 13, and 14, respectively, in order of appearance):

```
CBT-15A    DIVMSQSPSSLAVSVGEKVTMSCKSSQSLLYSSNQKNYLAWYQQKPGQSPKLLIYWASTRES
VK4-1      DIVATQSPDSLAVSLGERATINCKSSQSVLYSSNNKNYLAWYQQKPGQPPKLLIYWASTRES
L1         DIVATQSPDSLAVSLGERATINCKSSQSLLYSSNQKNYLAWYQQKPGQPPKLLIYWASTRES
L2         DIVASQSPDSLAVSLGERATISCKSSQSLLYSSNQKNYLAWYQQKPGQPPKLLIYWASTRES

CBT-15A    GVPDRFTGSGSGTDFTLTISSVKAEDLAVYYCQQYYSYPYTFGGGTKLEIK
VK4-1      GVPDRFSGSGSGTDFTLTISSLQAEDVAVYYCQQYYSTP
L1         GVPDRFSGSGSGTDFTLTISSLQAEDVAVYYCQQYYSYPYTFGQGTKLEIK
L2         GVPDRFSGSGSGTDFTLTISSLQWEDVAVYYCQQYYSYPYTFGQGTKLEIK
```

VK$_{4-1}$ with JK2 was the human germline acceptor. L1-2 are humanized VH variants. L2 and L2 contain 0 and 2 back mutations, respectively.

Table 4 shows the cloning of humanized CBT-15A variants, including the plasmid, VH/VK and CH/CK domains used, the promoter sequence, and the selection marker used:

TABLE 4

| Plasmid | VH/VK | CH/CK | Promoter | Selection |
|---|---|---|---|---|
| LB374 | CBT-15A_VH | hIgG$_1$ CH | hEF1α | Puromycin |
| LB375 | CBT-15A-VK | hCK | hEF1α | Neomycin |
| LB376-L$_1$ | CBT-15A_L1 | hCK | hEF1α | Neomycin |
| LB376-L$_2$ | CBT-15A_L2 | hCK | hEF1α | Neomycin |
| LB384 | CBT-15A_H1 | hIgG$_1$ CH | hEF1α | Puromycin |
| LB386-H$_2$ | CBT-15A_H2 | hIgG$_1$ CH | hEF1α | Puromycin |
| LB386-H$_3$ | CBT-15A_H3 | hIgG$_1$ CH | hEF1α | Puromycin |
| LB386-H$_4$ | CBT-15A_H4 | hIgG$_1$ CH | hEF1α | Puromycin |
| LB386-H$_5$ | CBT-15A_H5 | hIgG$_1$ CH | hEF1α | Puromycin |
| LB386-H$_6$ | CBT-15A_H6 | hIgG$_1$ CH | hEF1α | Puromycin |

To assess transient production in 293 cells, 100 mL of 293F cells were transfected with Freestyle Max (Invitrogen) and the condition media was harvested after 4 days. The antibodies were purified using a protein-A column. As shown in Table 5 and Table 6 below, antibody expression with CB15-A H5 was very low.

TABLE 5

| Plasmid 1 | Plasmid 2 | Purification (mg) |
|---|---|---|
| LB374 | LB375 | 0.5 |
| LB376-L1 | LB384 | 0.4 |
| LB376-L1 | LB386-H2 | 0.2 |
| LB376-L1 | LB386-H3 | 0.1 |
| LB376-L1 | LB386-H4 | 0.1 |
| LB376-L1 | LB386-H5 | ~0 |
| LB376-L1 | LB386-H6 | 0.8 |

TABLE 6

| Plasmid 1 | Plasmid 2 | Purification (mg) |
|---|---|---|
| LB376-L2 | LB384 | 0.4 |
| LB376-L2 | LB386-H2 | 0.2 |
| LB376-L2 | LB386-H3 | 0.8 |
| LB376-L2 | LB386-H4 | 0.8 |
| LB376-L2 | LB386-H5 | ~0 |
| LB376-L2 | LB386-H6 | 0.8 |

Figure 2:
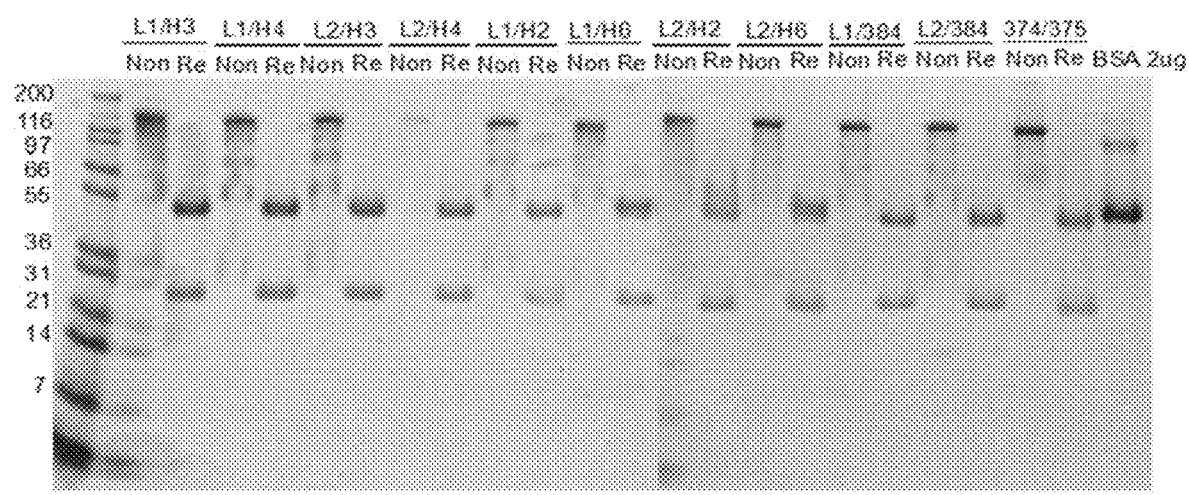
FIG. 2 shows an SDS-PAGE gel run with the 2 μg of each of the various humanized CBT-15A antibodies in reducing and non-reducing conditions.

FIG. 2 shows the results of an SDS-PAGE gel run with the 2 μg of each of the various humanized CBT-15A antibodies in reducing and non-reducing conditions.

Figure 3:
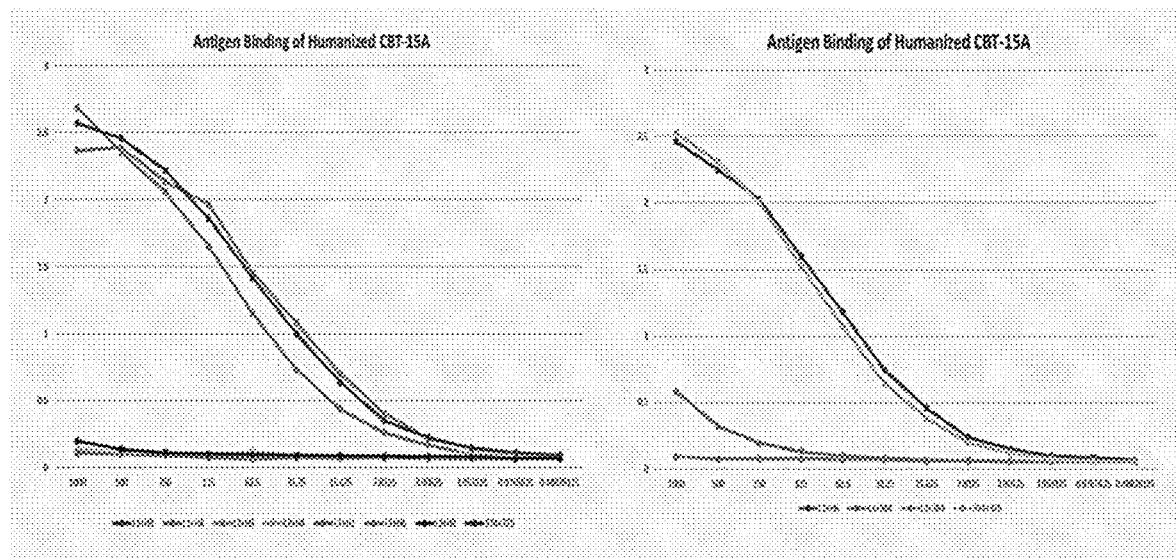
FIG. 3 shows antigen binding of the various anti-DCKL1 antibodies on ELISA.

An ELISA place was coated with DCLK1 C-terminal peptide (150 ng/well) and a 2-fold dilution of humanized CBT15A (1 μg/mL) was added to the ELISA plate. CBT 15-A chimeric 374/375 was used as a positive control. Antigen binding was detected with anti-human kappa HRP. L1/H4 and L2/H6 exhibited similar strong binding as the chimeric CBT-15A with an EC$_{50}$ of ~50 ng/mL (350 pM). L1/H6 exhibited a little bit weaker binding with an EC$_{50}$ of ~60 ng/mL (420 pM). FIG. 3.

Figure 4:
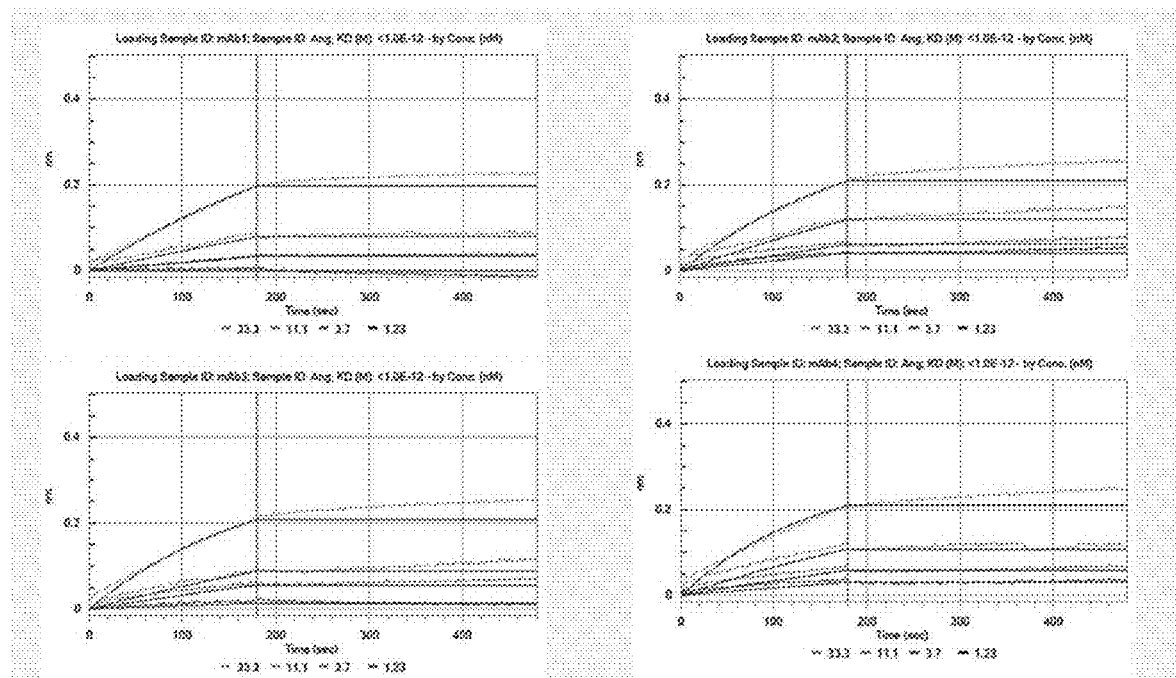
FIG. 4 depicts kinetic binding traces of the anti-DCKL1 antibodies subjected to an octet analysis.
Figure 5:
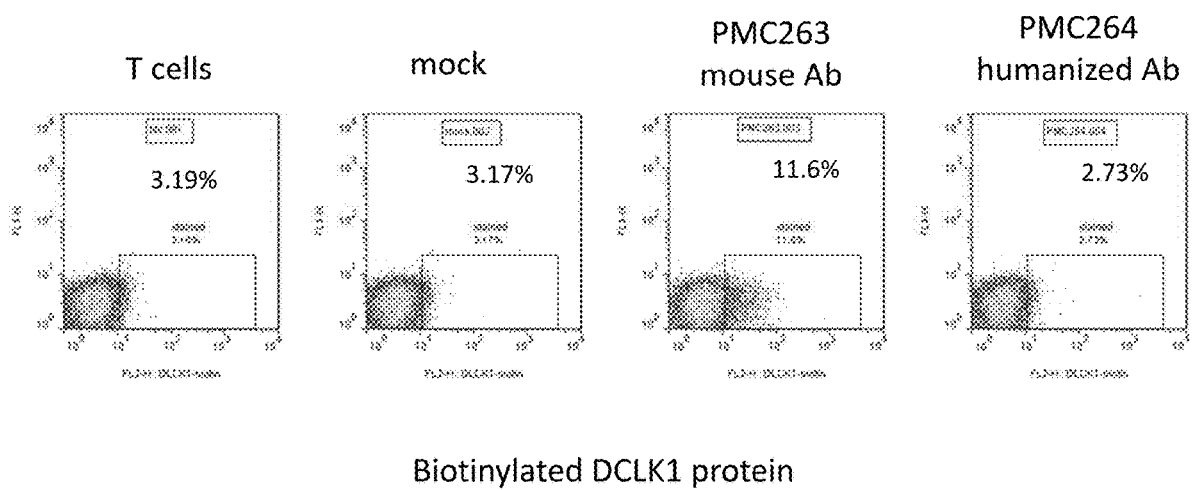
FIG. 5 shows expression of human (right panel) or mouse (second to right panel) DCLK1-CAR in T cells transduced with lentiviral DCLK1-CAR by FACS with Biotin-labeled DCLK1. T cells were effectively transduced with human or mouse DCLK1-CAR. Expression of CAR is confirmed by FACS with Biotin-labeled DCLK1 and compared with negative control non-transduced T cells (left panel).
Figure 6:
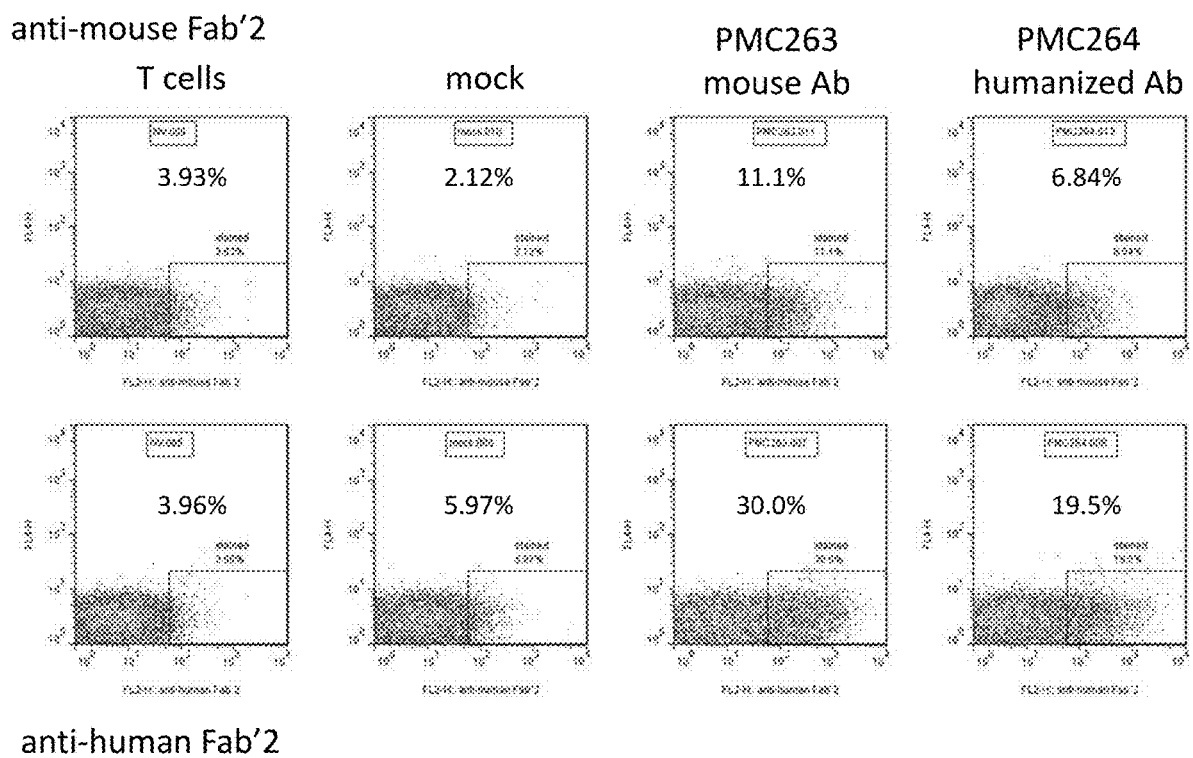
FIG. 6 depicts expression of human (right panels) or mouse (second to right panels) DCLK1-CAR in T cells transduced with lentiviral DCLK1-CAR by FACS with anti-F(ab)'2 antibodies. T cells were effectively transduced with human or mouse DCLK1-CAR. Expression of CAR is confirmed by FACS with either anti-mouse F(ab)'2 or anti-human Fab'2 and compared with negative control non-transduced T cells (left panel).
Figure 7:
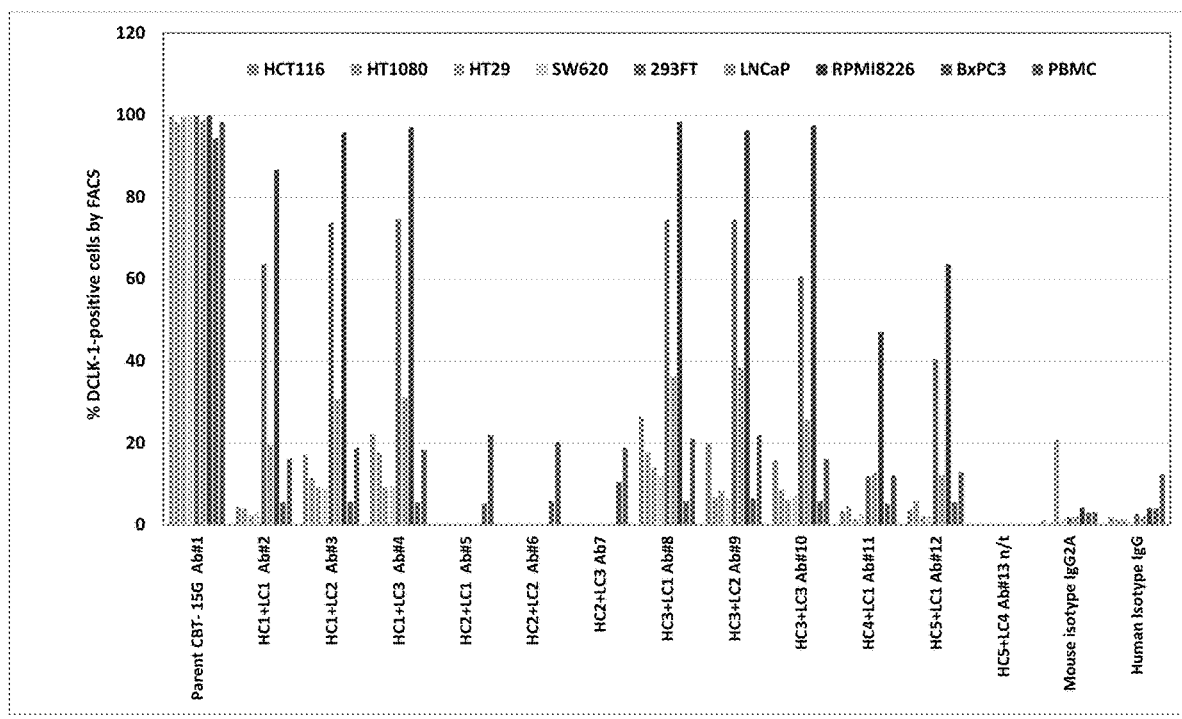
FIG. 7 shows FACs analyses of various cell lines with different variants of humanized anti-DCLK1 mAbs. Various cancer cell lines including human colorectal cancer cell lines: HCT116, HT29, SW620; human pancreatic cancer cell line BxPC3; human fibrosarcoma cell line HT1080; human prostate cancer cell line LNCaP; human multiple myeloma cell line RPMI8226; human embryonic kidney cells 293 FT; and human peripheral blood mononuclear cells. PBMC were subjected to FACS using 12 variants of humanized DCLK1 mAb. Percent DCLK1 positive cells were plotted against the mAb used.
Figure 8:
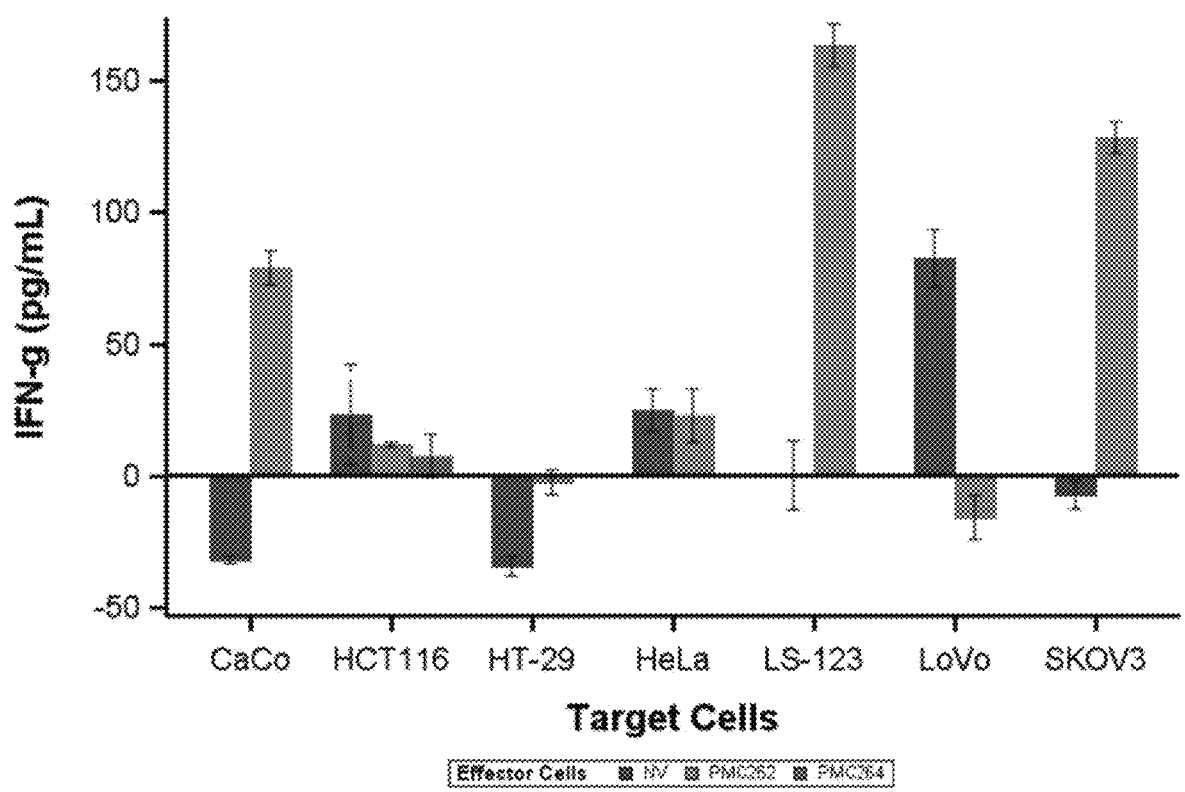
FIG. 8 shows DCLK1 CAR-T cells induced IFN-gamma in almost all the cancer cells indicating apparent IFN-gamma-dependent cytolysis. Various cancer cell lines (human colorectal cancer cell lines: CaCo2, HCT116, HT29, LS123, and LoVo; human cervical cancer cell line HeLa; or human ovarian cancer cell lines SKOV3) were treated with either human (light gray bars) or mouse (dark gray bars) DCLK1-CAR in T cells and IFN-gamma was measured.
Figure 9:
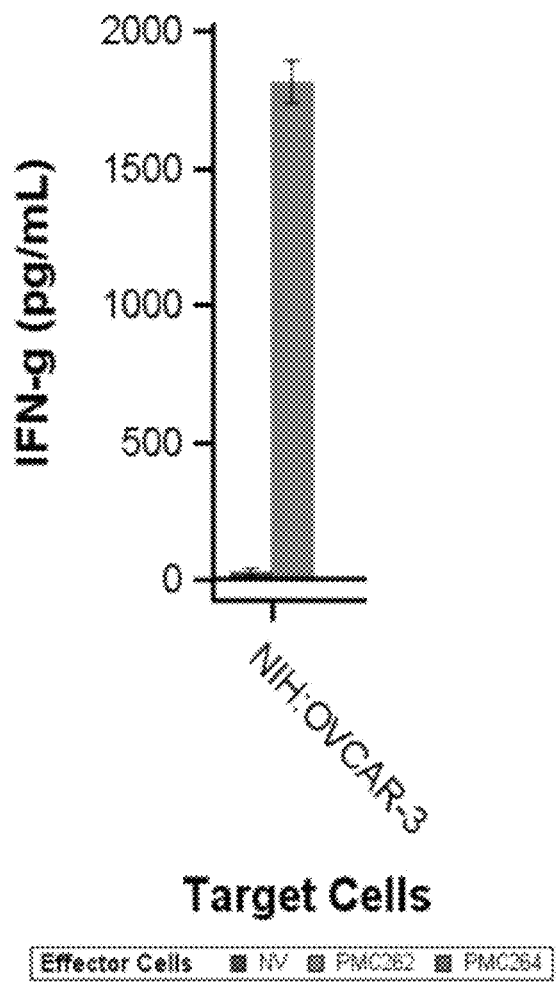
FIG. 9 shows mouse DCLK1-CAR-T induced IFN-gamma following treatment compared to non-transducer cells. Human ovarian cancer cell line OVCAR-3 was treated with either human (light gray bars) or mouse (dark gray bars) DCLK1-CAR in T cells and IFN-gamma was measured.
Figure 10:
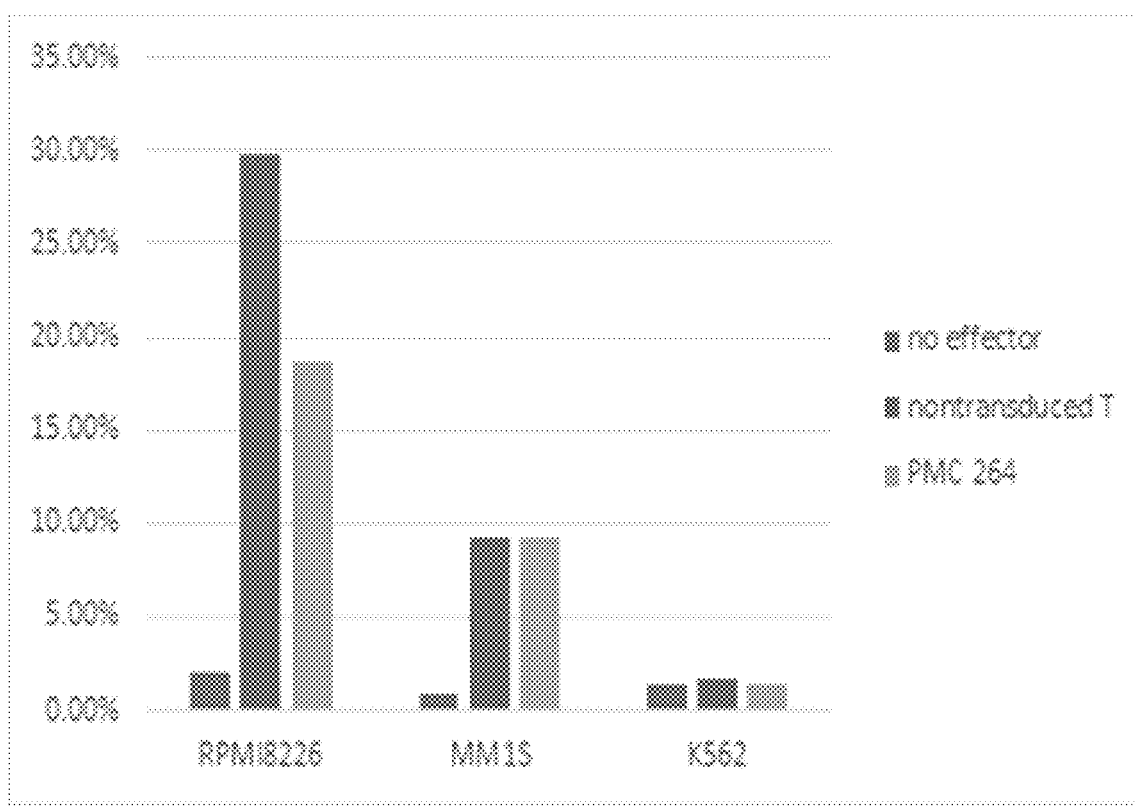
FIG. 10 depicts that in all the cancer cells DCLK1 CAR-T induced IFN-gamma compared to no effector cells indicating apparent IFN-gamma-dependent cytolysis. Various human multiple myeloma cell lines (RPMI8226, MM1S, and K562) were treated with either human DCLK1-CAR-T cells (gray bars) and IFN-gamma was measured.
Figure 11:
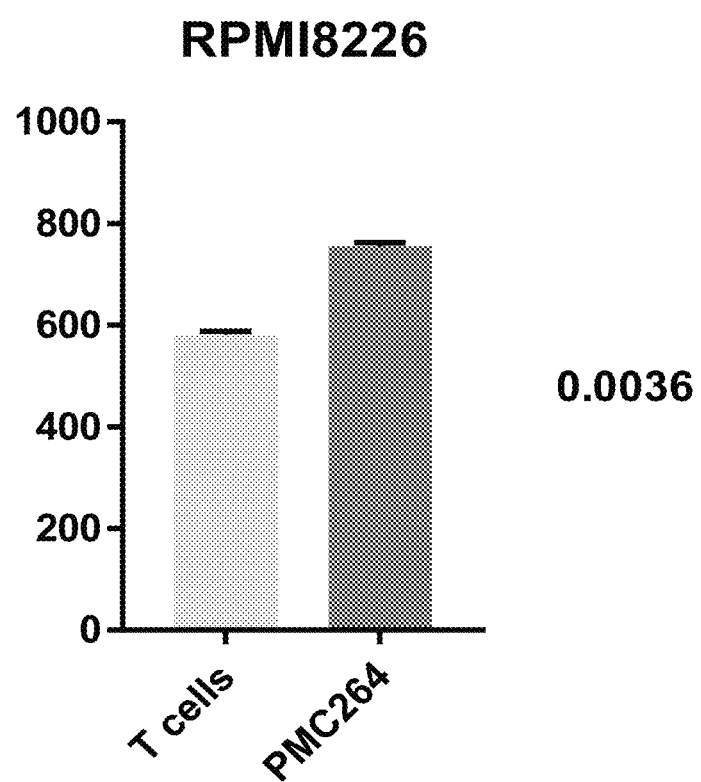
FIG. 11 depicts DCLK1 CAR-T induced IFN-gamma compared to T-cells indicating apparent IFN-gamma-dependent cytolysis. Human multiple myeloma cell line (RPMI8226) were treated with either human DCLK1-CAR-T cells (dark gray bar) or T-cells (light gray bar) and IFN-gamma was measured.
Figure 12:
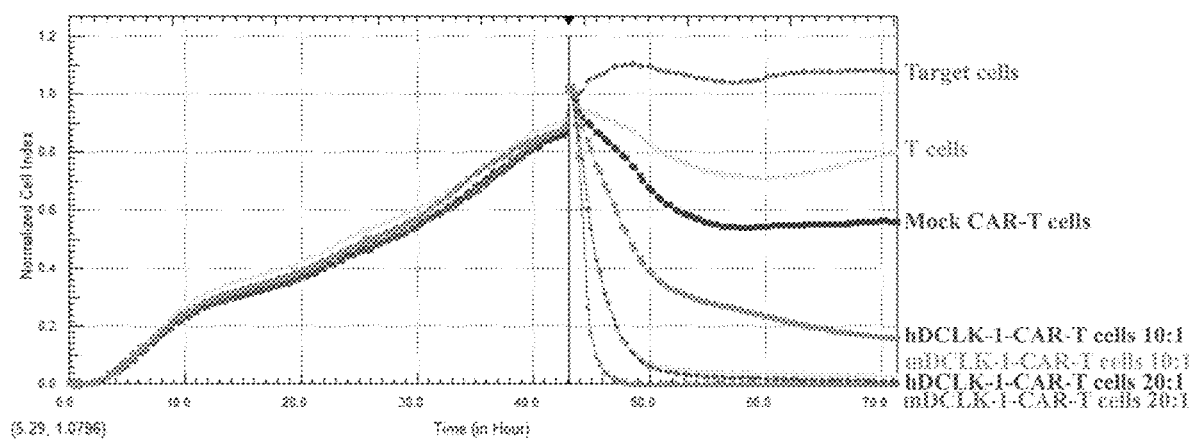
FIG. 12 depicts human and mouse DCLK1-CAR-T cells effectively killed BxPC3 cancer cell lines by Real-time cytotoxicity assay (RTCA) assay. The DCLK1-CAR-T cells-induced cytotoxicity was significantly higher than mock CAR-T cells in BxPC3 cells. The T cells alone did not significantly kill BxPC3 cancer cells.
Figure 13:
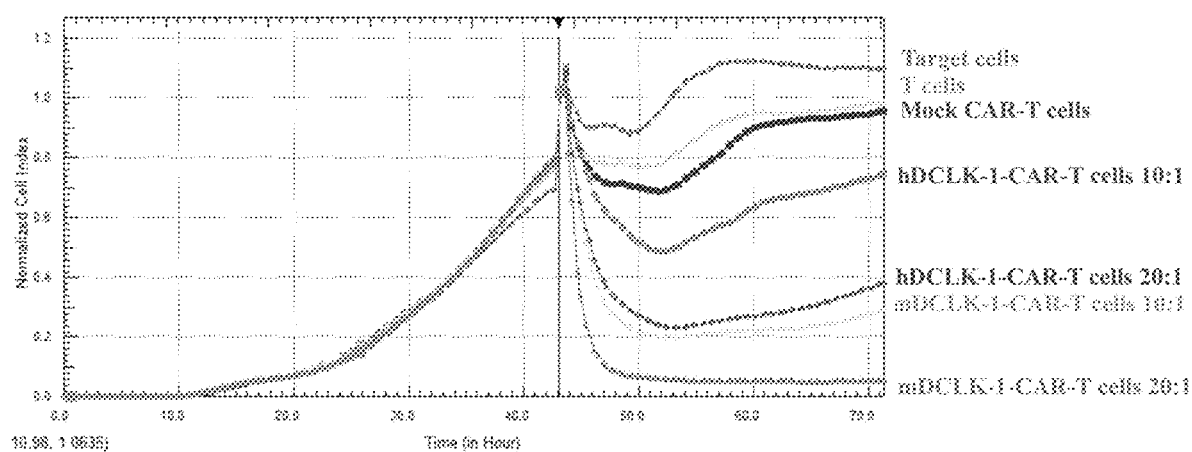
FIG. 13 shows human and mouse DCLK1-CAR-T cells effectively killed HCT116 human colorectal cancer cell lines by Real-time cytotoxicity assay (RTCA) assay. The DCLK1-CAR-T cells-induced cytotoxicity was significantly higher than mock CAR-T cells in HCT116 cells. The T cells alone did not significantly kill HCT116 cancer cells.
Figure 14:
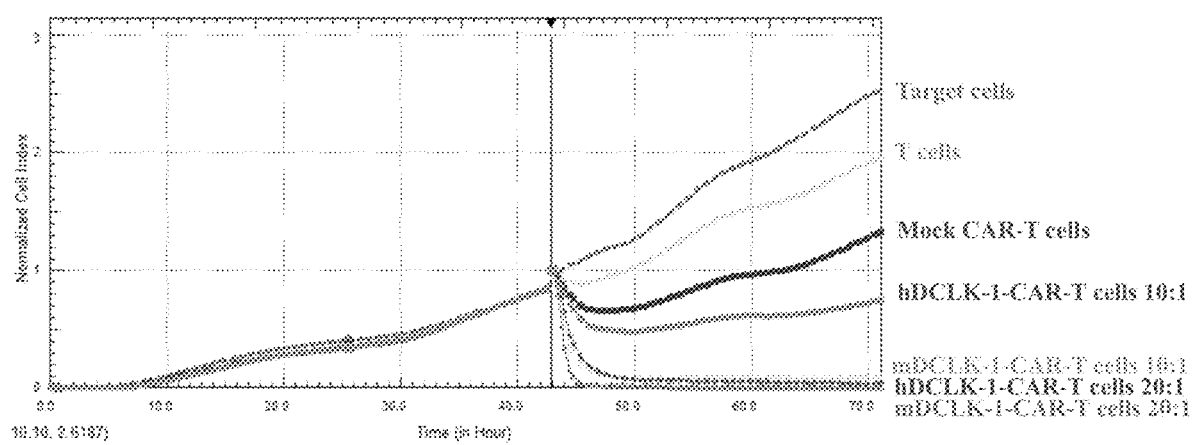
FIG. 14 shows human and mouse DCLK1-CAR-T cells effectively killed HT29 human colorectal cancer cell lines by Real-time cytotoxicity assay (RTCA) assay. The DCLK1-CAR-T cells-induced cytotoxicity was significantly higher than mock CAR-T cells in HT29 cells. The T cells alone did not significantly kill HT29 cancer cells.
Figure 15:
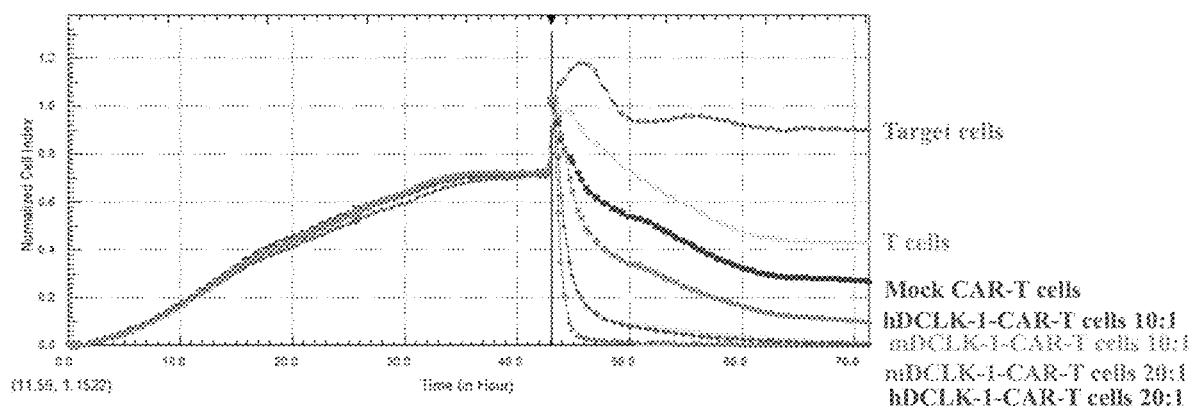
FIG. 15 shows human and mouse DCLK1-CAR-T cells effectively killed HeLa human cervical cancer cell lines by Real-time cytotoxicity assay (RTCA) assay. The DCLK1-CAR-T cells-induced cytotoxicity was significantly higher than mock CAR-T cells in Hela cells. The T cells alone did not significantly kill HeLa cancer cells.

Antibodies 374/375, L1/H4, L1/H6, and L2/H6 were subjected to Octet (Forte Bio) analysis to measure binding kinetics. FIG. 4. Antibody was loaded onto anti-human Fc biosensors and then dipped into 3-fold dilution series of antigen starting at 300 nM. As shown in the Table 7 below, all four antibodies exhibited very high binding affinities, i.e. less than $10^{-12}$ M.

TABLE 7

| Loading Sample ID | Sample ID | KD (M) | kon(1/Ms) | kdis(1/s) | FullX^2 | FullR^2 |
|---|---|---|---|---|---|---|
| mAb1 | Ang | <1.0E−12 | 9.10E+04 | <1.0E−07 | 0.2209 | 0.9798 |
| mAb2 | Ang | <1.0E−12 | 1.43E+05 | <1.0E−07 | 0.5555 | 0.9444 |
| mAb3 | Ang | <1.0E−12 | 1.70E+05 | <1.0E−07 | 0.4586 | 0.9593 |
| mAb4 | Ang | <1.0E−12 | 2.04E+05 | <1.0E−07 | 0.367 | 0.9616 |

Table 8 below shows that the humanized DCLK1 antibodies of this disclosure have high binding affinity to purified DCLK1.

TABLE 8

| Loading Sample ID | Kd (nM) | Kon (1/Ms) | Kdis (1/s) | FullX^2 | FullR^2 |
|---|---|---|---|---|---|
| Parent CBT-15G | 6.0 | 8.7E+04 | 5.3E−04 | 0.0226 | 0.9992 |
| HC1 + LC1 | 2.4 | 9.1E+04 | 2.1E−04 | 0.0139 | 0.9995 |
| HC1 + LC2 | 1.6 | 9.2E+04 | 1.5E−04 | 0.0110 | 0.9997 |
| HC1 + LC3 | 5.8 | 9.3E+04 | 5.4E−04 | 0.0312 | 0.9988 |
| HC2 + LC1 | 2.5 | 9.4E+04 | 2.3E−05 | 0.0123 | 0.9996 |
| HC2 + LC2 | 1.4 | 9.8E+04 | 1.3E−04 | 0.0155 | 0.9996 |
| HC2 + LC3 | 2.9 | 9.6E+04 | 2.8E−04 | 0.0230 | 0.9994 |
| HC3 + LC1 | 1.5 | 8.6E+04 | 1.3E−04 | 0.0130 | 0.9995 |
| HC3 + LC2 | <0.001 | 8.9E+04 | <1.0E−07 | 0.0119 | 0.9996 |
| HC3 + LC3 | 4.8 | 8.4E+04 | 4.1E−04 | 0.0228 | 0.9991 |
| HC4 + LC1 | 0.35 | 1.43E+05 | <1.0E−07 | 0.555 | 0.9444 |
| HC5 + LC1 | 0.42 | 2.04E+05 | <1.0E−07 | 0.367 | 0.9616 |
| HC5 + LC4 | 0.35 | 1.70E+05 | <1.0E−07 | 0.4586 | 0.9593 |

The results show successful humanization of a murine IgA antibody CBT-15A to a human IgG1. Twelve total humanized antibodies were produced from 293 cells and binding was assessed in comparison to chimeric CBT-15A. At least three antibodies (L1/H4, L1/H6, and L2/H6) exhibited similar high binding affinities compared to the chimeric antibody in both ELISA and Octet.

Example 3—Generation of CAR and CAR Expressing Cells

The DNA sequences for the humanized anti-DCLK1 antibodies generated in Example 1 and/or Example 2 are obtained and are incorporated into CAR vectors, e.g. a vector consisting of the following tandem genes a Kozak consensus sequence; the CD8 signal peptide; the anti-DCLK1 heavy chain variable region; a (Glycine4Serine)3 (SEQ ID NO: 86) flexible polypeptide linker; the respective anti-DCLK1 variable regions; CD8 hinge and transmembrane domains; and the CD28, 4-1BB, and CD3ζ intracellular co-stimulatory signaling domains. Hinge, transmembrane, and signaling domain DNA sequences are ascertained from a patent by Carl June (see U.S. Patent Application Publication No. 2013/0287748 A1). Anti-DCLK1 CAR genes are synthesized by Genewiz, Inc. (South Plainfield, NJ) within a pUC57 vector backbone containing the bla gene, which confers ampicillin resistance to the vector host.

NovaBlue Singles™ chemically-competent E. coli cells are transformed with anti-DCLK1 plasmid cDNA. Following growth of the transformed E. coli cells, the CAR plasmids are purified and digested with the appropriate restriction enzymes to be inserted into an HIV-1-based lentiviral vector containing HIV-1 long terminal repeats (LTRs), packaging signal (Ψ), EF1α promoter, internal ribosome entry site (IRES), and woodchuck hepatitis virus post-transcriptional regulatory element (WPRE) via overnight T₄ DNA ligase reaction (New England Biosciences; Ipswich, MA). NovaBlue Singles™ chemically-competent *E. coli* cells are then transformed with the resulting anti-DCLK1 containing lentiviral plasmid.

Prior to transfection, HEK293T cells are seeded at $4.0\times10^6$ cells/100 mm tissue-culture-treated plate in 10 mL complete-Tet-DMEM and incubated overnight at 37° C. in a humidified 5% $CO_2$ incubator. Once 80-90% confluent, HEK293T cells are co-transfected with CAR-gene lentiviral plasmids and lentiviral packaging plasmids containing genes necessary to form lentiviral envelope & capsid components, in addition to a proprietary reaction buffer and polymer to facilitate the formation of plasmid-containing nanoparticles that bind HEK293T cells. After incubating transfected-HEK293T cell cultures for 4 hours at 37° C., the transfection medium is replaced with 10 mL fresh complete Tet DMEM. HEK293T cells are then incubated for an additional 48 hours, after which cell supernatants are harvested and tested for lentiviral particles via sandwich ELISA against p24, the main lentiviral capsid protein. Lentivirus-containing supernatants are aliquoted and stored at −80° C. until use for transduction of target CD4⁺ and CD8⁺ T cells.

Peripheral blood mononuclear cells (PBMCs) are enriched by density gradient centrifugation with Ficoll-Paque Plus (GE Healthcare; Little Chalfont, Buckinghamshire, UK) are recovered and washed by centrifugation with PBS containing 0.5% bovine serum albumin (BSA) and 2 mM EDTA. MACS CD4⁺ and CD8⁺ MicroBeads (Miltenyi Biotec; San Diego, CA) kits are used to isolate these human T-cell subsets using magnetically activated LS columns to positive select for CD4⁺ and CD8⁺ T-cells. Magnetically-bound T-cells are then removed from the magnetic MACS separator, flushed from the LS column, and washed in fresh complete medium. The purity of CD4⁺ and CD8⁺ T-cell populations are assessed by flow cytometry using Life Technologies Acoustic Attune® Cytometer and are enriched by Fluorescence-Activated Cell Sorting performed at USC's flow cytometry core facilities if needed. CD4⁺ and CD8⁺ T-cells are maintained at a density of $1.0\times10^6$ cells/mL in complete medium supplemented with 100 IU/mL IL-2 in a suitable cell culture vessel, to which α-CD3/α-CD28 Human T-cell Dynabeads (Life Technologies; Carslbad, CA) are added to activate cultured T cells. T-cells are incubated at 37° C. in a 5% $CO_2$ incubator for 2 days prior to transduction with CAR-lentiviral particles.

Activated T-cells are collected, and dead cells are removed by Ficoll-Hypaque density gradient centrifugation or the use of MACS Dead Cell Removal Kit (Miltenyi Biotec; San Diego, CA). In a 6-well plate, activated T-cells are plated at a concentration of $1.0\times10^6$ cells/mL complete medium. To various wells, DCLK1 CAR-containing lentiviral particles are added to cell suspensions at varying multiplicity of infections (MOIs), such as 1, 5, 10, and 50. Polybrene, a cationic polymer that aids transduction by facilitating interaction between lentiviral particles and the target cell surface, are added at a final concentration of 4 μg/mL. Plates are centrifuged at 800×g for 1 hour at 32° C. Following centrifugation, lentivirus-containing medium are aspirated and cell pellets are resuspended in fresh complete medium with 100 IU/mL IL-2. Cells are placed in a 5% $CO_2$ humidified incubator at 37° C. overnight. Three days post-transduction, cells are pelleted and resuspended in fresh complete medium with IL-2 and 400 μg/mL Geneticin (G418 sulfate) (Life Technologies; Carlsbad, CA). DCLK1 CAR modified T-cells are assessed by flow cytometry and southern blot analysis to demonstrate successful transduction procedures. Prior to in vitro and in vivo assays, DCLK1 CAR T-cells are enriched by FACS and mixed 1:1 for the in vivo studies.

Example 4—Testing of CAR Expressing Cells in In Vitro and In Vivo Models

DCLK1 antigen positive and negative human cell lines are collected, washed, and resuspended in complete medium at a concentration of $1.0\times10^6$ cells/mL. Calcein-acetoxymethyl (AM) are added to target cell samples at 15 μM, which are then incubated at 37° C. in a 5% $CO_2$ humidified incubator for 30 minutes. Dyed positive and negative target cells are washed twice and resuspended in complete medium by centrifugation and added to a 96-well plate at $1.0\times10^4$ cells/well. DCLK1 CAR T-cells are added to the plate in complete medium at effector-to-target cell ratios of 50:1, 5:1, and 1:1. Dyed-target cells suspended in complete medium and complete medium with 2% triton X-100 serve as spontaneous and maximal release controls, respectively. The plates are centrifuged at 365×g and 20° C. for 2 minutes before being placed back in the incubator 3 hours. The plates are then centrifuged 10 minutes and cell supernatants are aliquoted to respective wells on a black polystyrene 96-well plate and assessed for fluorescence on a Bio-Tek® Synergy™ HT microplate reader at excitation and emissions of 485/20 nm and 528/20 nm, respectively.

Supernatants of DCLK1 CAR modified T-cells and DCLK1 positive and negative tumor cell lines are measured for cytokine secretion as a measure of CAR T-cell activation using standard procedures performed routinely in the laboratory. Data are compared to medium alone and to cultures using non-activated human T-cells to identify background activity. The concentration of IL-2, IFN-g, IL-12, and other pertinent cytokines are measured over time during the incubation process.

DCLK1 CAR T-cells are further evaluated in vivo using two different human tumor cell line xenograft tumor models. For both, solid tumors are established subcutaneously in 6-8-week-old female nude mice by injection of $5\times10^6$ DCLK1 positive or DCLK1 negative solid tumor cell lines. When the tumors reach 0.5 cm in diameter, groups of mice (n=5) are treated intravenously with 1 or $3\times10^7$ human T-cells as negative controls or DCLK1 CAR T-cells constructed from the most active DCLK1 antibodies based upon the in vitro study results. Tumor volumes are then measured by caliper 3×/week and volume growth curves are generated to demonstrate the effectiveness of experimental treatments over controls.

DCLK1 is found to be an outstanding target for CAR T-cell development. This experiment is replicated for other relevant immune cells, such as NK-cells, with similar results.

Example 5—Non-Liming Examples of CAR Constructs

Sequences of DCLK1 CAR construct 1

Signal peptide human CD8: MALPVTALLLPLALLL-HAARP (SEQ ID NO: 95)

NheI site sequence: AS

ScFv of anti-DCLK1

VH sequence: SEQ ID NO:3

VL sequence: SEQ ID NO:11

Xho I site sequence: LE

Flag tag sequence is optionally inserted after VL: DYKDDDDK (SEQ ID NO: 96)

CD8 hinge sequence:

CD8 hinge sequence with two S (serines) changed to cysteine (C), underlined and bolded, used in Flag tagged constructs only:

(SEQ ID NO: 97)
KPTTTPAPRPPTPAPTIASQPLSLRPEASRPAAGGAVHTRGLDFA

SDKP

CD28 Protein sequence:

(SEQ ID NO: 98)
MLRLLLALNLFPSIQVTGNKILVKQSPMLVAYDNAVNLSCKYSYN

LFSREFRASLHKGLDSAVEVCVVYGNYSQQLQVYSKTGFNCDGKL

GNESVTFYLQNLYVNQTDIYFCKIEVMYPPPYLDNEKSNGTIIHV

GHLCPSPLFPGPS*KPFWVLVWGGVLACYSLLVTVAFIIFWVK*SKR

SRLLHSDYMNMTPRRPGPTRKHYQPYAPPRDFAAYRS

The entire CD28 protein sequence is shown here. The transmembrane segment TM28 is italicized, bolded and underlined, the two binding motifs YMNM (SEQ ID NO: 99) and PYAP (SEQ ID NO: 100) are bolded, and T195 is underlined.

Transmembrane Domain TM28 sequence:

(SEQ ID NO: 101)
FWVLVVVGGVLACYSLLVTVAFIIFWV

Co-stimulating domain CD28-WT sequence:

(SEQ ID NO: 102)
RSKRSRLLHSDYMNMTPRRPGPTRKHYQPYAPPRDFAAYRS

Co-stimulating domain CD28 DD sequence: In one embodiment of the present disclosure, the two binding motifs (YMNM (SEQ ID NO: 99) and PYAP (SEQ ID NO: 100)) are immediately repeated (bolded) as shown in the following sequence:

(SEQ ID NO: 103)
FWVLVVVGGVLACYSLLVTVAFIIFWVRSKRSRLLHSDYMNMYMN

MTPRRPGPTRKHYQYAPPYAPPRDFAAYRS

Co-stimulating domain CD28 DD T195P sequence:

(SEQ ID NO: 104)
FWVLVVVGGVLACYSLLVTVAFIIFWVRSKRSRLLHSDYMNMYMN

MPPRRPGPTRKHYQYAPPYAPPRDFAAYRS

Activation domain CD3-zeta sequence:

(SEQ ID NO: 105)
RVKFSRSADAPAYQQGQNQLYNELNLGRREEYDVLDKRRGRDPEM

ETGGKPRRKNPQEGLYNELQKDKMAEAYSEIGMKGERRRGKGHDG

LYQGLSTATKDTYDALHMQALPPR

Sequences of DCLK1 CAR Construct 2

Signal peptide human CD8: MALPVTALLLPLALLL-HAARP (SEQ ID NO: 95)

NheI site sequence: AS

ScFv of anti-DCLK1

$V_H$ sequence: SEQ ID NO:7

VL sequence: SEQ ID NO:13

Xho I site sequence: LE

Flag tag sequence is optionally inserted after VL: DYKDDDDK (SEQ ID NO: 96)

CD8 hinge sequence:

CD8 hinge sequence with two S (serines) changed to cysteine (C), underlined and bolded, used in Flag tagged constructs only:

(SEQ ID NO: 97)
KPTTTPAPRPPTPAPTIASQPLSLRPEASRPAAGGAVHTRGLDFA

SDKP

CD28 Protein sequence:

(SEQ ID NO: 98)
MLRLLLALNLFPSIQVTGNKILVKQSPMLVAYDNAVNLSCKYSYN

LFSREFRASLHKGLDSAVEVCVVYGNYSQQLQVYSKTGFNCDGKL

GNESVTFYLQNLYVNQTDIYFCKIEVMYPPPYLDNEKSNGTIIHV

GHLCPSPLFPGPS*KPFWVLVWGGVLACYSLLVTVAFIIFWVK*SKR

SRLLHSDYMNMTPRRPGPTRKHYQPYAPPRDFAAYRS

The entire CD28 protein sequence is shown here. The transmembrane segment TM28 is italicized, bolded and underlined, the two binding motifs YMNM (SEQ ID NO: 99) and PYAP (SEQ ID NO: 100) are bolded and T195 is underlined.

Transmembrane Domain TM28 sequence:

(SEQ ID NO: 101)
FWVLVVVGGVLACYSLLVTVAFIIFWV

Co-stimulating domain CD28-WT sequence:

(SEQ ID NO: 102)
RSKRSRLLHSDYMNMTPRRPGPTRKHYQPYAPPRDFAAYRS

Co-stimulating domain CD28 DD sequence: In one embodiment of the present disclosure, the two binding motifs (YMNM (SEQ ID NO: 99) and PYAP (SEQ ID NO: 100)) are immediately repeated (bolded) as shown in the following sequence:

(SEQ ID NO: 103)
FWVLVVVGGVLACYSLLVTVAFIIFWVRSKRSRLLHSDYMNMYMN

MTPRRPGPTRKHYQYAPPYAPPRDFAAYRS

Co-stimulating domain CD28 DD T195P sequence:

(SEQ ID NO: 104)
FWVLVVVGGVLACYSLLVTVAFIIFWVRSKRSRLLHSDYMNMYMN

MPPRRPGPTRKHYQYAPPYAPPRDFAAYRS

Activation domain CD3-zeta sequence:

(SEQ ID NO: 105)
RVKFSRSADAPAYQQGQNQLYNELNLGRREEYDVLDKRRGRDPEM

ETGGKPRRKNPQEGLYNELQKDKMAEAYSEIGMKGERRRGKGHDG

LYQGLSTATKDTYDALHMQALPPR

Materials and Methods

Cell Lines

Hela cells were purchased from the ATCC and cultured in DMEM with 10% FBS and 1% penicillin/streptomycin. Hela-CD19 cells with stable expression of CD19 were maintained in DMEM with 10% FBS, puromycin and penicillin/streptomycin. Human peripheral blood mononuclear cells (PBMC) were isolated from whole blood obtained in the Stanford Hospital Blood Center, Stanford, CA according to IRB-approved protocol using Ficoll-Paque solution (GE Healthcare). HEK293FT cells from AlStem (Richmond, CA) were cultured in DMEM containing 10% FBS and penicillin/streptomycin. SKOV-3 cell line was obtained from ATCC and cultured in RPMI plus 10% FBS and penicillin/streptomycin. Normal human keratinocytes were obtained from the Lonza company and cultured in keratinocyte medium (Lonza) according to the manufacturer's protocol. BxPC3, PANC-1, A1847, A375, A549 and Hep-3 B were obtained from ATCC and cultured in DMEM with 10% FBS and penicillin/streptomycin. The cell lines were authenticated by flow cytometry in our laboratory, using cell-specific surface markers or by ATCC. HCT116, HT29, SW620 CaCo2, LS123, LoVo, HT1080, LNCaP, RPMI8226, MM1S, K562, and OVCAR-3 were purchased from ATCC.

CAR Lentivirus Preparation

The lentiviral CARs were used for generation of lentivirus using 293 FT cells, Lentivirus Packaging Mix and transfection agent (ALSTEM) as described in Berahovich R, Xu S, Zhou H, et al. FLAG-tagged CD19-specific CAR-T cells eliminate CD19-bearing solid tumor cells in vitro and in vivo. Front Biosci (Landmark Ed) 2017; 22:1644-1654.

The virus titers were determined by quantitative RT-PCR using the Lenti-X qRT-PCR kit (Takara) according to the manufacturer's protocol and the 7900HT thermal cycler (Thermo Fisher). The lentiviral titers were expressed in pfu/ml and ranged $1-10 \times 10^8$ pfu/ml.

CAR-T Cells Expansion

PBMC were suspended at $1 \times 10^6$ cells/ml in AIM V-AlbuMAX medium (Thermo Fisher) containing 10% FBS with 300 U/ml IL-2 (Thermo Fisher). PBMC were activated with an equal number of CD3/CD28 Dynabeads (Invitrogen), and cultured in non-treated 24-well plates. At 24 and 48 hours, lentivirus was added to the cultures at a multiplicity of infection (MOI) of 5 with 1 µl of TransPlus transduction enhancer (AlStem). The CAR-T cells were counted every 2-3 days and fresh medium with 300 U/ml IL-2 was added to the cultures to maintain the cell density at $1 \times 10^6$ cells/ml.

Flow Cytometry

To measure CAR expression, $5 \times 10^5$ cells were suspended in 100 ml of buffer (1×PBS with 0.5% BSA) and incubated on ice with 1 ml of human serum (Jackson Immunoresearch, West Grove, PA) for 10 min. Then 1 ml of allophycocyanin (APC)-labeled anti-CD3 (eBioscience, San Diego, CA), 2 ml of 7-aminoactinomycin D (7-AAD, BioLegend, San Diego, CA), and 2 ml of anti-F(ab)2 or its isotype control was added, and the cells were incubated on ice for 30 min. The cells were rinsed with buffer and acquired on a FACSCalibur (BD Biosciences). Cells were analyzed first for light scatter versus 7-AAD staining, then the 7-AAD-live gated cells were plotted for CD3 staining versus F(ab)2 staining or isotype control staining. In some experiments anti-F(ab)2 staining alone was done. For the mouse tumor studies, 100 ml of blood was stained at room temperature for 30 min with 1 ml of APC anti-CD3, 2 ml of fluorescein isothiocyanate (FITC)-labeled anti-CD8a (eBioscience), 2 ml of 7-AAD. Erythrocytes were lysed with 3.5. ml of RBC lysing solution (150 mM NH4Cl, 10 mM NaHCO$_3$, 1 mM EDTA pH 8), then leukocytes were collected by centrifugation and rinsed with 2 ml of cold buffer before acquisition. For expression of DCLK1, mouse or human antibody (COARE Holdings Inc.,) at 10 mg/ml concentration was used. The isotype IgG1 isotype antibody was used at 10 mg/ml from (BioLegend, San Diego, CA).

Real-Time Cytotoxicity Assay (RTCA)

Adherent target cells were seeded into 96-well E-plates (Acea Biosciences, San Diego, CA) at $1 \times 10^4$ cells per well and monitored in culture overnight with the impedance-based real-time cell analysis (RTCA) iCELLigence system (Acea Biosciences). The next day, the medium was removed and replaced with AIM V-AibuMAX medium containing 10% FBS±$1 \times 10^5$ effector cells (CAR-T cells or non-transduced T cells), in triplicate. The cells were monitored for another 2 days with the RTCA system, and impedance was plotted over time. Cytolysis was calculated as (impedance of target cells without effector cells—impedance of target cells with effector cells)×100/impedance of target cells without effector cells.

Cytokine ELISA Assay

The target cells were cultured with the effector cells (CAR-T cells or non-transduced T cells) at a 1:1 ratio ($1 \times 10^4$ cells each) in U-bottom 96-well plates with 200 µl of AIM V-AlbuMAX medium containing 10% FBS, in triplicate. After 16 h the top 150 µl of medium was transferred to V-bottom 96-well plates and centrifuged at 300 g for 5 min to pellet any residual cells. In some experiments supernatant after RTCA assay at E:T=10:1 was used for cytokine ELISA assays. The supernatant was transferred to a new 96-well plate and analyzed by ELISA for human cytokine levels (IFN-gamma, IL-2, IL-6) using kits from Thermo Fisher according to the manufacturer's protocol.

Binding Assay with Humanized and Mouse DCLK-1 scFv.

The mouse or humanized DCLK-1 scFv contained VL and VH sequences that were linked with G4Sx3 linker (SEQ ID NO: 86). The scFvs were fused in frame with C-terminal human Fc inside pYD11 vector used for recombinant DCLK-1 scFv protein expression. The supernatant with mammalian expressed ScFv protein were used for binding assay at equal amount. All scFv were checked by Western blotting with anti-human Fc antibody for expression. The human extracellular domain of human DCLK-1 protein was fused with mouse Fc and used for ELISA assay with DCLK-1 scFv. The OD reading at 450 nm was used for detecting binding. The in-silico model was generated for humanized VH and VL sequences based on the mouse sequences.

Statistical Analysis

Data were analyzed and plotted with Prism software (GraphPad, San Diego, CA). Comparisons between two groups were performed by unpaired Student's t test, and comparisons between three groups were performed by one-way ANOVA with Tukey's post-hoc test, except where noted. The difference was considered significant with p-value<0.05.

EQUIVALENTS

Unless otherwise defined, all technical and scientific terms used herein have the same meaning as commonly understood by one of ordinary skill in the art to which this technology belongs.

The present technology illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the present technology claimed.

Thus, it should be understood that the materials, methods, and examples provided here are representative of particular aspects, are exemplary, and are not intended as limitations on the scope of the present technology.

The present technology has been described broadly and generically herein. Each of the narrower species and sub-generic groupings falling within the generic disclosure also form part of the present technology. This includes the generic description of the present technology with a proviso or negative limitation removing any subject matter from the genus, regardless of whether or not the excised material is specifically recited herein.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

The invention claimed is:

1. An anti-Doublecortin-like kinase 1 (DCLK1) antibody or antigen binding fragment thereof comprising:
   (i) heavy chain (HC) complementarity-determining regions (CDRs) CDRH1, CDRH2, and CDRH3 from an HC immunoglobulin variable domain sequence selected from the group consisting of SEQ ID NOs: 7, 8, 9, 16, 22, 23, and 24; and
   (ii) light chain (LC) complementarity-determining regions (CDRs) CDRL1, CDRL2, and CDRL3 from an LC immunoglobulin variable domain sequence selected from the group consisting of SEQ ID NOs: 12, 13, 14, 26, 27, 28, 29, and 30.

2. A nucleic acid sequence encoding the antibody or antigen binding fragment of claim 1.

3. A vector comprising the nucleic acid sequence of claim 2.

4. A cell comprising the nucleic acid sequence of claim 2.

5. The cell of claim 4, wherein the cell is an immune cell, a T-cell, or a natural killer (NK) cell.

6. A composition comprising a carrier and the cell of claim 4.

7. A composition comprising a carrier and the antibody or antigen binding fragment thereof of claim 1.

8. The anti-DCLK-1 antibody or antibody binding fragment of claim 1, wherein the antibody is selected from the group consisting of intact immunoglobulins, humanized antibodies, chimeric antibodies, single chain antibodies, heteroconjugate antibodies, and bispecific antibodies.

9. The anti-DCLK-1 antibody or antigen binding fragment of claim 1, wherein the antibody or antigen binding fragment is humanized.

10. The anti-DCLK1 antibody or antigen binding fragment thereof of claim 1, wherein CDRL1, CDRL2, and CDRL3 are from SEQ ID NO: 12.

11. The anti-DCLK1 antibody or antigen binding fragment thereof of claim 1, wherein CDRL1, CDRL2, and CDRL3 are from SEQ ID NO: 13.

12. The anti-DCLK1 antibody or antigen binding fragment thereof of claim 1, wherein CDRL1, CDRL2, and CDRL3 are from SEQ ID NO: 14.

13. The anti-DCLK1 antibody or antigen binding fragment thereof of claim 1, wherein CDRL1, CDRL2, and CDRL3 are from SEQ ID NO: 26.

14. The anti-DCLK1 antibody or antigen binding fragment thereof of claim 1, wherein CDRL1, CDRL2, and CDRL3 are from SEQ ID NO: 27.

15. The anti-DCLK1 antibody or antigen binding fragment thereof of claim 1, wherein CDRL1, CDRL2, and CDRL3 are from SEQ ID NO: 28.

16. The anti-DCLK1 antibody or antigen binding fragment thereof of claim 1, wherein CDRL1, CDRL2, and CDRL3 are from SEQ ID NO: 29.

17. The anti-DCLK1 antibody or antigen binding fragment thereof of claim 1, wherein CDRL1, CDRL2, and CDRL3 are from SEQ ID NO: 30.

18. A kit comprising the antibody or antigen binding fragment thereof of claim 1, and instructions for use thereof.

* * * * *

UNITED STATES PATENT AND TRADEMARK OFFICE
CERTIFICATE OF CORRECTION

Page 1 of 1

PATENT NO. : 12,415,867 B2
APPLICATION NO. : 18/427038
DATED : September 16, 2025
INVENTOR(S) : Courtney W. Houchen It is certified that error appears in the above-identified patent and that said Letters Patent is hereby corrected as shown below:

In the Specification

Column 1, Line 14: Delete "119(c)" and replace with -- 119(e) --

Column 8, Line 46: Delete "p-sheet" and replace with -- β-sheet --

Column 8, Line 48: Delete "j-sheet" and replace with -- β-sheet --

Column 10, Line 62: Delete "015075." and replace with -- O15075. --

Column 18, Line 50: Delete "KOPT-KI," and replace with -- KOPT-K1, --

Column 38, Line 35: After "stabilized" delete "F," and replace with -- $F_v$ --

Signed and Sealed this
Twenty-first Day of October, 2025

John A. Squires
*Director of the United States Patent and Trademark Office*